(12) United States Patent
Nakashima et al.

(10) Patent No.: US 9,478,751 B2
(45) Date of Patent: Oct. 25, 2016

(54) ANTHRACENE DERIVATIVE, LIGHT EMITTING ELEMENT USING THE SAME, AND LIGHT EMITTING DEVICE USING THE SAME

(71) Applicant: Semiconductor Energy Laboratory Co., Ltd., Kanagawa-ken (JP)

(72) Inventors: Harue Nakashima, Kanagawa (JP); Sachiko Kawakami, Kanagawa (JP); Kumi Kojima, Tokyo (JP); Ryoji Nomura, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/466,422

(22) Filed: Aug. 22, 2014

(65) Prior Publication Data

US 2014/0364626 A1 Dec. 11, 2014

Related U.S. Application Data

(63) Continuation of application No. 11/793,479, filed as application No. PCT/JP2005/024206 on Dec. 26, 2005, now Pat. No. 8,815,410.

(30) Foreign Application Priority Data

Dec. 28, 2004 (JP) .................................. 2004-381181
Jul. 25, 2005 (JP) .................................. 2005-214124

(51) Int. Cl.
| | | |
|---|---|---|
| *H01L 51/50* | (2006.01) | |
| *H01L 51/00* | (2006.01) | |
| *C07D 403/12* | (2006.01) | |
| *C09K 11/06* | (2006.01) | |
| *H05B 33/14* | (2006.01) | |

(52) U.S. Cl.
CPC ......... *H01L 51/0058* (2013.01); *C07D 403/12* (2013.01); *C09K 11/06* (2013.01); *H01L 51/006* (2013.01); *H01L 51/0052* (2013.01); *H01L 51/0061* (2013.01); *H01L 51/0072* (2013.01); *H05B 33/14* (2013.01); *C09K 2211/1011* (2013.01); *C09K 2211/1014* (2013.01); *C09K 2211/1022* (2013.01); *C09K 2211/1029* (2013.01); *H01L 51/0081* (2013.01); *H01L 51/5012* (2013.01); *H01L 2251/308* (2013.01)

(58) Field of Classification Search
None
See application file for complete search history.

(56) References Cited

U.S. PATENT DOCUMENTS 5,756,248 A 5/1998 Tanaka et al.
5,811,834 A 9/1998 Tamano et al.
(Continued)

FOREIGN PATENT DOCUMENTS

CN 001407053 A 4/2003
EP 0 786 926 A2 7/1997
(Continued)

OTHER PUBLICATIONS

Thomas et al., Light-Emitting Carbazole Derivatives: Potential Electrolumininescent Materials, 2001, J. Am. Chem. Soc., vol. 123, pp. 9404-9411.*
(Continued)

*Primary Examiner* — Gregory Clark
(74) *Attorney, Agent, or Firm* — Husch Blackwell LLP

(57) ABSTRACT

It is an object of the present invention to provide a light emitting element, which is resistant to repetition of an oxidation reaction. It is another object of the invention to provide a light emitting element, which is resistant to repetition of a reduction reaction. An anthracene derivative is represented by a general formula (1). In the general formula (1), R1 represents hydrogen or an alkyl group having 1 to 4 carbon atoms, R2 represents any one of hydrogen, an alkyl group having 1 to 4 carbon atoms and an aryl group having 6 to 12 carbon atoms, R3 represents any one of hydrogen, an alkyl group having 1 to 4 carbon atoms, and an aryl group having 6 to 12 carbon atoms, Ph1 represents a phenyl group, and X1 represents an arylene group having 6 to 15 carbon atoms.

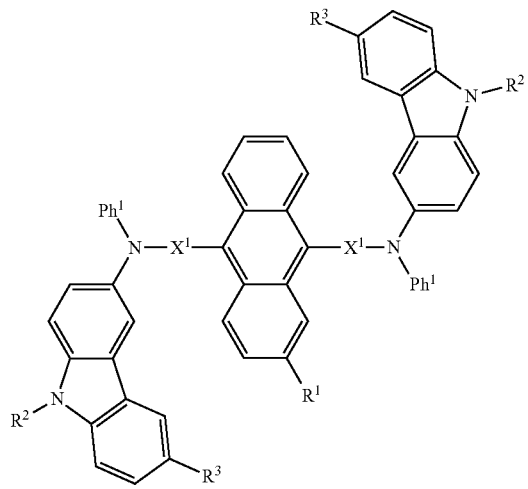

20 Claims, 49 Drawing Sheets

(56) References Cited

U.S. PATENT DOCUMENTS

| | | | |
|---|---|---|---|
| 5,972,247 A | 10/1999 | Shi et al. |
| 5,990,629 A | 11/1999 | Yamada et al. |
| 6,451,461 B2 | 9/2002 | Lee et al. |
| 6,465,115 B2 | 10/2002 | Shi et al. |
| 6,541,129 B1 | 4/2003 | Kawamura et al. |
| 6,660,408 B1 | 12/2003 | Toguchi et al. |
| 6,661,023 B2 | 12/2003 | Hoag et al. |
| 6,730,419 B2 | 5/2004 | Kim et al. |
| 6,743,948 B1 | 6/2004 | Hosokawa et al. |
| 6,764,846 B2 | 7/2004 | Yamamori et al. |
| 6,767,654 B2 | 7/2004 | Tamao et al. |
| 6,929,871 B2 | 8/2005 | Arakane et al. |
| 6,951,693 B2 | 10/2005 | Hosokawa et al. |
| 7,399,537 B2 | 7/2008 | Kawamura et al. |
| 7,632,577 B2 | 12/2009 | Saitoh et al. |
| 7,879,465 B2 | 2/2011 | Arakane et al. |
| 2003/0044643 A1 | 3/2003 | Arakane et al. |
| 2003/0064246 A1 | 4/2003 | Kim et al. |
| 2003/0072966 A1 | 4/2003 | Hosokawa et al. |
| 2003/0143430 A1 | 7/2003 | Kawamura et al. |
| 2003/0215667 A1 | 11/2003 | Xie |
| 2005/0038296 A1 | 2/2005 | Hosokawa et al. |
| 2005/0064233 A1 | 3/2005 | Matsuura et al. |
| 2005/0112404 A1 | 5/2005 | Hamada et al. |
| 2005/0244676 A1 | 11/2005 | Arakane et al. |
| 2005/0260450 A1 | 11/2005 | Yamagata et al. |
| 2006/0020136 A1 | 1/2006 | Hwang et al. |
| 2006/0068221 A1 | 3/2006 | Saitoh et al. |
| 2006/0082294 A1 | 4/2006 | Kawamura et al. |
| 2006/0115680 A1 | 6/2006 | Hwang et al. |
| 2007/0031701 A1 | 2/2007 | Nakashima et al. |
| 2007/0075632 A1 | 4/2007 | Kawakami et al. |
| 2007/0254186 A1 | 11/2007 | Arakane et al. |
| 2008/0241591 A1 | 10/2008 | Kawamura et al. |
| 2008/0254318 A1 | 10/2008 | Nakashima et al. |
| 2009/0015140 A1 | 1/2009 | Kawakami et al. |

FOREIGN PATENT DOCUMENTS

| | | |
|---|---|---|
| EP | 0 952 200 A2 | 10/1999 |
| EP | 1 029 909 A1 | 8/2000 |
| EP | 1 061 112 A1 | 12/2000 |
| EP | 0 786 926 B1 | 8/2001 |
| EP | 1 170 359 A1 | 1/2002 |
| EP | 0 952 200 B1 | 12/2002 |
| EP | 1 347 031 A1 | 9/2003 |
| JP | 09-268283 A | 10/1997 |
| JP | 11-312588 A | 11/1999 |
| JP | 11-339963 A | 12/1999 |
| JP | 2000-309566 A | 11/2000 |
| JP | 2001-131541 A | 5/2001 |
| JP | 2003-031371 A | 1/2003 |
| JP | 2004-087363 A | 3/2004 |
| JP | 2004-087393 A | 3/2004 |
| JP | 2004-087395 A | 3/2004 |
| WO | WO 02/20693 A1 | 3/2002 |
| WO | WO 2004/020548 A1 | 3/2004 |

OTHER PUBLICATIONS

International Search Report re Application No. PCT/JP2005/024206, dated Feb. 21, 2006.

Written Opinion re Application No. PCT/JP2005/024206, dated Feb. 21, 2006.

Thomas, K.R.J. et al., "New Carbazole-Oxadiazole Dyads for Electroluminescent Devices: Influence of Acceptor Substituents on Luminescent and Thermal Properties," Chemistry of Materials, 2004, vol. 16, No. 25, pp. 5437-5444.

Korean Office Action re Application No. KR 2012-7033909, dated Apr. 4, 2013.

Chinese Office Action re Application No. CN 201210020340.1, dated Jan. 6, 2014.

\* cited by examiner

ANTHRACENE DERIVATIVE, LIGHT EMITTING ELEMENT USING THE SAME, AND LIGHT EMITTING DEVICE USING THE SAME

This application is a continuation of copending application Ser. No. 11/739,479 filed on Jun. 15, 2007 which is the US National Stage under 35 USC 371 of PCT/JP2005/024206 filed on Dec. 26, 2005, all of which are incorporated herein by reference.

TECHNICAL FIELD

The present invention relates to an anthracene derivative, and in particular, relates to an anthracene derivative that can be used as a material for manufacturing a light emitting element.

BACKGROUND ART

In recent years, many of light emitting elements used for displays and the like have a structure in which a layer containing a light emitting substance is interposed between a pair of electrodes. Such light emitting elements emit light when an exciton that is generated by recombination of an electron injected from one electrodes and a hole injected from the other electrodes returns to a ground state.

In order to obtain a light emitting element having an excellent light emitting efficiency and good chromaticity or a light emitting element that can prevent optical quenching and the like, various researches about substances that can be used as materials for manufacturing such a light emitting element have been carried out in the field of light emitting elements.

For example, the patent document 1 discloses a material for an organic EL element having an excellent light emitting efficiency and long term durability.

Meanwhile, in a light emitting element, a current flows between electrodes by transportation of holes or electrons. In this case, a light emitting substance that receives holes or electrons or the like, or, a light emitting substance that is oxidized or reduced or the like sometimes does not return to a neutral state and is changed to a different substance having a different property and a different structure. When the changes of the property and structure of the light emitting substance are accumulated, a characteristic of the light emitting element may also be changed.

Therefore, there are high expectations for a development of a light emitting substance of which a property is difficult to be changed due to oxidation or reduction.

Patent Document 1: Japanese Patent Application Laid-Open No. 2001-131541.

DISCLOSURE OF INVENTION

It is an object of the present invention to provide a substance that has high resistance to repetition of an oxidation reaction and can be used as a material for a light emitting element. Moreover, it is another object of the invention to provide a light emitting element and a light emitting device each in which deterioration in an operational characteristic of the light emitting element due to change in a characteristic of a substance caused by repetition of an oxidation reaction is reduced.

An aspect of the present invention is an anthracene derivative represented by a general formula (1)

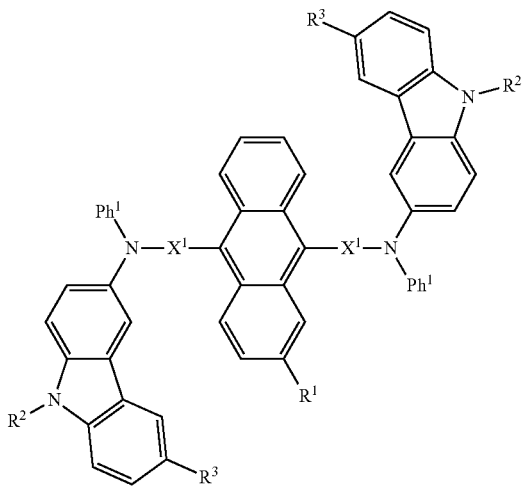

(1)

In the general formula (1), $R^1$ represents either hydrogen or an alkyl group having 1 to 4 carbon atoms. $R^2$ represents any one of hydrogen, an alkyl group having 1 to 4 carbon atoms and an aryl group having 6 to 12 carbon atoms. The aryl group may have a substituent or no substituent. $R^3$ represents any one of hydrogen, an alkyl group having 1 to 4 carbon atoms, and an aryl group having 6 to 12 carbon atoms. The aryl group may have a substituent or no substituent. $Ph^1$ represents a phenyl group. The phenyl group may have a substituent or no substituent. $X^1$ represents an arylene group having 6 to 15 carbon atoms. The arylene groups may has a substituent or no substituent.

Another aspect of the present invention is an anthracene derivative represented by a general formula (2).

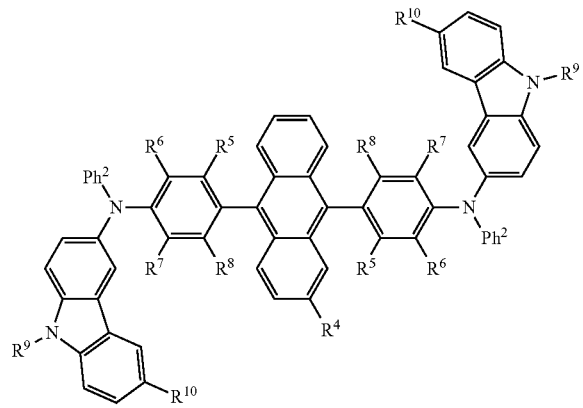

(2)

In the general formula (2), $R^4$ represents either hydrogen or an alkyl group having 1 to 4 carbon atoms. $R^5$ and $R^6$ represent hydrogen, or, aromatic rings which are bonded to each other, and $R^7$ and $R^8$ represent hydrogen, or, aromatic rings which are bonded to each other. $R^9$ represents any one of hydrogen, an alkyl group having 1 to 4 carbon atoms, and an aryl group having 6 to 12 carbon atoms. The aryl group may have a substituent or no substituent. $R^{10}$ represents any one of hydrogen, an alkyl group having 1 to 4 carbon atoms, and an aryl group having 6 to 12 carbon atoms. The aryl group may have a substituent or no substituent. $Ph^2$ represents a phenyl group. The phenyl group may have a substituent or no substituent.

Another aspect of the present invention is an anthracene derivative represented by a general formula (3).

(3)

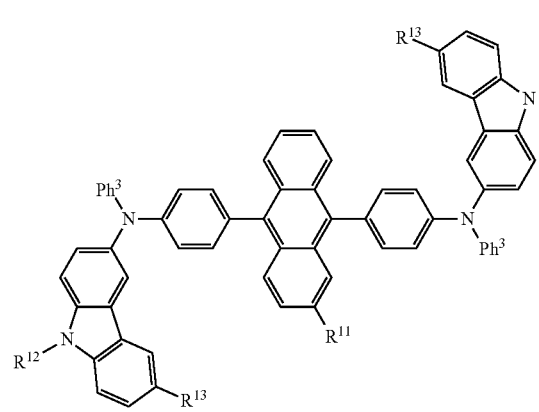

In the general formula (3), $R^{11}$ represents either hydrogen or an alkyl group having 1 to 4 carbon atoms. $R^{12}$ represents any one of hydrogen, an alkyl group having 1 to 4 carbon atoms, and an aryl group having 6 to 12 carbon atoms. The aryl group may have a substituent or no substituent. $R^{13}$ represents any one of hydrogen, an alkyl group having 1 to 4 carbon atoms, and an aryl group having 6 to 12 carbon atoms. The aryl group may have a substituent or no substituent. $Ph^3$ represents a phenyl group. The phenyl group may have a substituent or no substituent.

Another aspect of the present invention is an anthracene derivative represented by a general formula (4).

(4)

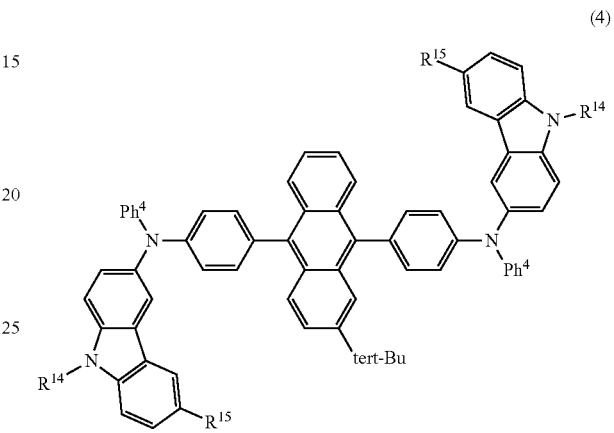

In the general formula (4), $R^{14}$ represents any one of hydrogen, an alkyl group having 1 to 4 carbon atoms, and an aryl group having 6 to 12 carbon atoms. The aryl group may have a substituent or no substituent. $R^{15}$ represents any one of hydrogen, an alkyl group having 1 to 4 carbon atoms, and an aryl group having 6 to 12 carbon atoms. The aryl group may have a substituent or no substituent. $Ph^4$ represents a phenyl group. The phenyl group may have a substituent or no substituent.

Another aspect of the present invention is an anthracene derivative represented by a general formula (5).

(5)

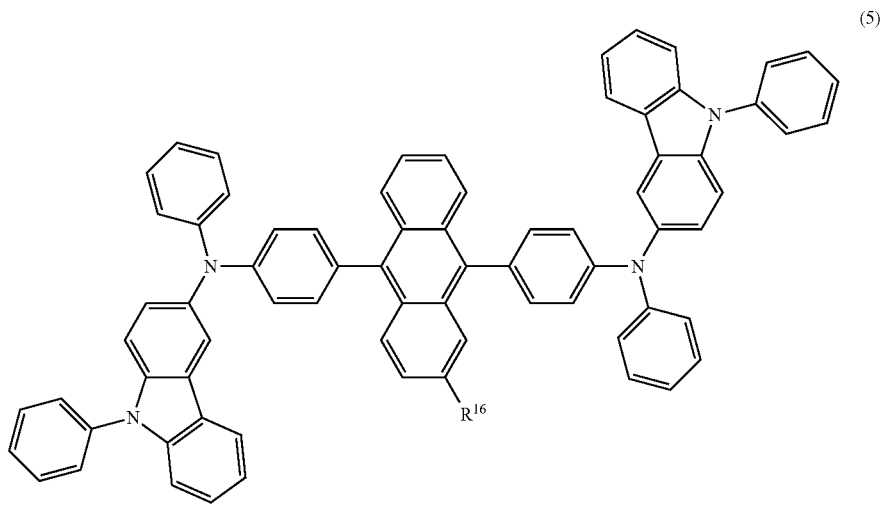

In the general formula (5), $R^{16}$ represents either hydrogen or an alkyl group having 1 to 4 carbon atoms.

Another aspect of the present invention is an anthracene derivative represented by a general formula (6).

In the general formula (6), $X^2$ represents an arylene group having 6 to 15 carbon atoms. The arylene group may have a substituent or no substituent.

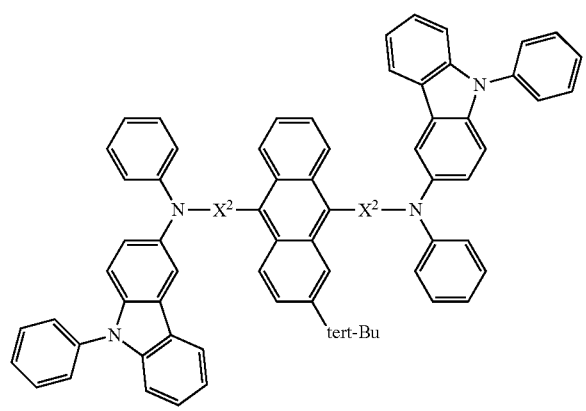

(6)

Another aspect of the present invention is an anthracene derivative represented by a general formula (7).

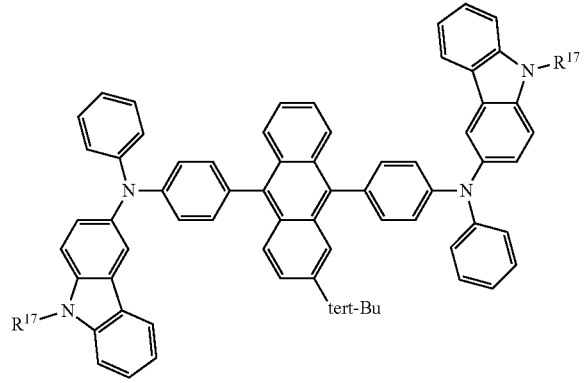

(7)

In the general formula (7), $R^{17}$ represents any one of hydrogen, an alkyl group having 1 to 4 carbon atoms, and an aryl group having 6 to 12 carbon atoms. The aryl group may have a substituent or no substituent.

Another aspect of the present invention is an anthracene derivative represented by a general formula (8).

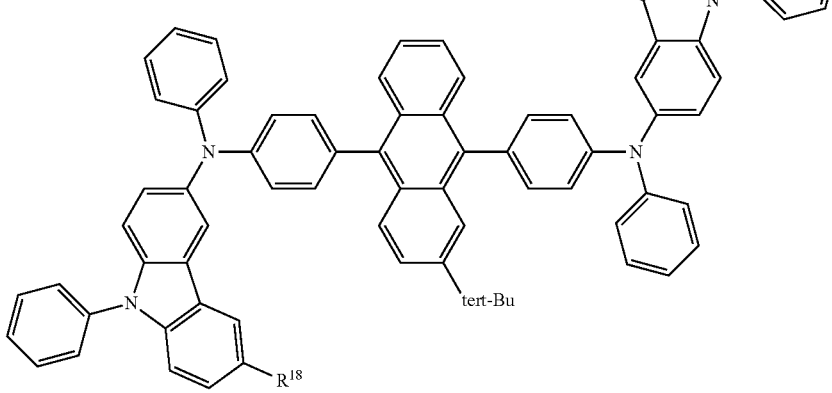

(8)

In the genera formula (8), $R^{18}$ represents any one of hydrogen, an alkyl group having 1 to 4 carbon atoms, and an aryl group having 6 to 12 carbon atoms. The aryl group may have a substituent or no substituent.

Another aspect of the present invention is a light emitting element that has a layer containing an anthracene derivative represented by any one of the general formulas (1) to (8), between electrodes.

Another aspect of the present invention is a light emitting device using a light emitting element containing an anthracene derivative represented by any one of the general formulas (1) to (8).

Another aspect of the present invention is a light emitting device that has a light emitting element containing an anthracene derivative represented by any one of the general formulas (1) to (8), in a pixel portion.

Another aspect of the present invention is an electronic appliance mounted with a light emitting device that uses a light emitting element containing an anthracene derivative represented by any one of the general formulas (1) to (8).

In accordance with the present invention, a substance being highly resistant to repetition of an oxidation reaction, which can be used as a material for manufacturing a light emitting element, can be obtained. In addition, in accordance with the present invention, it is possible to obtain a substance being highly resistant to repetition of an oxidation reaction and repetition of a reduce reaction, which can be used as a material for manufacturing a light emitting element.

By implementing the present invention, it is possible to obtain a light emitting element in which deterioration in an element characteristic caused by repetition of an oxidation reaction of a substance, which is used in a layer provided between electrodes, can be reduced. It is also possible to obtain a light emitting element that can stably emit light for a long time and has less changes in a characteristic of the light emitting element cased with change in a property of a light emitting substance due to repetition of an oxidation reaction.

BEST MODE FOR CARRYING OUT THE INVENTION

Figure 1:
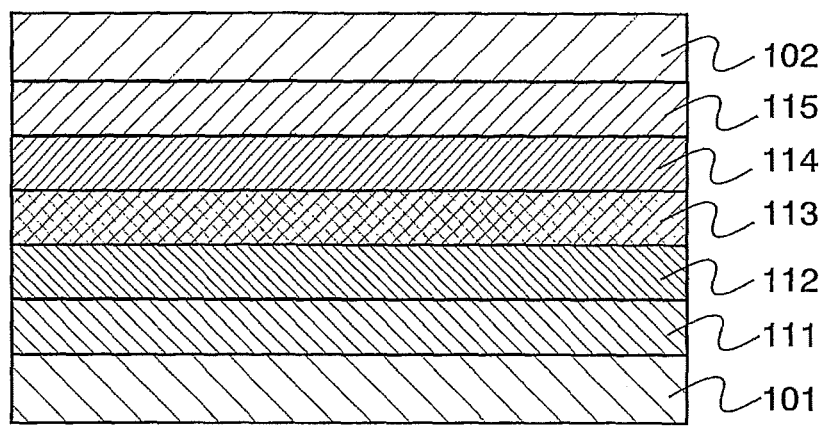
FIG. 1 is a cross sectional view explaining a light emitting element of the present invention.

The embodiment modes according to the present invention will hereinafter be described. It is easily understood by those skilled in the art that the embodiment modes and details herein disclosed can be modified in various ways without departing from the purpose and the scope of the invention. The present invention should not be interpreted as being limited to the description of the embodiment modes to be given below.

[Embodiment Mode 1]

A mode of an anthracene derivative of the present invention will be described.

As an anthracene derivative of the present invention, anthracene derivatives represented by the following structural formulas (1) to (40) can be given.
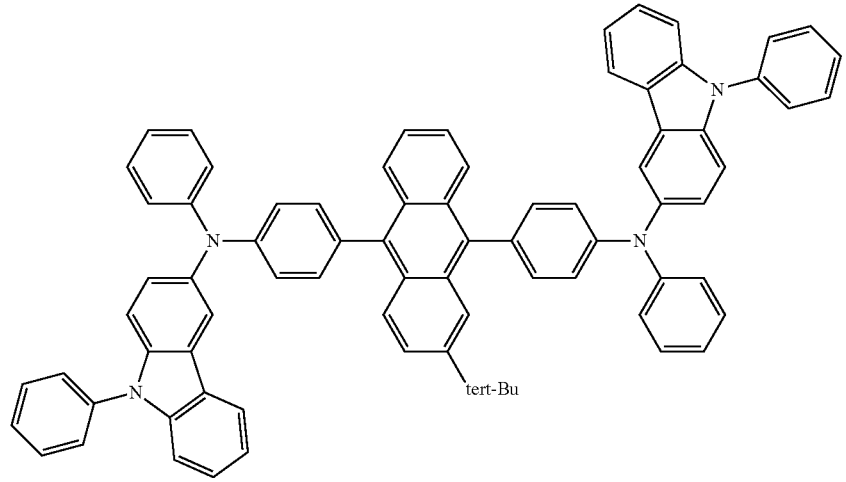
(1)
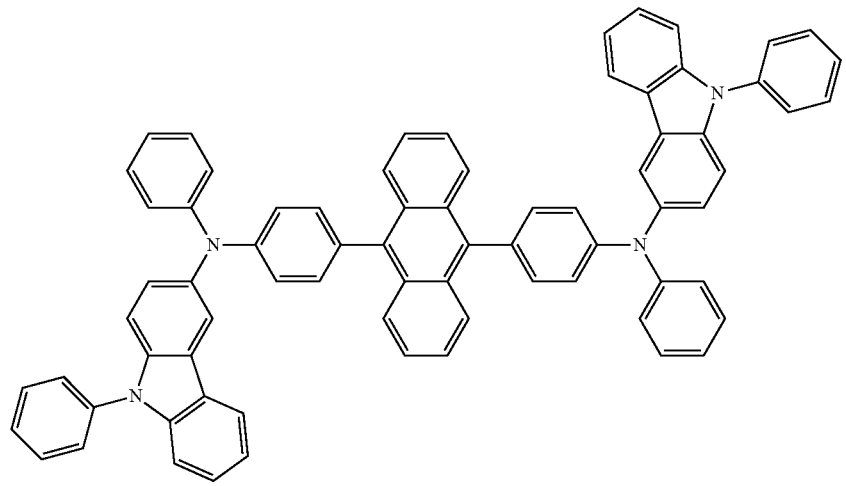
(2)
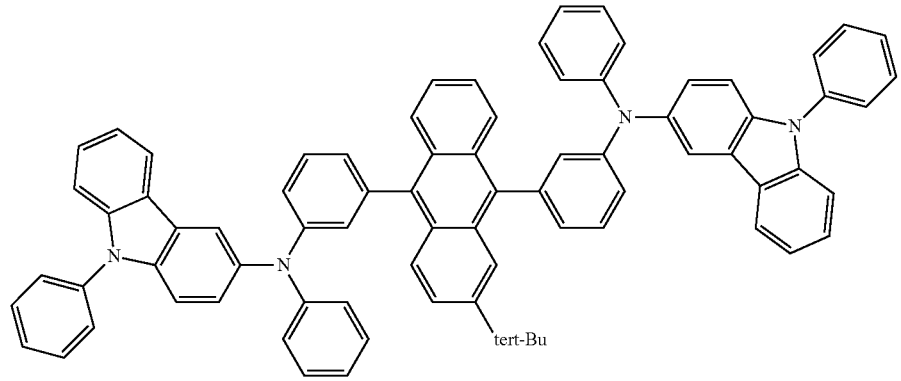
(3)

(4)
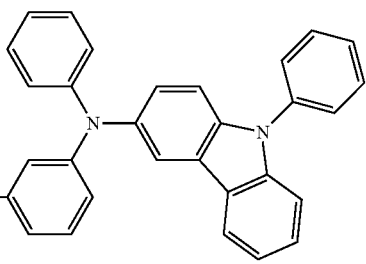
(5)
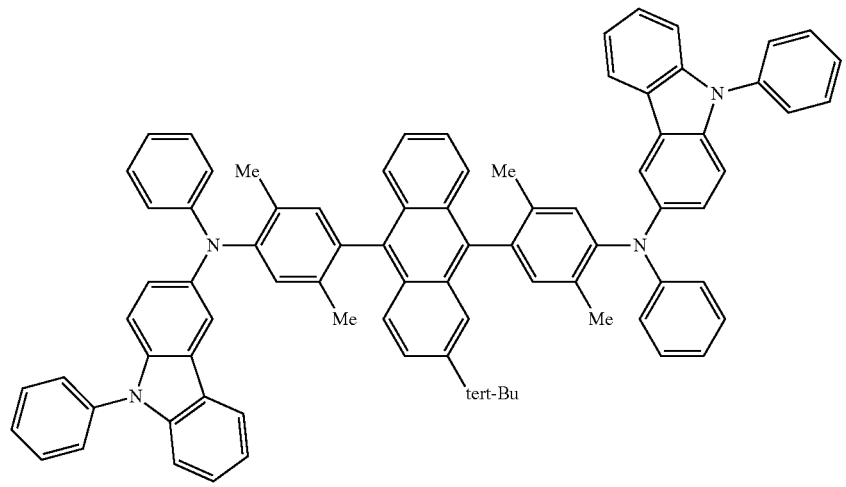
(6)
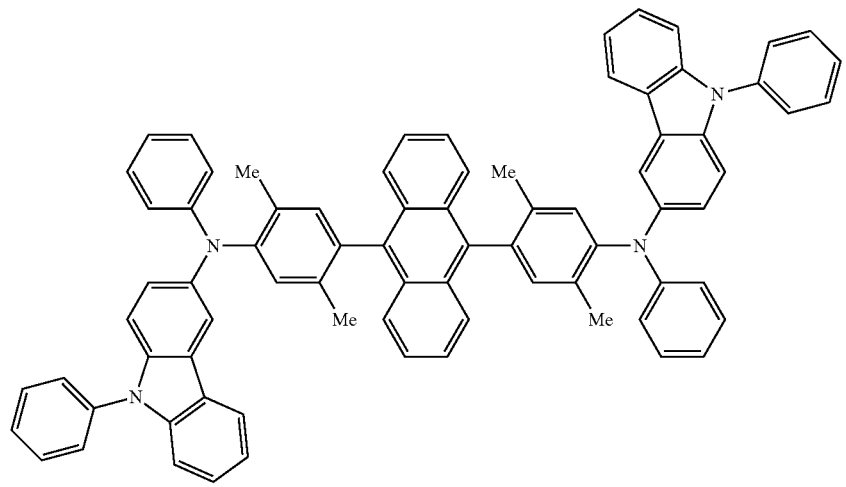

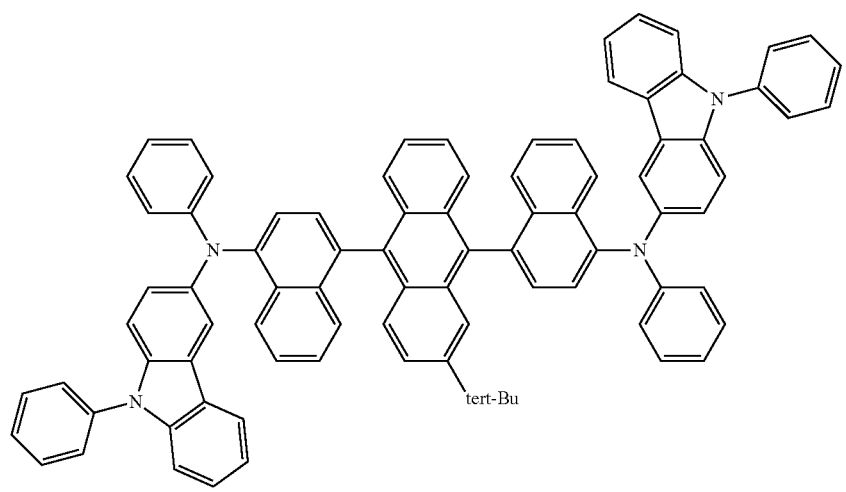
(7)
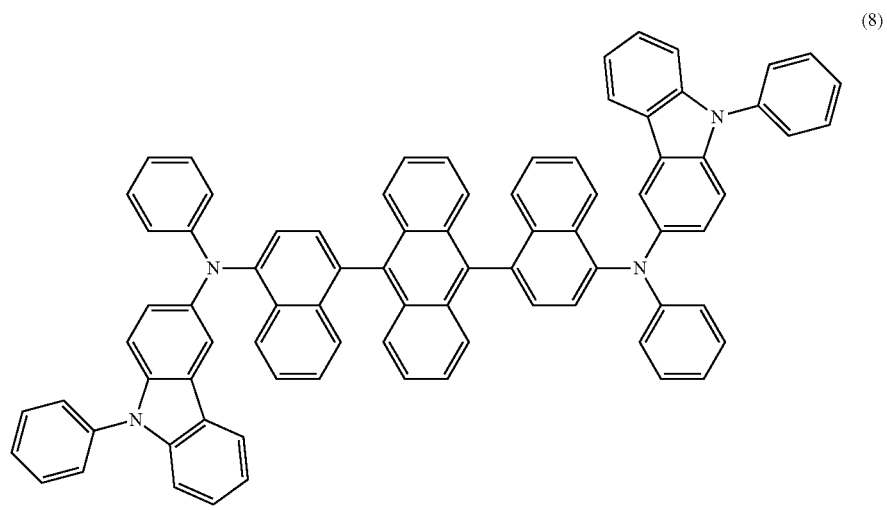
(8)
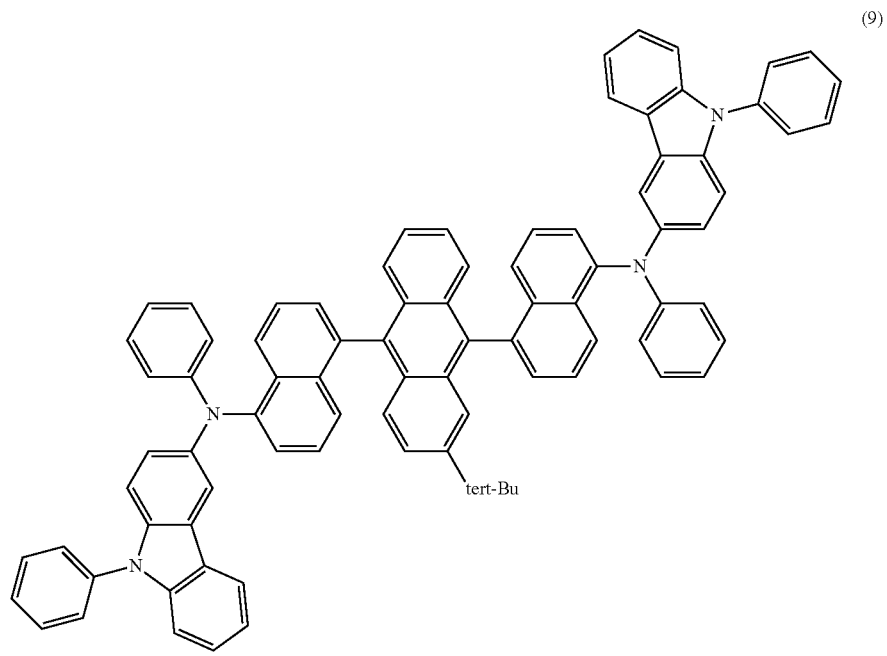
(9)

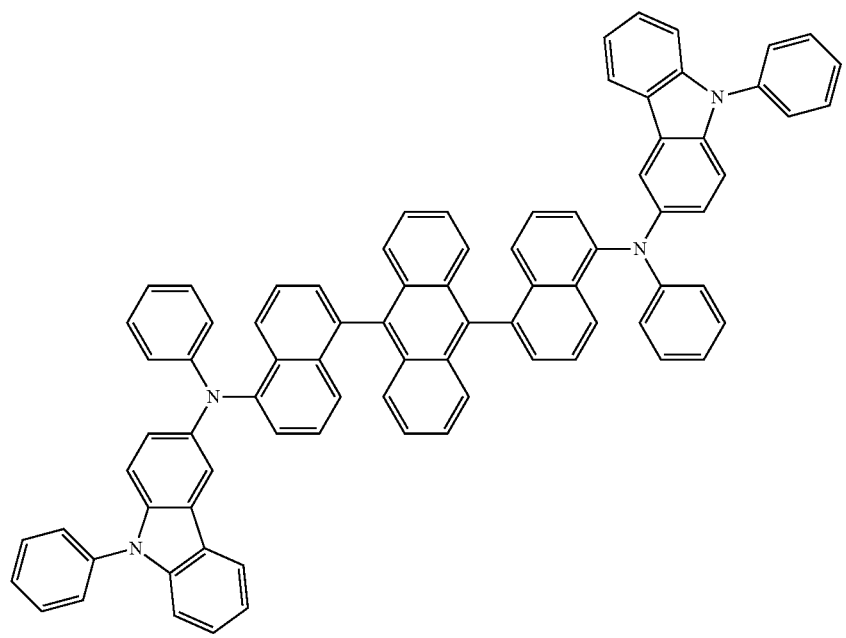
(10)
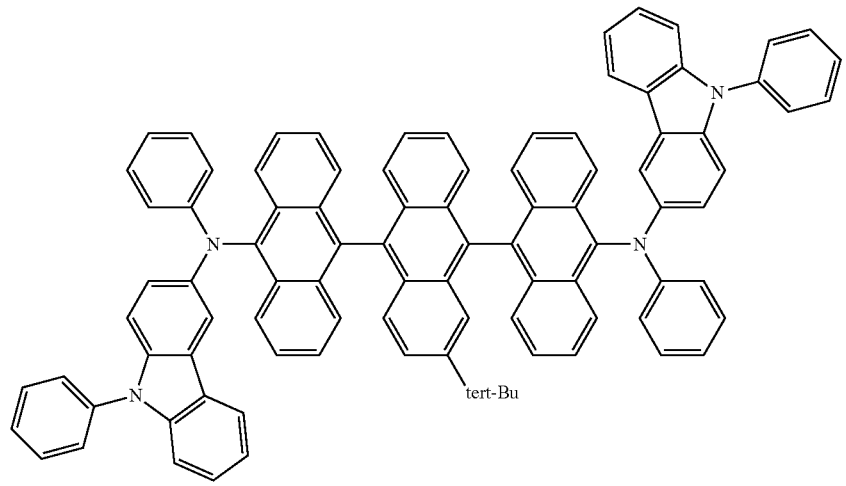
(11)
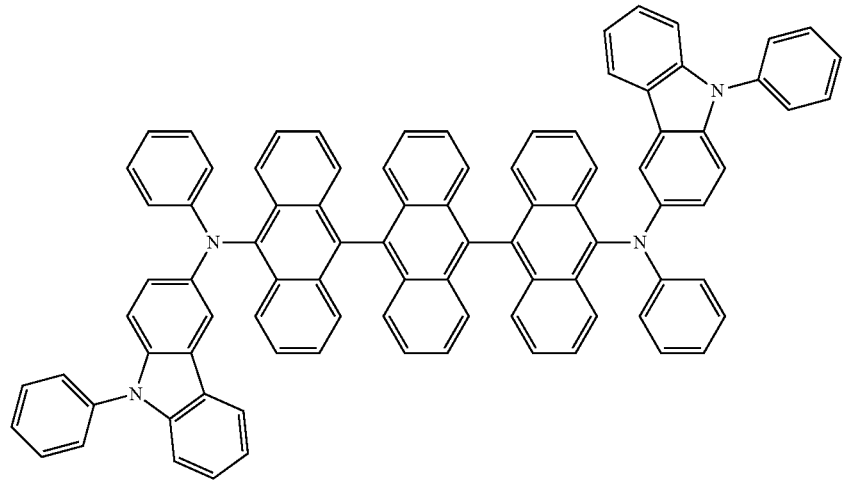
(12)

-continued
(13)
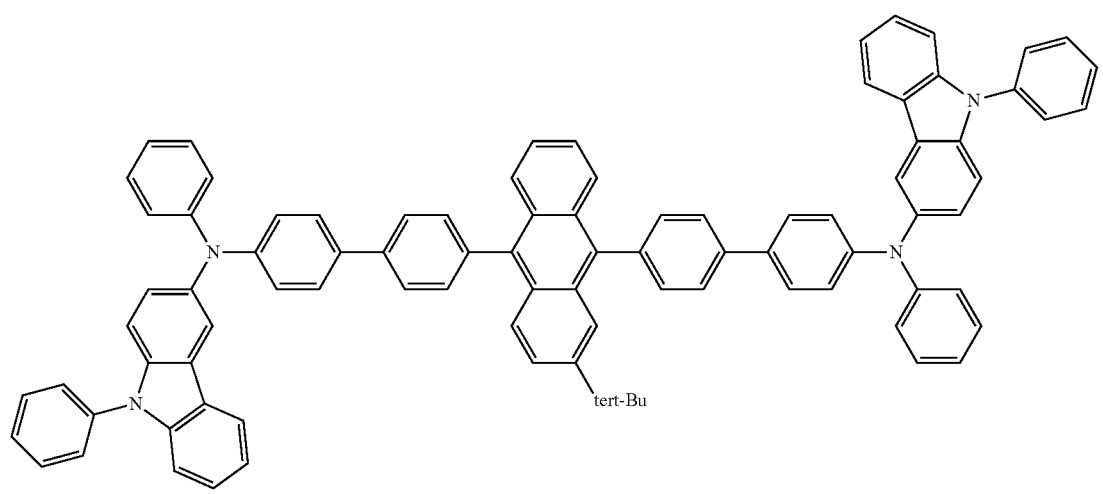
(14)
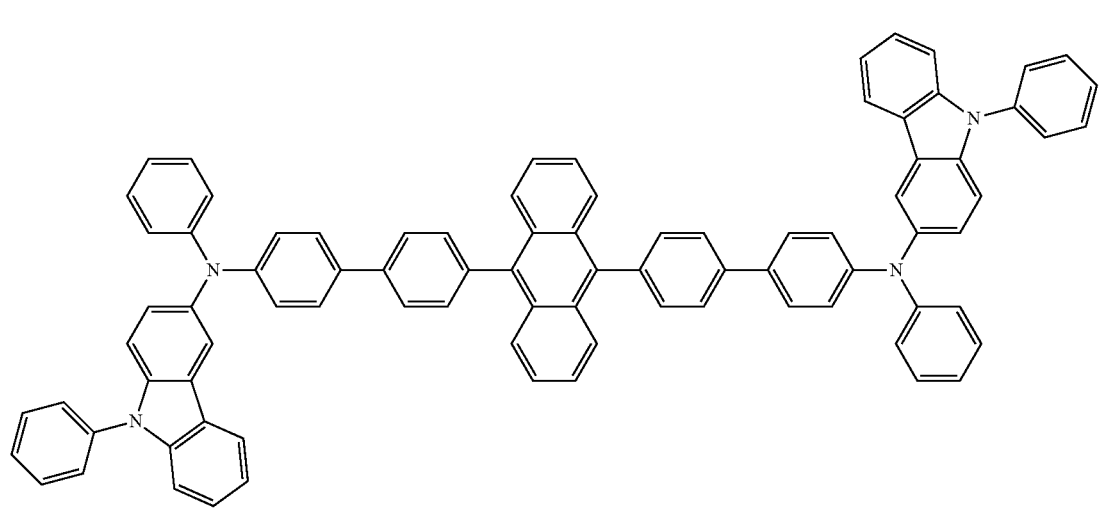
(15)
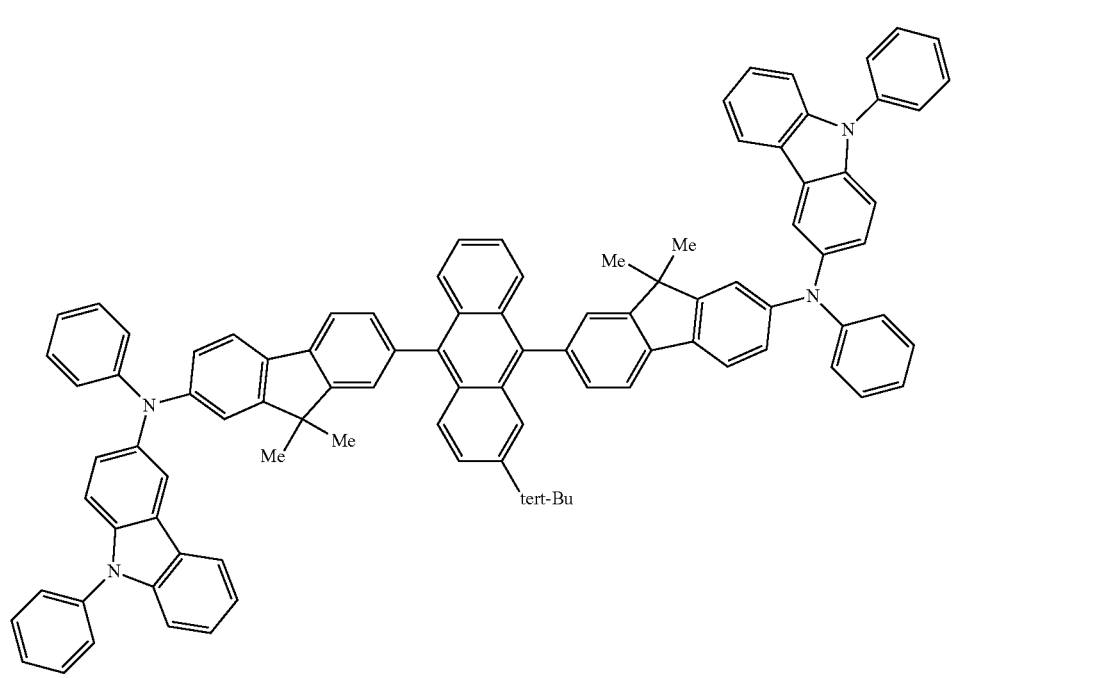

(16)
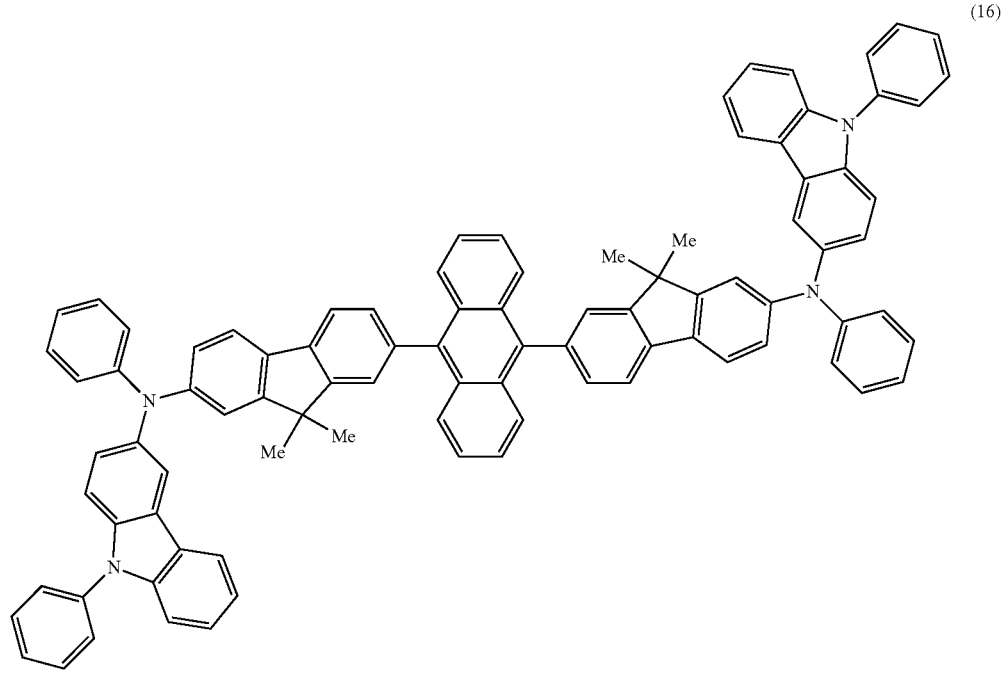
(17)
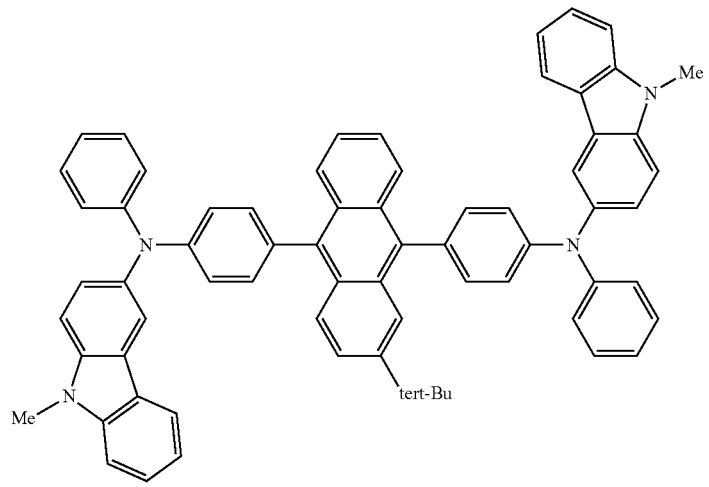
(18)
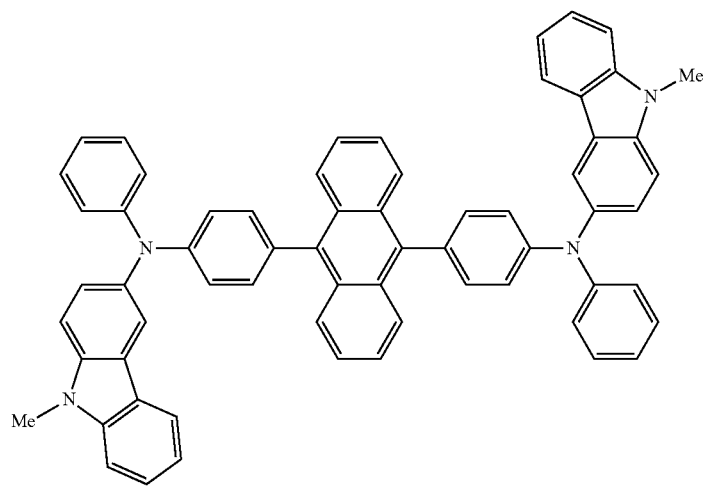

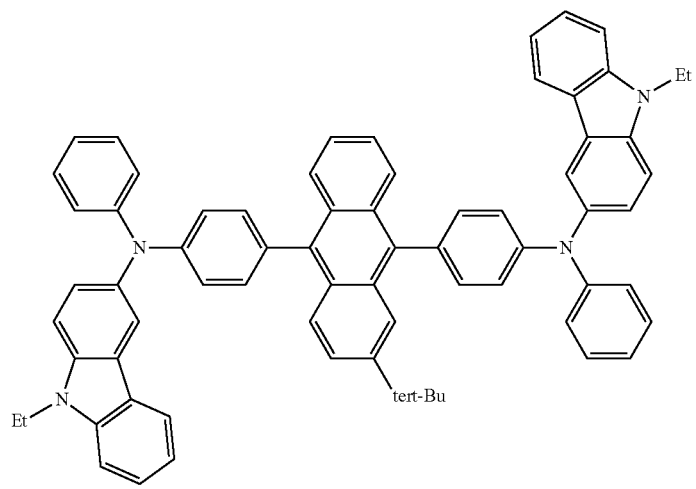
(19)
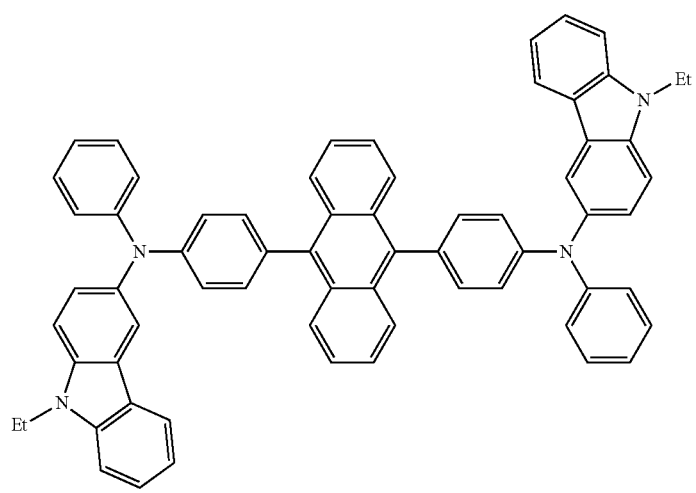
(20)
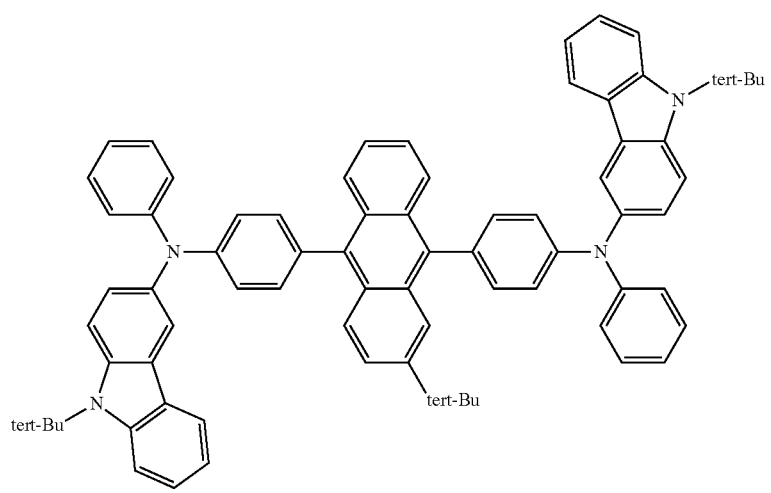
(21)

-continued
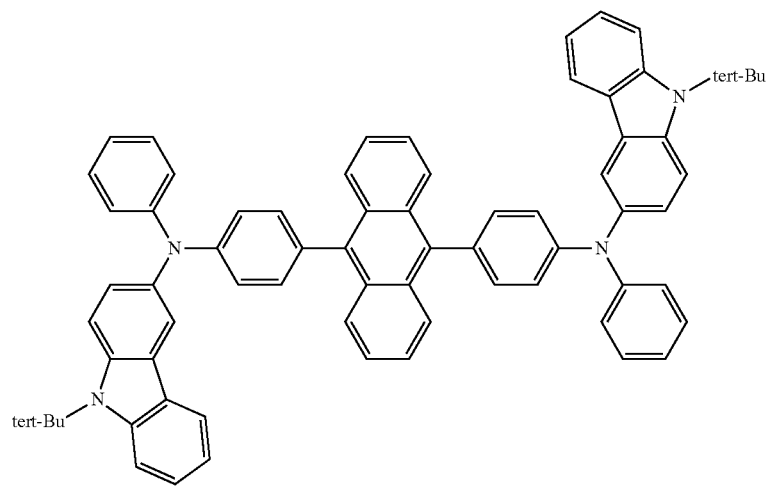
(22)
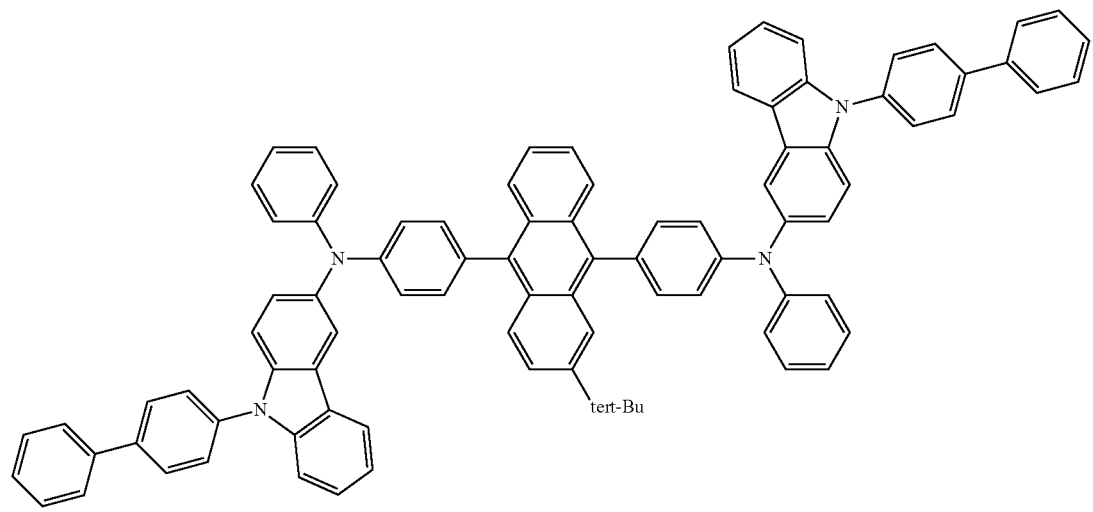
(23)
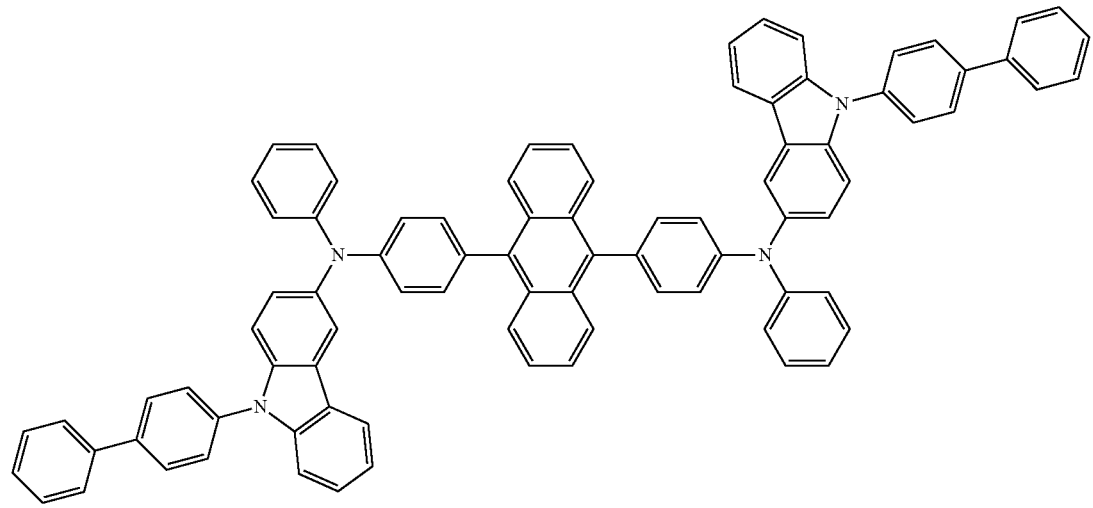
(24)

(25)
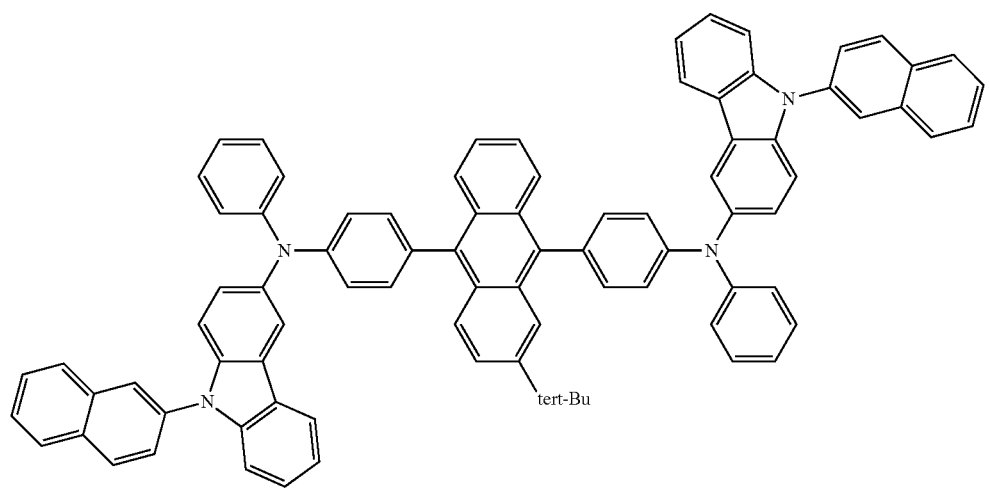
(26)
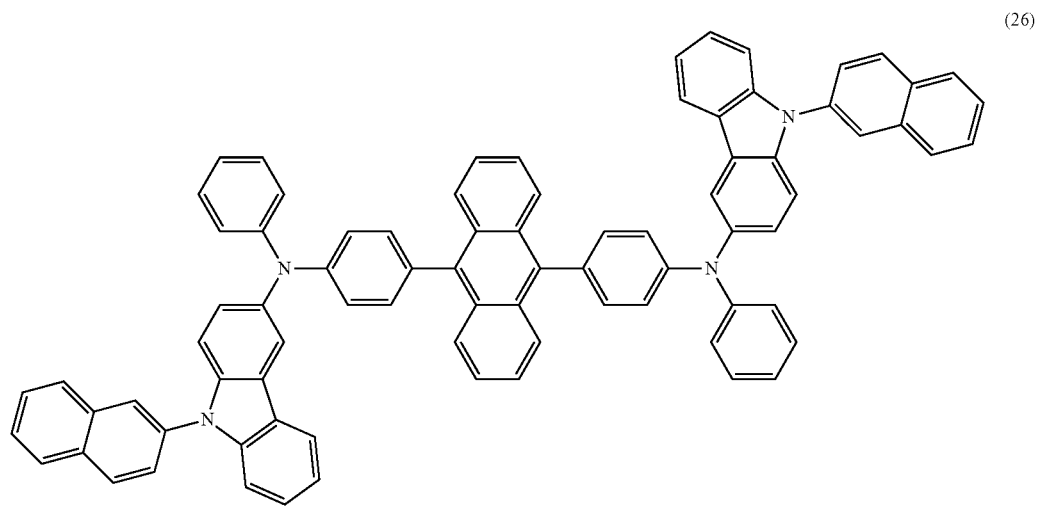
(27)
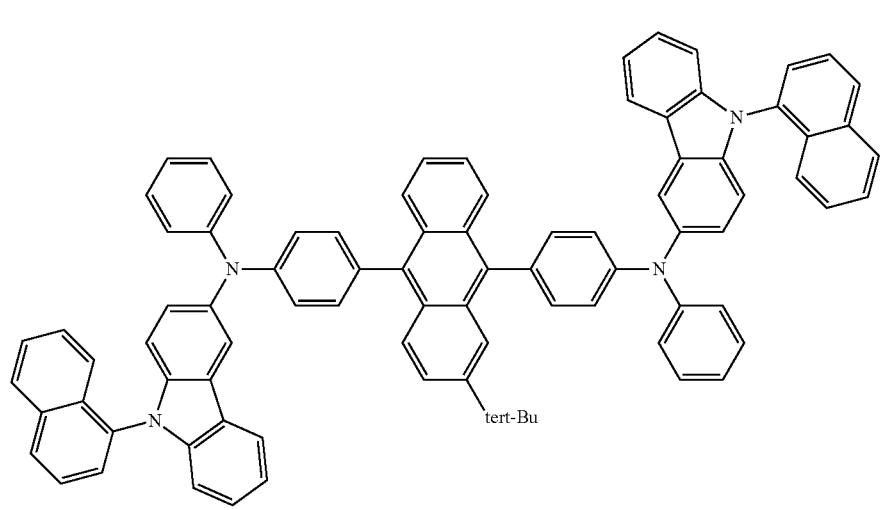

(28)
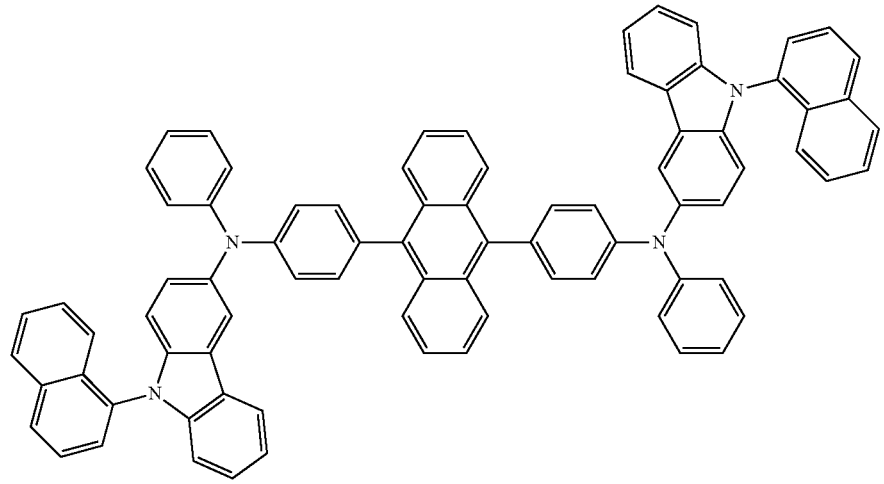
(29)
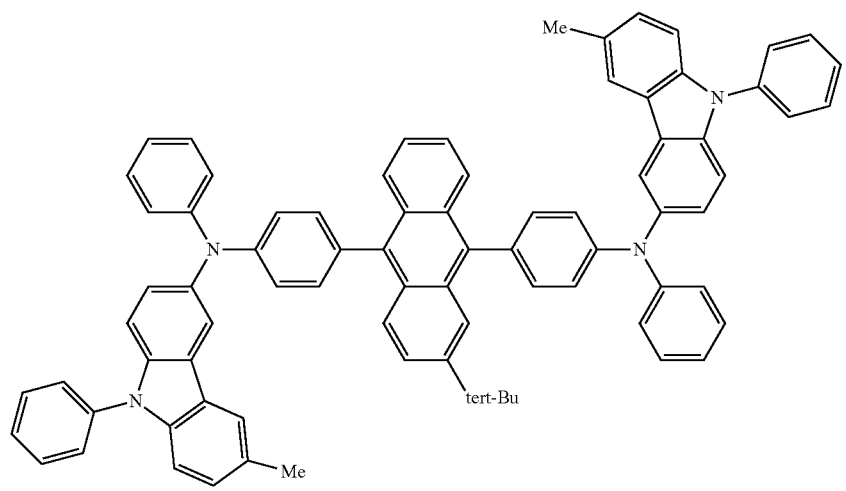
(30)
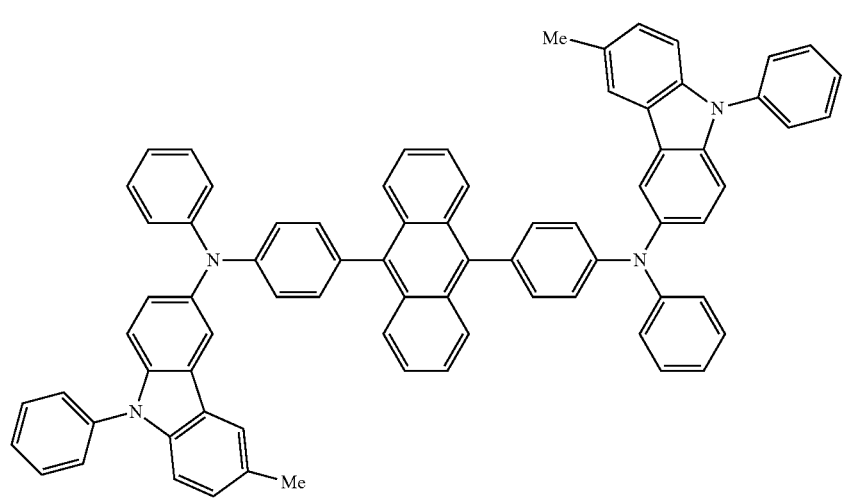

-continued
(31)
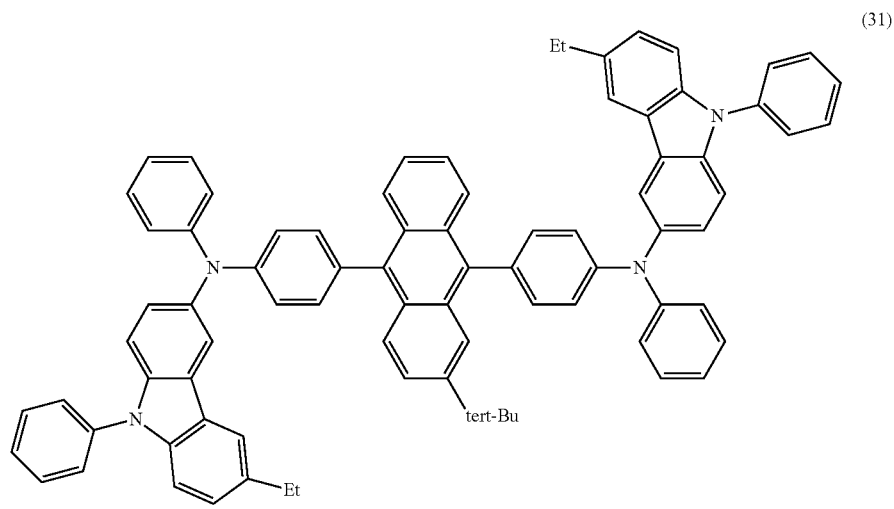
(32)
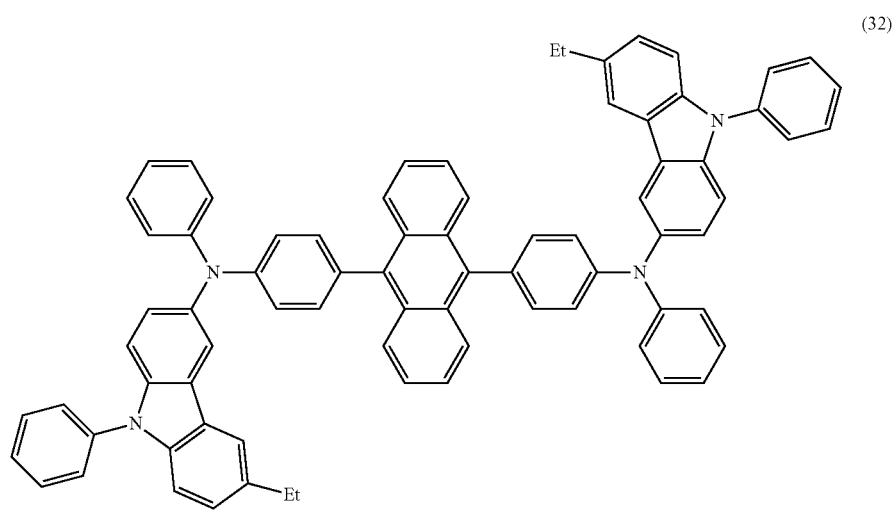
(33)
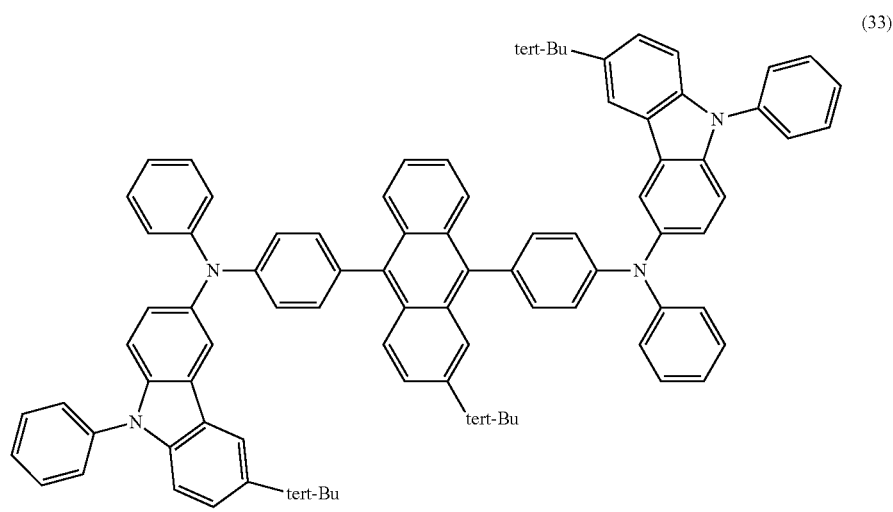

(34)
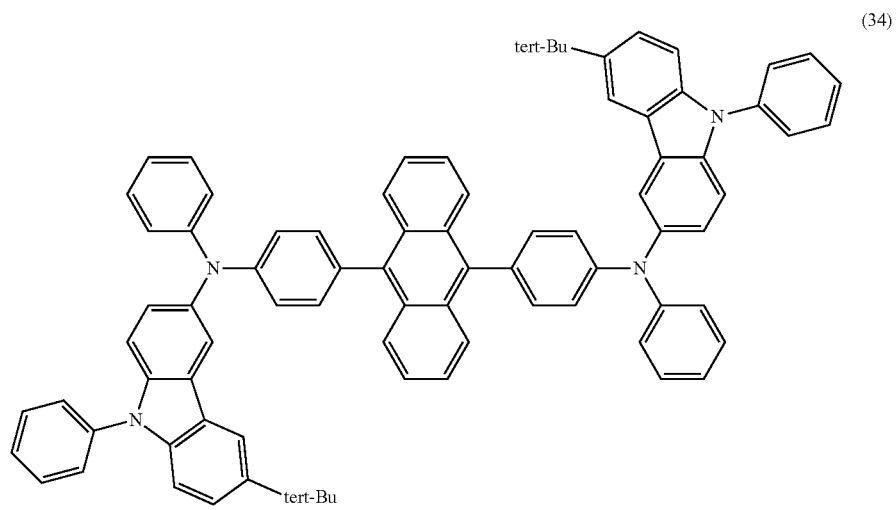
(35)
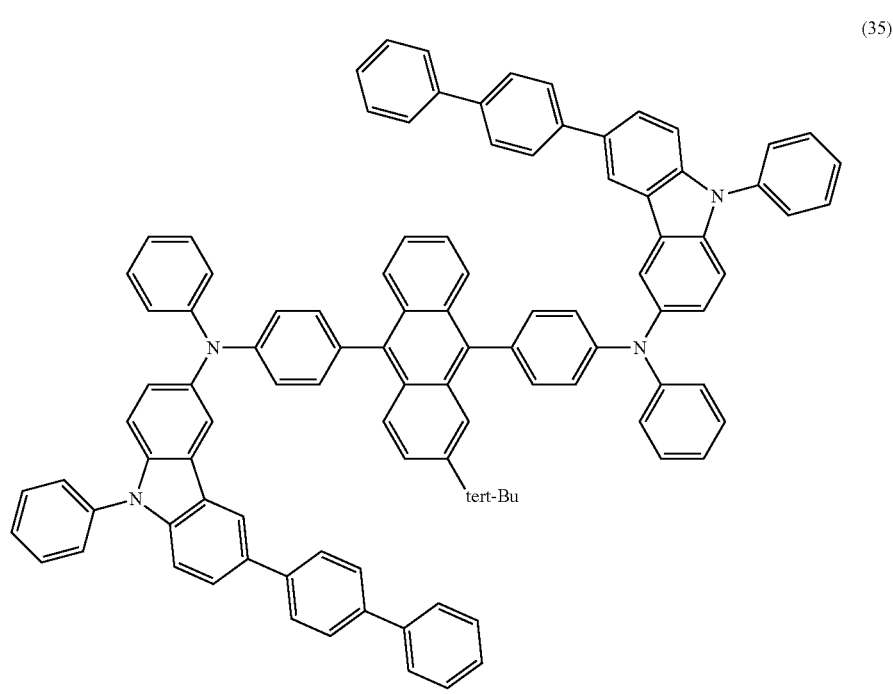

-continued
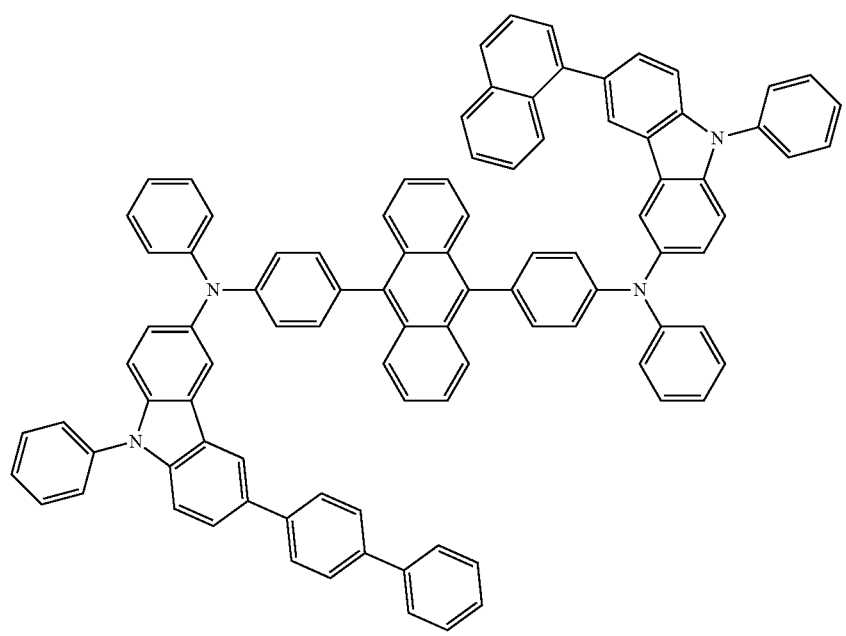
(36)
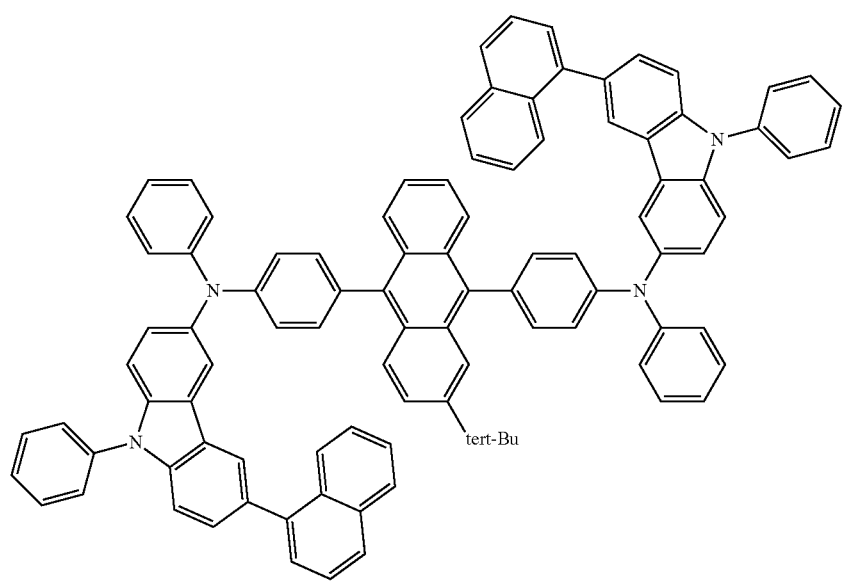
(37)

-continued
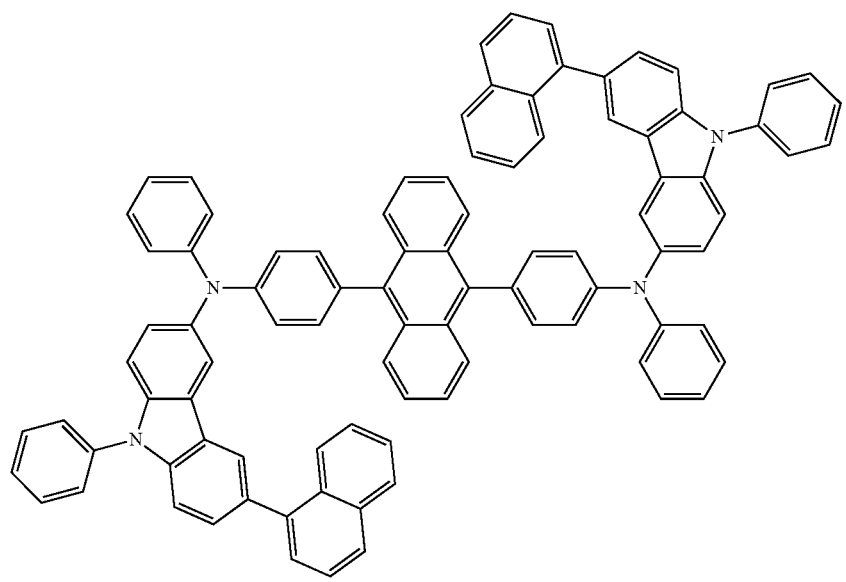
(38)
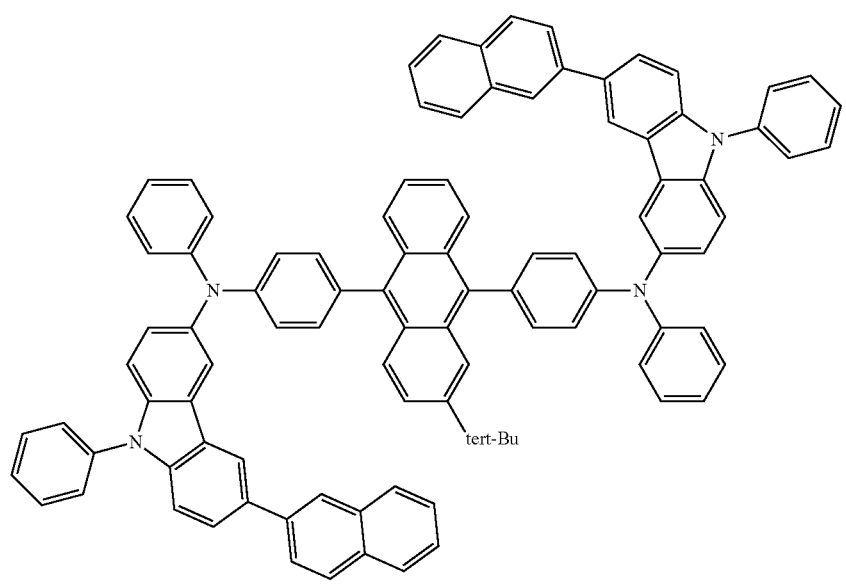
(39)

(40)

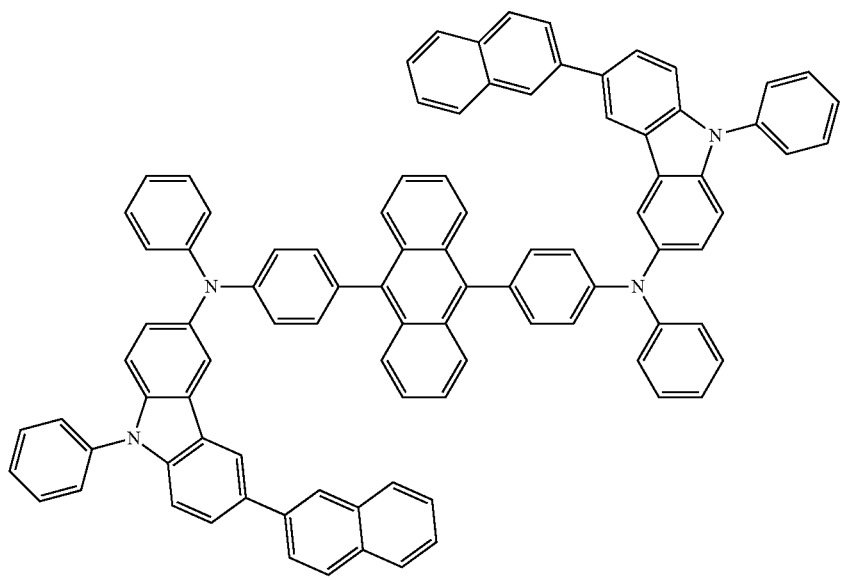

These anthracene derivatives can be obtained by, for example, performing a coupling reaction of a compound A containing anthracene such as 9,10-dibromo arylanthracene in a skeleton and a compound B containing arylamino carbazole in a skeleton, as represented by the following synthetic scheme (a-1). Further, a method for synthesizing an anthracene derivative of the present invention is not limited to the synthetic method described here and the anthracene derivative of the invention can be synthesized by other synthetic method.

(a-1)

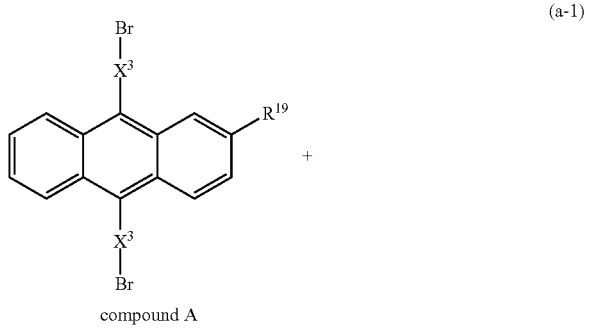

compound A

+

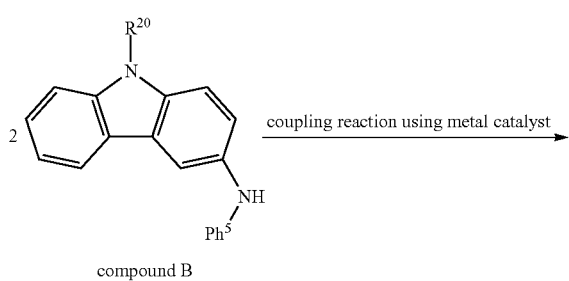

compound B coupling reaction using metal catalyst →

-continued

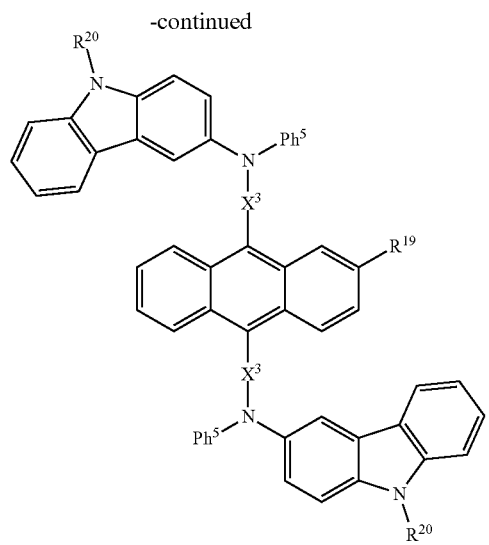

In the synthetic scheme (a-1), $R^{19}$ represents either hydrogen or tert-butyl. $R^{20}$ represents one group selected from alkyl groups having 1 to 4 carbon atoms such as hydrogen, methyl, ethyl and tert-butyl, and aryl groups having 1 to 12 carbon atoms such as phenyl, biphenyl and naphthyl. Further, the aryl group may have a substituent or no substituent. $Ph^5$ represents a phenyl group. The phenyl group may have a substituent or no substituent. $X^3$ represents an arylene group having 6 to 15 carbon atoms such as phenylene, naphthylene, anthrylene, and 9,9-dimethylfluorene-2,7-diyl.

The compound A can be obtained using dibromoarene (a compound C) and a compound containing anthraquinone in a skeleton as main raw materials, as represented by a synthetic scheme (a-2). Also, the compound B can be obtained by substituting bromo for hydrogen at a three position of a compound that contains carbazole in a skeleton, and then by performing a reaction such that an amino group is substituted for the bromo, as represented by a synthetic scheme (a-3).

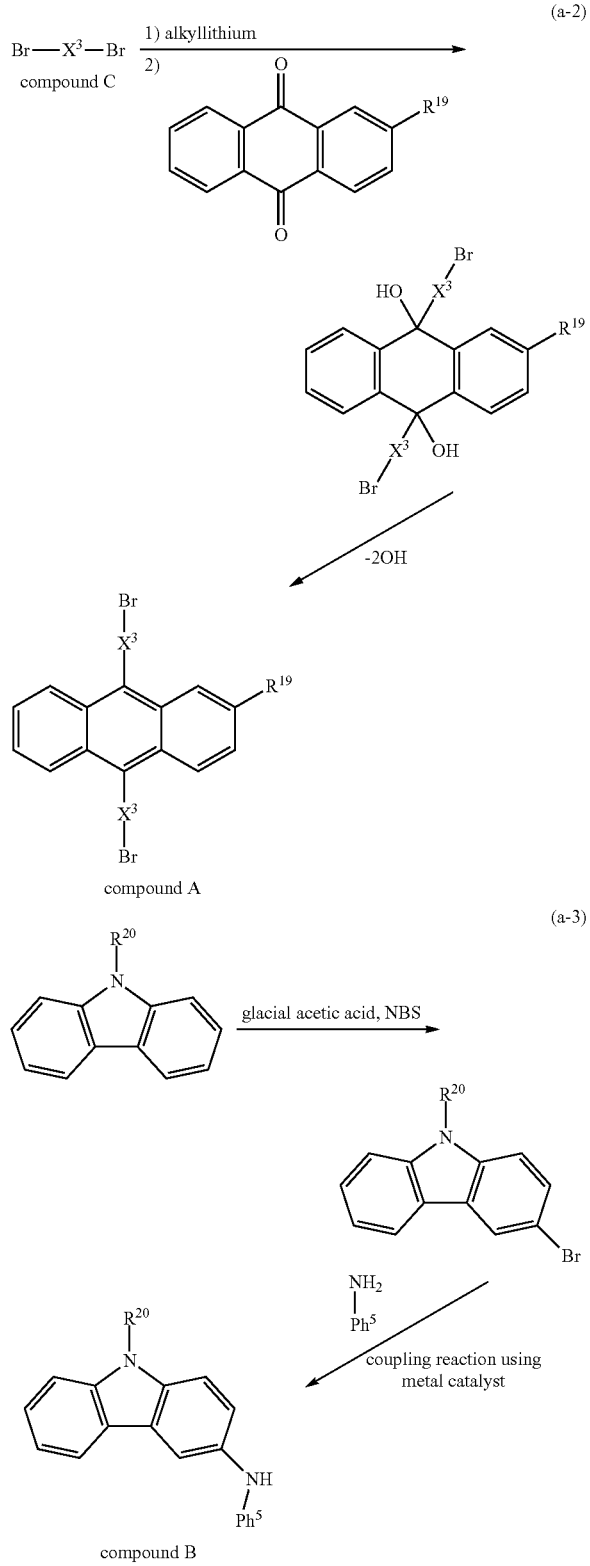

Although 9,10-bis(bromoaryl) anthracene is used as the compound A, which has an anthracene skeleton, in this embodiment mode, 9,10-bis(iodoaryl) anthracene or the like may also be used. In the synthetic scheme (a-2), the 9,10-bis(iodoaryl) anthracene can be obtained by using diiodoarene such as 1,5-diiodonaphthalene and 2,7-diiodo-9,9-dimethylfluorene as substitute for the compound C. Furthermore, the 1,5-diiodonaphthalene, the 2,7-diiodo-9,9-dimethylfluorene and the like can be obtained by performing a synthesis in the following manner. Firstly, the 1,5-diiodonaphthalene can be obtained as follows: an amino group contained in 1,5-diaminonaphthalene is changed to diazonium salt using sodium nitrite and concentrated sulfuric acid, and the diazonium salt is substituted for iodine using potassium iodide. Further, the 2,7-diiodo-9,9-dimethylfluorene can be obtained as follows: a second position and a seventh position of fluorene are iodized by using orthoperiodic acid, and then a ninth position of the iodized fluorene is dimethylized in dimethylsulfoxide (abbreviation: DMSO) by using a sodium hydroxide solution, benzyltrimethylammonium chloride, and iodomethane.

As set forth above, an anthracene derivative of the present invention is resistant to repetition of an oxidation reaction. The anthracene derivative is sometimes also resistant to repetition of a reduction reaction as well as the repetition of the oxidation reaction. In addition, the anthracene derivative of the present invention described above can emit blue light. Therefore, the anthracene derivative can be used as a light emitting substance for manufacturing a blue light emitting element. Since the anthracene derivative of the present invention as described above has a large energy gap between the HOMO level and the LUMO level, it can be used as a substance for dispersing a light emitting substance, which emits red light to blue light, or, a host material. Utilizing the anthracene derivative of the present invention as a light emitting substance or a host material makes it possible to obtain a light emitting element having less changes in a host property due to repetition of an oxidation reaction, wherein the increase in driving voltage with an accumulation of light emitting time and the like are reduced.

[Embodiment Mode 2]

One mode of a light emitting element using an anthracene derivative of the present invention as a light emitting substance will be described with reference to FIG. 1.

A light emitting element having a light emitting layer 113 between a first electrode 101 and a second electrode 102 is shown in FIG. 1. The light emitting layer 113 contains an anthracene derivative of the present invention represented by any one of the general formulas (1) to (8) and the structural formulas (1) to (40).

In such a light emitting element, a hole injected from the first electrode 101 and an electron injected from the second electrode 102 are recombined at the light emitting layer 113, which makes the anthracene derivative of the present invention excited. The anthracene derivative of the present invention in the excited state emits light upon returning to a ground state. Thus, the anthracene derivative of the present invention serves as a light emitting substance.

The light emitting layer 113 is preferably a layer in which an anthracene derivative of the present invention represented by any one of the general formulas (1) to (8) and the structural formulas (1) to (40) is dispersed in a substance having a larger energy gap than that of the anthracene derivative of the present invention. This can prevent light emitted from the anthracene derivative of the present invention from going out due to the concentration. Further, the energy gap indicates an energy gap between the LUMO level and the HOMO level.

Although a substance used for dispersing the anthracene derivative of the present invention is not particularly limited, a metal complex such as bis[2-(2-hydroxyphenyl)pyridinato] zinc (abbreviation: Znpp$_2$) and bis[2-(2-hydroxyphenyl) benzoxazolato] zinc (abbreviation: Zn(BOX)$_2$), and the like are preferable, in addition to an anthracene derivative such as 2-tert-butyl-9,10-di(2-naphthyl) anthracene (abbreviation: t-BuDNA) and a carbazole derivative such as 4,4'-di(N-carbazolyl) biphenyl (abbreviation: CBP). One or more substances may be selected from the above mentioned substances and mixed in an anthracene derivative of the present invention so as to disperse the anthracene derivative of the invention in the one or more substances. Such a layer in which a plurality of compounds are mixed can be formed by using co-evaporation. The co-evaporation is an evaporation method in which raw materials are respectively vaporized from a plurality of evaporation sources provided in one processing chamber and the vaporized raw materials are mixed in a gaseous state so as to be deposited over an object material.

Also, the first electrode 101 and the second electrode 102 are not particularly limited. They can be formed by using gold (Au), platinum (Pt), nickel (Ni), tungsten (W), chromium (Cr), molybdenum (Mo), iron (Fe), cobalt (Co), copper (Cu), palladium (Pd) and the like, in addition to indium tin oxide (ITO), indium tin oxide containing silicon oxide and indium oxide containing 2 to 20 wt % zinc oxide. The first electrode 101 can also be formed using an alloy of magnesium and silver, an alloy of aluminum and lithium or the like, in addition to aluminum. Further, a method for forming the first electrode 101 and the second electrode 102 is not particularly limited. For example, they can be formed by using sputtering, evaporation or the like. To emit light to an external portion, one or both of the first electrode 101 and the second electrode 102 is/are preferably formed by using indium tin oxide or the like, or using silver, aluminum or the like to have a thickness of several nm to several tens nm such that visible light is transmitted therethrough.

As shown in FIG. 1, a hole transporting layer 112 may be provided between the first electrode 101 and the light emitting layer 113. The hole transporting layer is a layer having a function of transporting holes injected from the first electrode 101 to the light emitting layer 113. Thus, providing the hole transporting layer 112 makes it possible to increase a distance between the first electrode 101 and the light emitting layer 113. As a result, it is possible to prevent light emission from going out due to a metal contained in the first electrode 101 and the like. The hole transporting layer is preferably formed using a substance having a strong hole transporting property. In particular, a substance having hole mobility with $1 \times 10^{-6}$ cm$^2$/Vs or more is preferably used for forming the hole transporting layer. Further, the substance having the strong hole transporting property is a substance of which hole mobility is stronger than electron mobility and a ratio of the hole mobility to the electron mobility (i.e., the hole mobility/the electron mobility) is 100 or more. As a specific example of a substance that can be used for forming the hole transporting layer 112, 4,4'-bis[N-(1-naphthyl)-N-phenylamino] biphenyl (abbreviation: NPB), 4,4'-bis[N-(3-methylphenyl)-N-phenylamine] biphenyl (abbreviation: TPD), 4,4',4''-tris(N,N-diphenylamino)triphenylamine (abbreviation: TDATA), 4,4',4''-tris[N-(3-methylphenyl)-N-phenylamino] triphenylamine (abbreviation: MTDATA), 4,4'-bis{N-[4-(N,N-di-m-tolylamino) phenyl]-N-phenylamino} biphenyl (abbreviation: DNTPD), 1,3,5-tris[N,N-di (m-tolyl)amino] benzene (abbreviation: m-MTDAB), 4,4', 4''-tris(N-carbazolyl) triphenylamine (abbreviation: TCTA), phthalocyanine (abbreviation: H$_2$Pc), copper phthalocyanine (abbreviation: CuPc), vanadyl phthalocyanine (abbreviation: VOPc), and the like can be given. Further, the hole transporting layer 112 may be a layer having a multilayer structure that is formed by combining two or more layers including the above mentioned substances.

Also, as shown in FIG. 1, an electron transporting layer 114 may be provided between the second electrode 102 and the light emitting layer 113. The electron transporting layer is a layer having a function of transporting electrons injected from the second electrode 102 to the light emitting layer 113. Thus, providing the electron transporting layer 114 makes it possible to increase a distance between the second electrode 102 and the light emitting layer 113. As a result, it is possible to prevent light emission from going out due to a metal contained in the second electrode 102 and the like. The electron transporting layer is preferably formed using a substance having a strong electron transporting property. In particular, a substance having electron mobility with $1 \times 10^{-6}$ cm$^2$/Vs or more is preferably used for forming the electron transporting layer. Further, the substance having the strong electron transporting property is a substance of which electron mobility is stronger than hole mobility and a ratio of the electron mobility to the hole mobility (i.e., the electron mobility/the hole mobility) is 100 or more. As a specific example of a substance that can be used for forming the election transporting layer 114, a metal complex such as tris(8-quinolinolato) aluminum (abbreviation: Alq$_3$), tris(4-methyl-8-quinolinolato) aluminum (abbreviation: Almq$_3$), bis(10-hydroxybenzo[h]-quinolinato) beryllium (abbreviation: BeBq$_2$), bis(2-methyl-8-quinolinolato)-4-phenylphenolate-aluminum (abbreviation: BAlq), bis[2-(2-hydroxyphenyl) benzoxazolato] zinc (abbreviation: Zn(BOX)$_2$), and bis[2-(2-hydroxyphenyl) benzothiazolato] zinc (abbreviation: Zn(BTZ)$_2$) can be given. In addition, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl] benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-thiazole (abbreviation: p-EtTAZ), bathophenanthroline (abbreviation: BPhen), bathocuproin (abbreviation: BCP), 4,4-bis(5-methylbenzoxazole-2-yl) stilbene (abbreviation: BzOs), and the like can be given. Further, the electron transporting layer 114 may be a layer having a multilayer structure that is formed by combining two or more layers including the above mentioned substances.

Each of the hole transporting layer 112 and the electron transporting layer 114 may be formed using a bipolar substance, in addition to the above mentioned substances. The bipolar substance is a substance of which when comparing electron mobility and hole mobility, a ratio of the mobility of one carrier to the mobility of the other carrier is 100 or less, and preferably, 10 or less. As the bipolar substance, for example, 2,3-bis(4-diphenylaminophenyl) quinoxaline (abbreviation: TPAQn) and the like can be given. Among bipolar substances, in particular, a substance having hole and electron mobility with $1 \times 10^{-6}$ cm$^2$/Vs or more is preferably used. Also, the hole transporting layer 112 and the electron transporting layer 114 may be formed using the same bipolar substance.

As shown in FIG. 1, a hole injecting layer 111 may also be provided between the first electrode 101 and the hole transporting layer 112. The hole injecting layer 111 is a layer having a function of helping injection of holes to the hole transporting layer 112 from the first electrode 101. Providing the hole injecting layer 111 makes it possible to reduce the difference in ionization potential between the first electrode 101 and the hole transporting layer 112 so that holes are easily injected. The hole injecting layer 111 is preferably formed by using a substance of which an ionization potential is lower than that of a substance of the hole transporting layer 112 and higher than that of a substance used for forming the first electrode 101, or a substance in which an energy band is bent when it is provided as a thin film with a thickness of 1 to 2 nm between the hole transporting layer 112 and the first electrode 101. As a specific example of a substance that can be used for forming the hole injecting layer 111, a phthalocyanine compound such as phthalocyanine (abbreviation: $H_2Pc$) and copper phthalocyanine (abbreviation: CuPc), a polymer such as a poly(ethylenedioxythiophene)/poly(styrenesulfonate) aqueous solution (abbreviation: PEDOT/PSS), and the like can be given. That is, the hole injecting layer 111 can be formed by selecting a substance by which an ionization potential in the hole injecting layer 111 is relatively smaller than an ionization potential of the hole transporting layer 112 from substances having hole transporting properties. Further, when proving the hole injecting layer 111, the first electrode 101 is preferably formed using a substance having a high work function such as indium tin oxide.

An electron injecting layer 115 may also be provided between the second electrode 102 and the electron transporting layer 114 as shown in FIG. 1. The electron injecting layer 115 is a layer having a function of helping injection of electrons to the electron transporting layer 114 from the second electrode 102. Providing the electron injecting layer 115 makes it possible to reduce the difference in electron affinity between the second electrode 102 and the electron transporting layer 114 so that electrons are easily injected. The electron injecting layer 115 is preferably formed using a substance of which an electron affinity is higher than that of a substance included in the electron transporting layer 114 and lower than that of a substance included in the second electrode 102, or a substance of which an energy band is bent when it is provided as a thin film with a thickness of 1 to 2 nm between the electron transporting layer 114 and the second electrode 102. As a specific example of a substance that can be used for forming the electron injecting layer 115, inorganic materials such as alkali metal, alkali earth metal, fluoride of alkali metal, fluoride of alkali earth metal, alkali metal oxide, and alkali earth metal oxide can be given. In addition to the inorganic materials, among the substances, which can be used for forming the electron transporting layer 114, such as BPhen, BCP, p-EtTAZ, TAZ and BzOs, a substance having higher electron affinity than that of a substance used for forming the electron transporting layer 114 can be selected to be used to form the electron injecting layer 115. That is, a substance by which an electron affinity of the electron injecting layer 115 is relatively higher than that of the electron transporting layer 114, is selected from substances having electron transporting properties so that the electron injecting layer 115 can be formed. Further, when providing the electron injecting layer 115, the first electrode 101 is preferably formed using a substance having a low work function such as aluminum.

In the light emitting element of the present invention as described above, the hole injecting layer 111, the hole transporting layer 112, the light emitting layer 113, the electron transporting layer 114, and the electron injecting layer 115 may be formed by using any method such as evaporation, ink-jet, and a coating method, respectively. Further, the first electrode 101 and the second electrode 102 may be formed by using any method such as sputtering and evaporation.

Moreover, a hole generating layer may be provided as a substitute for the hole injecting layer 111. Alternatively, an electron generating layer may be provided as a substitute for the electron injecting layer 115.

The hole generating layer is a layer generating holes. The hole generating layer can be formed by mixing a substance of which hole mobility is stronger than electron mobility and a substance exhibiting an electron accepting property with respect to the substance of which the hole mobility is stronger than the electron mobility. The hole generating layer can also be formed by mixing at least one substance selected from bipolar substances and a substance exhibiting an electron accepting property with respect to the bipolar substance. As the substance of which the hole mobility is stronger than the electron mobility, the same substance as a substance that can be used for forming the hole transporting layer 112 can be used. As the bipolar substance, a bipolar substance such as TPAQn can be used. Also, among substances having stronger hole mobility than electron mobility and bipolar substances, in particular, a substance containing triphenylamine in skeleton is preferably used. Using the substance containing triphenylamine in the skeleton makes it possible to generate holes more easily. As the substance exhibiting the electron accepting property, metal oxide such as molybdenum oxide, vanadium oxide, ruthenium oxide, and rhenium oxide is preferably used.

Further, the electron generating layer is a layer generating electrons. The electron generating layer can be formed by mixing a substance of which electron mobility is stronger than hole mobility and a substance exhibiting an electron donating property with respect to the substance of which the electron mobility is stronger than the hole mobility. The electron generating layer can also be formed by mixing at least one substance selected from bipolar substances and a substance exhibiting an electron donating property with respect to the bipolar substance. Here, as the substance of which the electron mobility is stronger than the hole mobility, the same substance as a substance that can be used for forming the electron transporting layer 114 can be used. As the bipolar substance, the above mentioned bipolar substances such as TPAQn can be used. As the substance exhibiting the electron donating property, a substance selected from alkali metal and alkali earth metal can be used. Specifically, at least one substance selected from lithium oxide ($Li_2O$), calcium oxide (CaO), natrium oxide ($Na_2O$), kalium oxide ($K_2O$), and magnesium oxide (MgO) can be used as the substance exhibiting the electron donating property. In addition, alkali metal fluoride or alkali earth metal fluoride, and specifically, at least one substance selected from lithium fluoride (LiF), cesium fluoride (CsF) and calcium fluoride ($CaF_2$) can be used as the substance exhibiting the electron donating property. Further, alkali metal nitride, alkali earth metal nitride, and the like, or specifically, at least one substance selected from calcium nitride, magnesium nitride and the like can be used as the substance exhibiting the electron donating property.

Since the light emitting element of the present invention having the above described structure uses an anthracene derivative of the present invention, there are few changes in a characteristic of the light emitting element in accordance with changes in a property of a light emitting substance due to repetition of an oxidation reaction. As a result, the light emitting element can emit light stably for a long time. Moreover; since the light emitting element of the present invention comprising the above described structure uses an anthracene derivative of the present invention, it can emit light efficiently.

[Embodiment Mode 3]

When an anthracene derivative of the present invention is included in a light emitting layer along with a light emitting substance, the anthracene derivative can be used as a substance for dispersing the light emitting substance, or, a host material. In Embodiment Mode 3, a mode of a light emitting element using an anthracene derivative of the present invention as a host material will be described with reference to FIG. 2.

Figure 2:
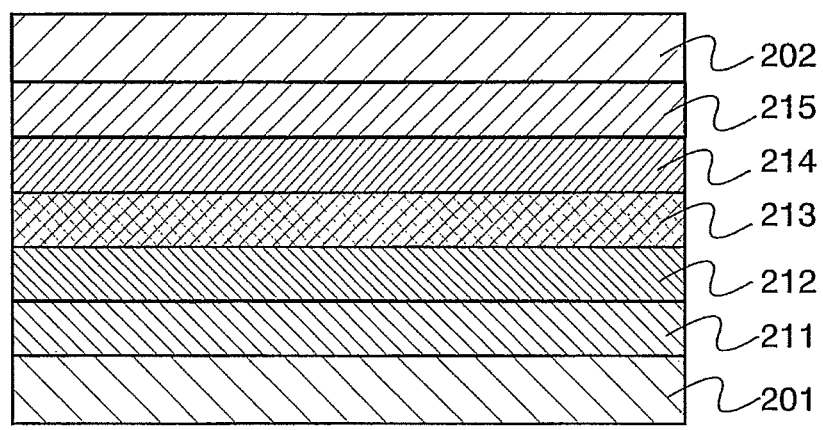
FIG. 2 is a cross sectional view explaining a light emitting element of the present invention.

FIG. 2 shows a light emitting element having a light emitting layer 213 between a first electrode 201 and a second electrode 202. A hole injecting layer 211 and a hole transporting layer 212 are provided between the first electrode 201 and the light emitting layer 213 while an electron transporting layer 214 and an electron injecting layer 215 are provided between the second electrode 202 and the light emitting layer 213. Further, a laminated structure of the light emitting element is not particularly limited. An operator of the present invention may arbitrarily determine whether the hole injecting layer 211, the hole transporting layer 212, the electron transporting layer 214, the electron injecting layer 215 and other layer other than these layers are provided or not provided. Furthermore, the hole injecting layer 211, the hole transporting layer 212, the electron transporting layer 214 and the electron injecting layer 215 may be the same as the hole injecting layer 111, the hole transporting layer 112, the electron transporting layer 114 and the electron injecting layer 115 described in Embodiment Mode 2, and therefore these layers will not be further described in this embodiment mode. Similarly, since the first electrode 201 and the second electrode 202 may be the same as the first electrode 101 and the second electrode 102 described in Embodiment Mode 1, respectively, they will not be further described here.

In the light emitting element of this embodiment mode, the light emitting layer 213 contains an anthracene derivative of the present invention and a light emitting substance having a spectrum peak in a range of 450 to 700 nm, and preferably 480 nm to 600 nm. Specifically, the light emitting substance is dispersed in a layer formed using the anthracene derivative of the present invention. By using a combination of such a substance and the anthracene derivative of the present invention, a light emitting element in which light from a host material is difficult to be mixed and light caused by the light emitting substance can be selectively emitted, can be obtained.

Moreover, the anthracene derivative of the present invention is resistant to repetition of an oxidation reaction. Furthermore, the anthracene derivative of the present invention is sometimes resistant to repetition of a reduction reaction, as well as the repetition of the oxidation reaction. Therefore, in the case of a light emitting element in which a host material is excited and light is emitted by moving the thus caused excited energy to a light emitting substance, there are few changes in a characteristic of the host material due to repetition of an oxidation reaction, and the increase in driving voltage with accumulation of light emitting time and the like can be reduced.

[Embodiment Mode 4]

Since the light emitting elements of the present invention described in Embodiment Modes 2 and 3 are resistant to repetition of an oxidation reaction (which are sometimes also resistant to repetition of a reduction reaction) and can emit light stably for a long time, a light emitting device that can display favorable images for a long time can be obtained by using the light emitting elements of the present invention.

In this embodiment mode, circuit structures and driving methods of a light emitting device having a display function will be described with reference to FIGS. 3, 4, 5 and 6.

Figure 3:
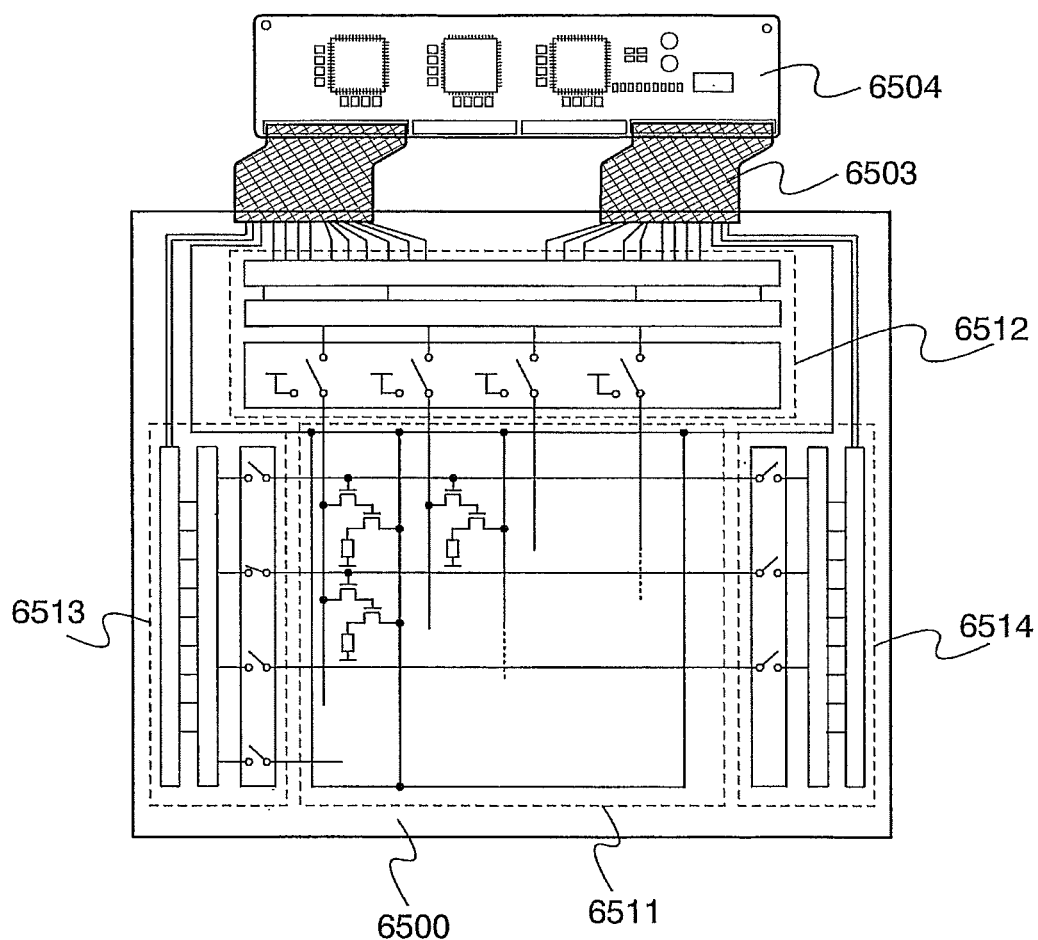
FIG. 3 is a top view explaining a light emitting device to which the present invention is applied.

FIG. 3 is a schematic top view of a light emitting device to which the present invention is applied. In FIG. 3, a pixel portion 6511, a source signal line driver circuit 6512, a writing gate signal line driver circuit 6513 and an erasing gate signal line driver circuit 6514 are provided over a substrate 6500. The source signal line driver circuit 6512, the writing gate signal line driver circuit 6513 and the erasing gate signal line driver circuit 6514 are respectively connected to FPCs (flexible printed circuits) 6503, which are external input terminals, through wiring groups. The source signal line driver circuit 6512, the writing gate signal line driver circuit 6513 and the erasing gate signal line driver circuit 6514 receive video signals, clock signals, start signals, reset signals and the like from the FPCs 6503, respectively. The FPCs 6503 are attached with printed wiring boards (PWBs) 6504. Further, a driver circuit portion is not necessary to be formed over the same substrate as the pixel portion 6511. For example, the driver circuit portion may be provided outside of the substrate by utilizing a TCP in which an IC chip is mounted over an FPC having a wiring pattern, or the like.

A plurality of source signal lines extending in columns are aligned in rows in the pixel portion 6511. Also, power supply lines are aligned in rows. A plurality of gate signal lines extending in rows are aligned in columns in the pixel portion 6511. In addition, a plurality of circuits each including a light emitting element are aligned in the pixel portion 6511.

Figure 4:
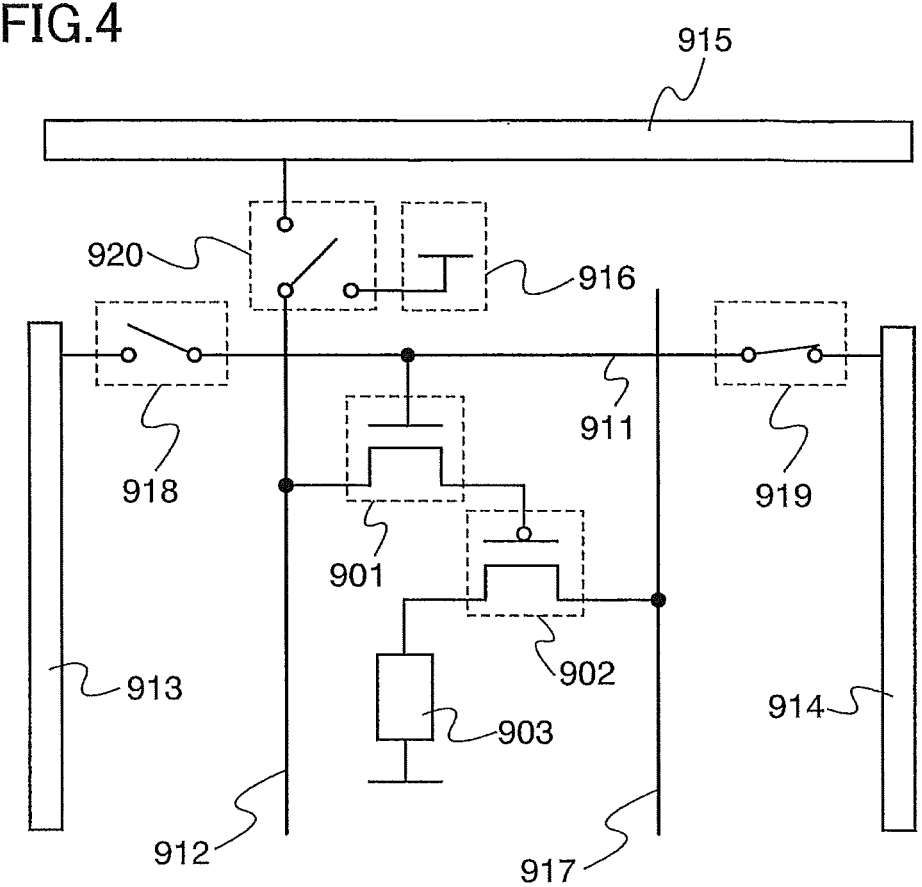
FIG. 4 is a diagram explaining a circuit included in a light emitting device to which the present invention is applied.

FIG. 4 is a diagram showing a circuit for operating one pixel. The circuit as shown in FIG. 4 comprises a first transistor 901, a second transistor 902 and a light emitting element 903.

Each of the first and second transistors 901 and 902 is a three terminal element including a gate electrode, a drain region and a source region. A channel region is interposed between the drain region and the source region. The region serving as the source region and the region serving as the drain region are changed depending on a structure of a transistor, an operational condition and the like so that it is difficult to determine which region serves as the source region or the drain region. Therefore, regions serving as the source or the drain are denoted as a first electrode and a second electrode in this embodiment mode, respectively.

A gate signal line 911 and a writing gate signal line driver circuit 913 are provided to be electrically connected or disconnected to each other by a switch 918. The gate signal line 911 and an erasing gate signal line driver circuit 914 are provided to be electrically connected or disconnected to each other by a switch 919. A source signal line 912 is provided to be electrically connected to either a source signal line driver circuit 915 or a power source 916 by a switch 920. A gate of the first transistor 901 is electrically connected to the gate signal line 911. The first electrode of the first transistor is electrically connected to the source signal line 912 while the second electrode thereof is electrically connected to a gate electrode of the second transistor 902. The first electrode of the second transistor 902 is electrically connected to a current supply line 917 while the second electrode thereof is electrically connected to one electrode included in the light emitting element 903. Further, the switch 918 may be included in the writing gate signal line driver circuit 913. The switch 919 may also be included in the erasing gate signal line driver circuit 914. In addition, the switch 920 may be included in the source signal line driver circuit 915.

Figure 5:
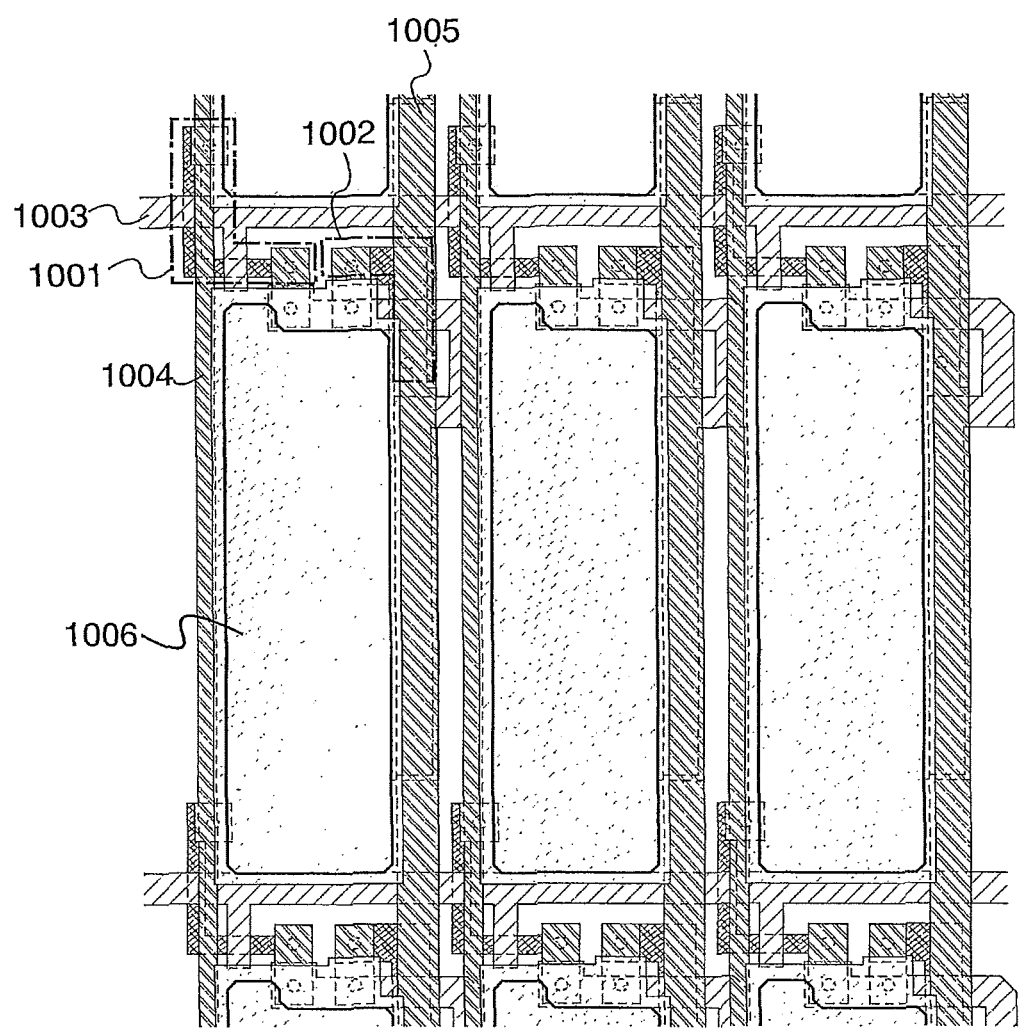
FIG. 5 is a top view of a light emitting device to which the present invention is applied.

The arrangement of transistors, light emitting elements and the like in the pixel portion is not particularly limited. For example, the arrangement as shown in a top view of FIG. 5 can be employed. In FIG. 5, a first electrode of a first transistor 1001 is connected to a source signal line 1004 while a second electrode of the first transistor is connected to a gate electrode of a second transistor 1002. A first electrode of the second transistor is connected to a current supply line 1005 and a second electrode of the second transistor is connected to an electrode 1006 of a light emitting element. A part of the gate signal line 1003 functions as a gate electrode of the first transistor 1001.

Figure 6:
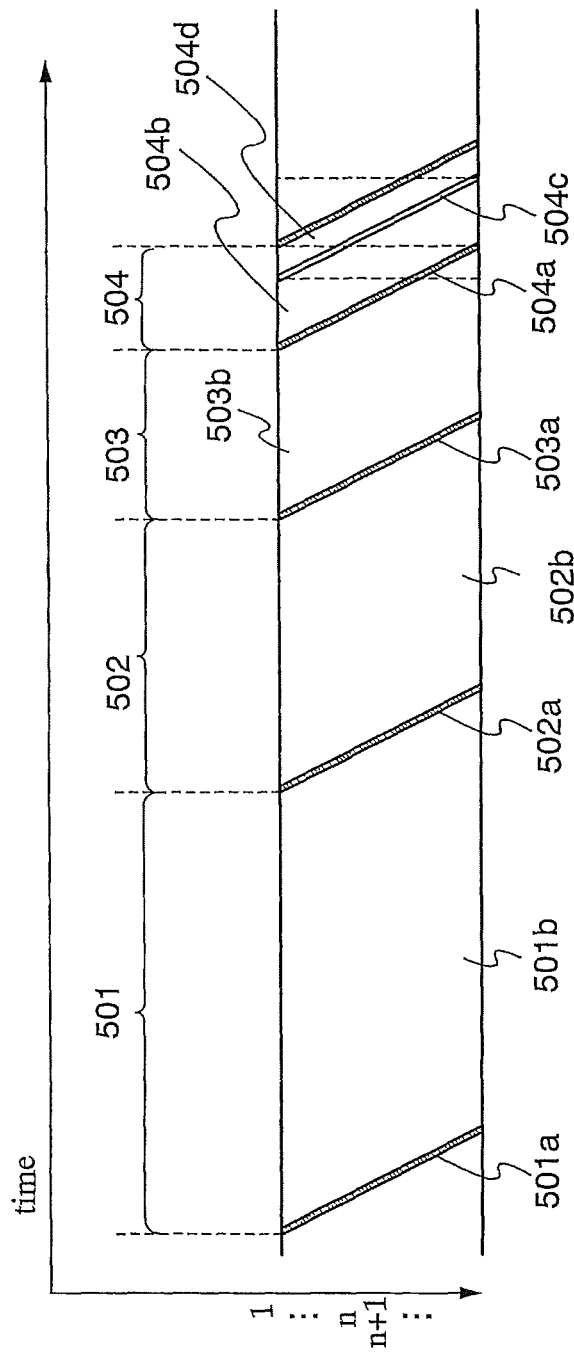
FIG. 6 is a diagram explaining a flame operation of a light emitting device to which the present invention is applied.

Next, the method for driving the light emitting device will be described below. FIG. 6 is a diagram explaining an operation of a frame with time. In FIG. 6, a horizontal direction indicates time passage while a longitudinal direction indicates the number of scanning stages of a gate signal line.

When an image is displayed on the light emitting device of the present invention, a rewriting operation is carried out repeatedly during a displaying period. The number of the rewriting operations is not particularly limited. However, the rewriting operation is preferably performed about 60 times a second such that a person who watches a displayed image does not detect flicker in the image. A period of operating the rewriting operation and the displaying operation of one image (one frame) is, herein, referred to as one frame period.

As shown in FIG. 6, one frame is divided into four sub-frames 501, 502, 503 and 504 including writing periods 501a, 502a, 503a and 504a and holding periods 501b, 502b, 503b and 504b. The light emitting element applied with a signal for emitting light emits light during the holding periods. The length ratio of the holding periods in the first sub-frame 501, the second sub-frame 502, the third sub-frame 503 and the fourth sub-frame 504 satisfies $2^3:2^2:2^1:2^0=8:4:2:1$. This allows the light emitting device to exhibit 4-bit gray scale. Further, the number of bits and the number of gray scales are not limited to those as shown in this embodiment mode. For instance, one frame may be divided into eight sub-frames so as to achieve 8-bit gray scale.

The operation in one frame will be described. In the sub-frame 501, the writing operation is first performed in a $1^{st}$ row to a last row, sequentially. Therefore, the starting time of the writing periods is varied for each row. The holding period 501b sequentially starts in the rows in which the writing period 501a has been terminated. In the holding period 501b, a light emitting element applied with a signal for emitting light remains in a light emitting state. Upon terminating the holding period 501b, the sub-frame 501 is changed to the next sub-frame 502 sequentially in the rows. In the sub-frame 502, a writing operation is sequentially performed in the $1^{st}$ row to the last row in the same manner as the sub-frame 501. The above-mentioned operations are carried out repeatedly up to the holding period 504b of the sub-frame 504 and then terminated. After terminating the operation in the sub-frame 504, an operation in the next frame starts. Accordingly, the sum of the light-emitting time in respective sub-frames corresponds to the light emitting time of each light emitting element in one frame. By changing the light emitting time for each light emitting element and combining such the light emitting elements variously within one pixel, various display colors with different brightness and different chromaticity can be obtained.

When the holding period is intended to be forcibly terminated in the row in which the writing period has already been terminated and the holding period has started prior to terminating the writing operation up to the last row as shown in the sub-frame 504, an erasing period 504c is preferably provided after the holding period 504b so as to stop light emission forcibly. The row where light emission is forcibly stopped does not emit light for a certain period (this period is referred to as a non light emitting period 504d). Upon terminating the writing period in the last row, a writing period of a next sub-frame (or, a next frame) immediately starts from a first row, sequentially. This can prevent the writing period in the sub-frame 504 from overlapping with the writing period in the next sub-frame.

Although the sub-frames 501 to 504 are arranged in order of descending the length of the holding period in this embodiment mode, they are not necessary to be arranged in this order. For example, the sub-frames may be arranged in ascending order of the length of the holding period. Alternatively, the sub-frames may be arranged in random order. In addition, these sub-frames may further be divided into a plurality of frames. That is, scanning of gate signal lines may be performed at several times during a period of supplying same video signals.

The operations in the wiring period and the erasing period of the circuits as shown in FIG. 4 will be described below.

The operation in the writing period will be described first. In the writing period, the gate signal line 911 in the n-th row (n is a natural number) is electrically connected to the writing gate signal line driver circuit 913 via the switch 918. The gate signal line 911 in the n-th row is electrically disconnected to the erasing gate signal line driver circuit 914. The source signal line 912 is electrically connected to the source signal line driver circuit 915 via the switch 920. In this case, a signal is input in a gate of the first transistor 901 connected to the gate signal line 911 in the n-th row (n is a natural number), thereby turning the first transistor 901 on. At this moment, video signals are simultaneously input in the source signal lines in the first to last columns. Further, the video signals input from the source signal line 912 in each column are independent from one another. The video signals input from the source signal line 912 are input in a gate electrode of the second transistor 902 via the first transistor 901 connected to the respective source signal lines. At this time, the amount of current supplied to the light emitting element 903 from the current supply line 917 is decided by the signals input in the second transistor 902. Also, it is decided whether the light emitting element 903 emits light or emits no light depending on the amount of current. For instance, when the second transistor 902 is of a P-channel type, the light emitting element 903 emits light by inputting a low level signal in the gate electrode of the second transistor 902. On the other hand, when the second transistor 902 is of an N-channel type, the light emitting element 903 emits light by inputting a high level signal in the gate electrode of the second transistor 902.

Next, the operation in the erasing period will be described. In the erasing period, the gate signal line 911 in the n-th row (n is a natural number) is electrically connected to the erasing gate signal line driver circuit 914 via the switch 919. The gate signal line 911 in the n-th row is not electrically connected to the writing gate signal line deriver circuit 913. The source signal line 912 is electrically connected to the power source 916 via the switch 920. In this case, upon inputting a signal in the gate of the first transistor 901, which is connected to the gate signal line 911 in the n-th row, the first transistor 901 is turned on. At this time, erasing signals are simultaneously input in the first to last columns of the source signal lines. The erasing signals input from the source signal line 912 are input in the gate electrode of the second transistor 902 via the first transistor 901, which is connected to each source signal line. A supply of current flowing through the light emitting element 903 from the current supply line 917 is forcibly stopped by the signals input in the second transistor 902. This makes the light emitting element 903 emit no light forcibly. For example, when the second transistor 902 is of a P-channel type, the light emitting element 903 emits no light by inputting a high level signal in the gate electrode of the second transistor 902. On the other hand, when the second transistor 902 is of an N-channel type, the light emitting element 903 emits no light by inputting a low level signal in the gate electrode of the second transistor 902.

Further, in the erasing period, a signal for erasing is input in the n-th row (n is a natural number) by the above-mentioned operation. However, as mentioned above, the n-th row sometimes remains in the erasing period while another row (e.g., an m-th row (m is a natural number)) remains in the writing period. In this case, since a signal for erasing is necessary to be input in the n-th row and a signal for writing is necessary to be input in the m-th row by utilizing the source signal line in the same column, the after-mentioned operation is preferably carried out.

After the light emitting element 903 in the n-th row becomes a non-light emitting state by the above-described operation in the erasing period, the gate signal line 911 and the erasing gate signal line driver circuit 914 are immediately disconnected to each other and the source signal line 912 is connected to the source signal line driver circuit 915 by turning the switch 920 on/off. The gate signal line 911 and the writing gate signal line driver circuit 913 are connected to each other while the source signal line and the source signal line driver circuit 915 are connected to each other. A signal is selectively input in the signal line in the m-th row from the writing gate signal line driver circuit 913 and the first transistor is turned on while signals for writing are input in the source signal lines in the first to last columns from the source signal line driver circuit 915. By inputting these signals, the light emitting element in the m-th row emits light or no light.

After terminating the writing period in the m-th row as mentioned above, the erasing period immediately starts in the n+1-th row. Therefore, the gate signal line 911 and the writing gate signal line driver circuit 913 are disconnected to each other while the source signal line is connected to the power source 916 by turning the switch 920 on/off. Also, the gate signal line 911 and the writing gate signal line driver circuit 913 are disconnected to each other while the gate signal line 911 is connected to the erasing gate signal line driver circuit 914. A signal is selectively input in the gate signal line in the n+1-th row from the erasing gate signal line driver circuit 914 to input a signal for turning on the first transistor in the first transistor while an erasing signal is input therein from the power source 916. Upon terminating the erasing period in the n+1-th row in this manner, the writing period immediately starts in the m+1-th row. The erasing period and the writing period may be repeated alternately until the erasing period of the last row in the same manner.

Although the writing period in the m-th row is provided between the erasing period in the n$^{th}$ row and the erasing period of the n+1-th row in this embodiment mode, the present invention is not limited thereto. The writing period of the m-th row may be provided between the erasing period in the n−1-th row and the erasing period in the n-th row.

Furthermore, in this embodiment mode, when the non-light emitting period 504*d* is provided like the sub-frame 504, the operation of disconnecting the erasing gate signal line driver circuit 914 from one gate signal line while connecting the writing gate signal line driver circuit 913 to other gate signal line is carried out repeatedly. This operation may be performed in a frame in which a non-light emitting period is not particularly provided.

[Embodiment Mode 5]

A circuit having a function of controlling light emission or non light emission of a light emitting element is not limited to the one shown in FIG. 4. For example, a circuit as shown in FIG. 7 may be used.

Figure 7:
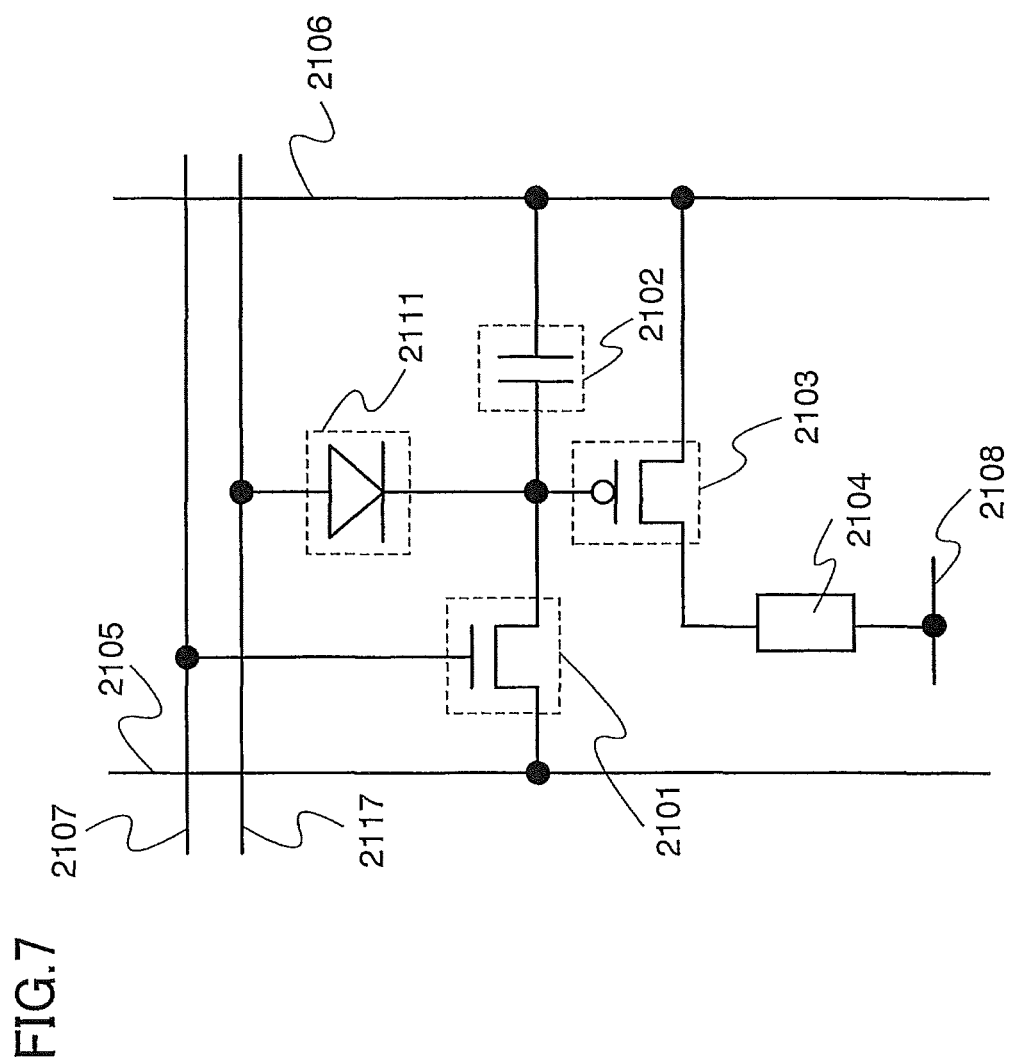
FIG. 7 is a diagram explaining a circuit included in a light emitting device to which the present invention is applied.

In FIG. 7, a first transistor 2101, a second transistor 2103, an erasing diode 2111, and a light emitting element 2104 are arranged. A source and a drain of the first transistor 2101 are independently connected to a signal line 2105 and a gate of the second transistor 2103. The gate of the first transistor 2101 is connected to a first gate line 2107. A source and a drain of the second transistor 2103 are independently connected to a power source line 2106 and the light emitting element 2104. The erasing diode 2111 is connected to both the gate of the second transistor 2103 and a second gate line 2117.

A holding capacitor 2102 has a function of holding a gate potential of the second transistor 2103. Therefore, the holding capacitor connected between the gate of the second transistor 2103 and the power source line 2106. However, the position of the holding capacitor 2102 is not limited thereto. The holding capacitor 2102 may be placed such that the holding capacitor holds the gate potential of the second transistor 2103. When the gate potential of the second transistor 2103 can be held by using a gate capacitor of the second transistor 2103 or the like, the holding capacitor 2102 may be eliminated.

A driving method is as follows. The first gate line 2107 is selected to turn the first transistor 2101 on, and then a signal is input in the holding capacitor 2102 from the signal line 2105. Then, a current of the second transistor 2103 is controlled in accordance with the signal so that the current flows to a second power source line 2108 from a first power source line 2106 through the light emitting element 2104.

In order to erase the signal, the second gate line 2117 is selected (in this case, a potential of the second gate line is increased) and the erasing diode 2111 is turned on to feed a current to a gate of the second transistor 2103 from the second gate line 2117. Consequently, the second transistor 2103 becomes an off-state. Then, a current does not flow to the second power source line 2108 from the first power source line 2106 through the light emitting element 2104. As a result, a non-light emitting period can be made and a lighting period can be freely controlled.

In order to hold a signal, the second gate line 2117 is not selected (in this case, a potential of the second date line is reduced). Thus, since the erasing diode 2111 is turned off, a gate potential of the second transistor 2103 is held.

Further, the erasing diode 2111 is not particularly limited so long as it is an element having a rectifying property. Either a PN-type diode or a PIN-type diode may be used. Alternatively, either a Schottky diode or a zener diode may be used.

Further, a diode connection (i.e., a gate and a drain are connected to each other) may be carried out using transistors. Moreover, a P-channel type transistor may be used.

[Embodiment Mode 6]

Examples of light emitting device including light emitting elements of the present invention will be described referring to cross sectional views of FIGS. 8A to 8C.

Figure 8A:
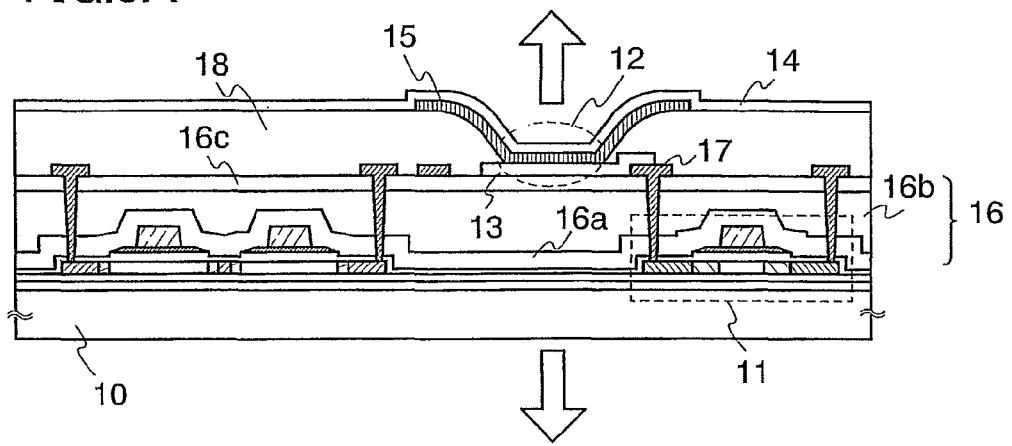
FIGS. 8A to 8C are cross sectional views of a light emitting device to which the present invention is applied.
Figure 8B:
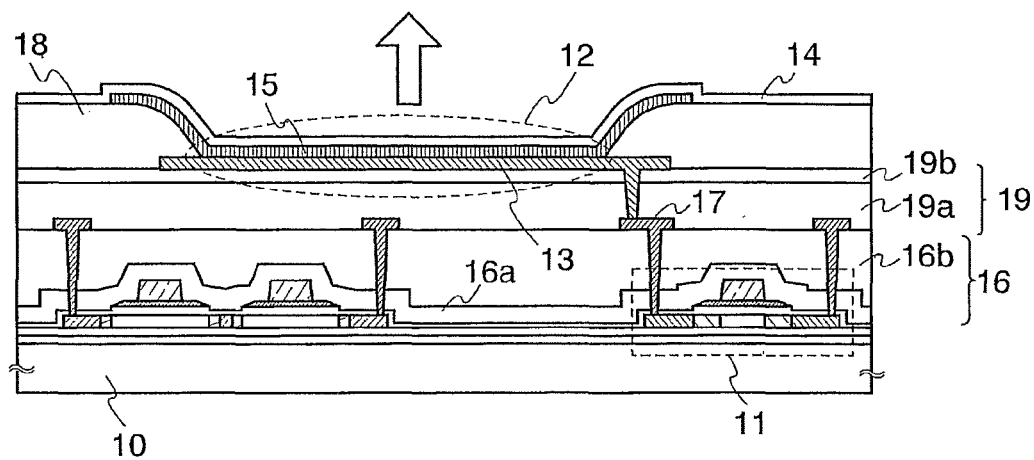
Figure 8C:
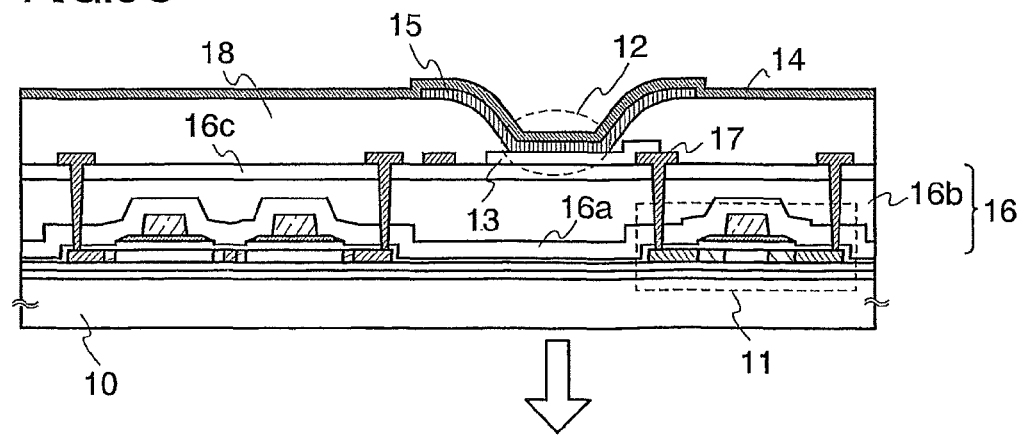

In each of FIGS. 8A to 8C, a transistor 11 that is provided for driving a light emitting element 12 of the present invention is surrounded by a dashed line. The light emitting element 12 of the present invention comprises a light emitting layer 15 between a first electrode 13 and a second electrode 14. A drain of the transistor 11 and the first electrode 13 are electrically connected to each other via a wiring 17 that passes through a first interlayer insulating film 16 (16a, 16b and 16c). The light emitting element 12 is isolated from other adjacent light emitting element by a partition wall layer. A light emitting device having such a structure is provided over a substrate 10 in this embodiment mode.

The transistor 11 shown in each of FIGS. 8A to 8C is of a top-gate type in which a gate electrode is provided on a semiconductor layer at a side opposite to the substrate. Further, the structure of the transistor 11 is not particularly limited thereto, and for example, a bottom-gate type structure may be employed. In the case of the bottom-gate type, either a structure in which a protection film is formed over a semiconductor layer forming a channel (a channel protection type) or a structure in which a semiconductor layer forming a channel is partly etched (a channel-etched type) may be used.

Furthermore, a semiconductor layer included in the transistor 11 may be formed using any one of a crystalline semiconductor, an amorphous semiconductor, a semiamorphous semiconductor, and the like.

Specifically, the semiamorphous semiconductor has an intermediate structure between an amorphous structure and a crystalline structure (including a single crystal structure and a polycrystalline structure), and a third condition that is stable in term of free energy. The semiamorphous semiconductor further includes a crystalline region having a short range order along with lattice distortion. A crystal grain with a size of 0.5 to 20 nm is included in at least a part of an semiamorphous semiconductor film. Raman spectrum is shifted toward lower wavenumbers than 520 cm$^{-1}$. The diffraction peaks of (111) and (220), which are believed to be derived from Si crystal lattice, are observed in the semiamorphous semiconductor by the X-ray diffraction. The semiamorphous semiconductor contains hydrogen or halogen of at least 1 atom % or more for terminating dangling bonds. The semiamorphous semiconductor is also referred to as a microcrystalline semiconductor. The semiamorphous semiconductor is formed by glow discharge decomposition with silicide gas (plasma CVD). As for the silicide gas, $SiH_4$; $Si_2H_6$, $SiH_2Cl_2$, $SiHCl_3$, $SiCl_4$, $SiF_4$ and the like can be used. The silicide gas may also be diluted with $H_2$, or a mixture of $H_2$ and one or more of rare gas elements selected from He, Ar, Kr and Ne. The dilution ratio is set to be in the range of 1:2 to 1:1,000. The pressure is set to be approximately in the range of 0.1 to 133 Pa. The power frequency is set to be 1 to 120 MHz, and preferably, 13 to 60 MHz. A substrate heating temperature may be set to be 300° C. or less, and preferably, 100 to 250° C. With respect to impurity elements contained in the film, each concentration of impurities for atmospheric constituents such as oxygen, nitrogen and carbon is preferably set to be $1 \times 10^{20}/cm^3$ or less. In particular, the oxygen concentration is set to be $5 \times 10^{19}/cm^3$ or less, and preferably, $1 \times 10^{19}/cm^3$ or less.

As a specific example of a crystalline semiconductor layer, a semiconductor layer made from single crystalline silicon, polycrystalline silicon, silicon germanium, or the like can be given. The crystalline semiconductor layer may be formed by laser crystallization. For example, the crystalline semiconductor layer may be formed by crystallization with use of a solid phase growth method using nickel or the like.

When a semiconductor layer is formed using an amorphous substance, e.g., amorphous silicon, it is preferable to use a light emitting device with circuits including only N-channel transistors as the transistor 11 and other transistor (a transistor included in a circuit for driving a light emitting element). Alternatively, a light emitting device with circuits including either N-channel transistors or P-channel transistors may be employed. Also, a light emitting device with circuits including both an N-channel transistor and a P-channel transistor may be used.

The first interlayer insulating film 16 may include either plural layers as shown in FIGS. 5A and 8C or a single layer. Specifically, an interlayer insulating layer 16a is formed using an inorganic material such as silicon oxide and silicon nitride. An interlayer insulating layer 16b is formed using acrylic, siloxane (which is a compound that has a skeleton structure formed by silicon (Si)-oxygen (O) bonds and includes hydrogen or an organic group such as an alkyl group as its substituent), or a substance with a self-planarizing property that can be formed by applying a material such as silicon oxide. An interlayer insulating layer 16c is formed using a silicon nitride film containing argon (Ar). The substances constituting the respective layers are not particularly limited thereto. Therefore, substances other than the above-mentioned substances may be employed. Alternatively, a layer formed using a substance other than the above mentioned substances may be provided in combination with the above described layers. Accordingly, the first interlayer insulating film 16 may be formed by using both an inorganic material and an organic material or by using either an inorganic material or an organic material.

The edge portion of the partition wall layer 18 preferably has a shape in which the radius of curvature is continuously varied. This partition wall layer 18 is formed by using acrylic, siloxane, resist, silicon oxide, or the like. Further, the partition wall layer 18 may be formed using any one or both of an inorganic film and an organic film.

FIGS. 8A and 8C show the structures in which only the first interlayer insulating film 16 (16a, 16b and 16c) is sandwiched between the transistors 11 and the light emitting elements 12. Alternatively, as shown in FIG. 8B, the first interlayer insulating film 16 (16a and 16b) and a second interlayer insulting film 19 (19a and 19b) may be provided between the transistor 11 and the light emitting element 12. In the light emitting device as shown in FIG. 8B, the first electrode 13 passes through the second interlayer insulating film 19 to be connected to the wiring 17.

The second interlayer insulating film 19 may include either plural layers or a single layer as well as the first interlayer insulating film 16. A second interlayer insulating layer 19a is formed using acrylic, siloxane, or a substance with a self-planarizing property that can be formed by applying a material such as silicon oxide. A second interlayer insulating layer 19b is formed using a silicon nitride film containing argon (Ar). The substances constituting the respective layers of the second interlayer insulating film are not particularly limited thereto. Therefore, substances other than the above-mentioned substances may be employed. Alternatively, a layer made from a substance other than the above-mentioned substances may be provided in combination with the layers 19a and 19b. Accordingly, the second interlayer insulating film 19 may be formed by using both an inorganic material and an organic material or by using either an inorganic material or an organic material.

When the first electrode and the second electrode are both formed using a substance with a light transmitting property in the light emitting element 12, light generated in the light emitting element can be emitted through both the first electrode 13 and the second electrode 14 as shown in arrows in FIG. 8A. When only the second electrode 14 is formed using a substance with a light transmitting property, light generated in the light emitting element 12 can be emitted only through the second electrode 14 as shown in an arrow of FIG. 8B. In this case, the first electrode 13 is preferably formed using a material with high reflectance. Alternatively, a film (reflection film) formed using a material with high reflectance is preferably provided underneath the first electrode 13. When only the first electrode 13 is formed using a substance with a light transmitting property, light generated in the light emitting element 12 can be emitted only through the first electrode 13 as shown in an arrow of FIG. 8C. In this case, the second electrode 14 is preferably formed using a material with high reflectance or a reflection film is preferably provided over the second electrode 14.

Moreover, in the light emitting element 12, the first electrode 13 may serves as an anode and the second electrode 14 may serve as a cathode. Alternatively, the first electrode 13 may serves as a cathode and the second electrode 14 may serves as an anode. In the former case, the transistor 11 is a P-channel transistor. In the latter case, the transistor 11 is an N-channel transistor.

[Embodiment Mode 7]

As described in Embodiment Modes 4 to 6, a light emitting element of the present invention may be connected to a transistor to be used as a pixel of an active matrix light emitting device which emits light or no light upon receiving a signal from the transistor. Alternatively, a light emitting element of the present invention may be used for a passive light emitting device as shown in FIG. 46 that drives the light emitting element without providing an element for driving the transistor and the like.

Figure 46:
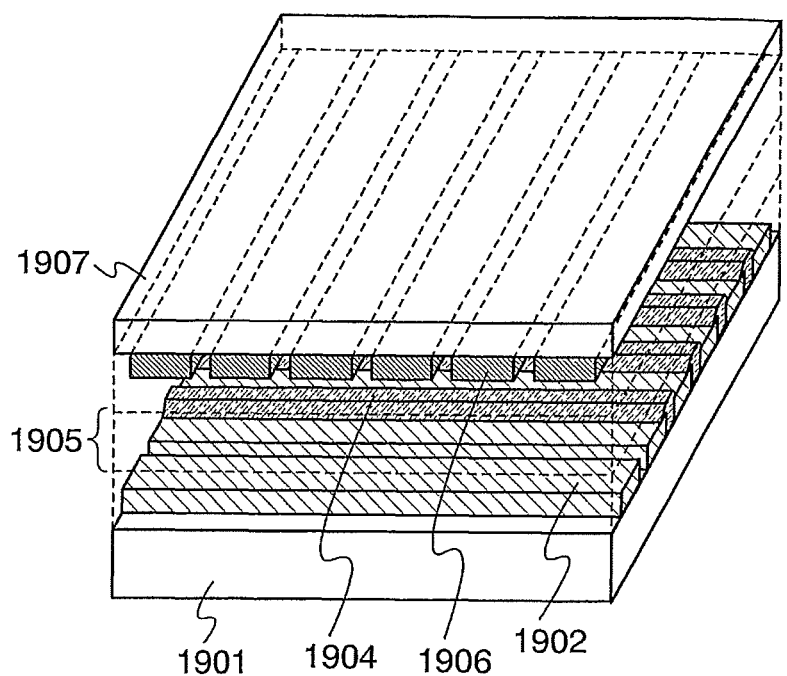
FIG. 46 is a diagram explaining a mode of a light emitting device of the present invention.

FIG. 46 shows a perspective view of a passive light emitting device manufactured using the present invention. In FIG. 46, an electrode 1902 and an electrode 1906 are provided between a substrate 1901 and a substrate 1907. The electrode 1902 and the electrode 1906 are provided to intersect each other. Further, a light emitting layer 1905 (which is depicted by a dashed line such that the arrangement of the electrode 1902, a partition wall layer 1904 and the like can be recognized) is provided between the electrode 1902 and the electrode 1906. In addition, a hole transporting layer, an electron transporting layer and the like may be provided between the light emitting layer 1905 and the electrode 1902, or between the light emitting layer 1905 and the electrode 1906. The partition wall layer 1904 is provided at the edge of the electrode 1902. Thus, the edge of the electrode 1902 is covered with the partition wall layer 1904. Furthermore, the passive light emitting device can be driven at low power consumption by using a light emitting element of the present invention that is operated at a low driving voltage.

[Embodiment Mode 8]

By mounting a light emitting device of the present invention, an electronic appliance that can display favorable images for a long time and has less false recognition of information due to fluctuation of a display image, can be obtained.

Figure 9A:
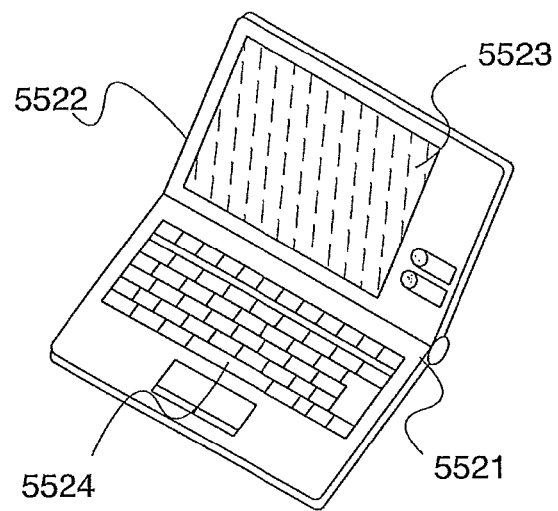
FIGS. 9A to 9C are diagrams of electronic appliances to which the present invention is applied.
Figure 9B:
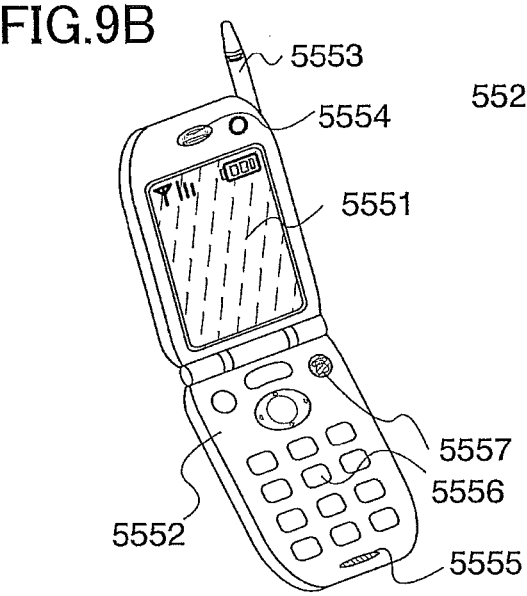
Figure 9C:
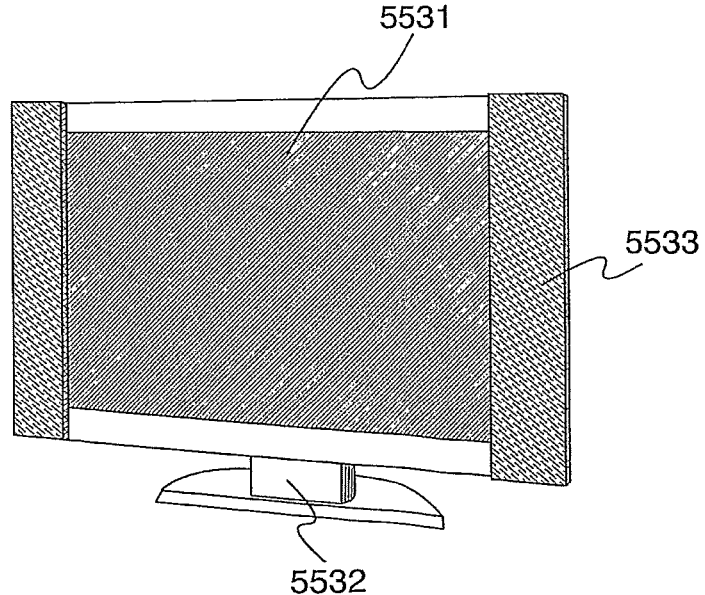

Examples of electronic appliances on which light emitting device of the present invention is mounted will be shown in FIGS. 9A to 9C.

FIG. 9A shows a laptop personal computer manufactured in accordance with the present invention, comprising a main body 5521, a housing 5522, a display portion 5523, a keyboard 5524, and the like. By incorporating a light emitting device having a light emitting element of the present invention into the display portion, the personal computer can be completed.

FIG. 9B shows a portable phone manufactured in accordance with the present invention, comprising a main body 5552, a display portion 5551, an audio output portion 5554, an audio input portion 5555, operation switches 5556 and 5557, an antenna 5553 and the like. By incorporating a light emitting device having a light emitting element of the present invention into the display portion, the portable phone can be completed.

FIG. 9C shows a television receiver manufactured in accordance with the present invention, comprising a display portion 5531, a housing 5532, speakers 5533, and the like. By incorporating a light emitting device having a light emitting element of the present invention into the display portion, the television receiver can be completed.

As set forth above, a light emitting device of the present invention is suitable to be used as a display portion of various kinds of electronic appliances.

Although the laptop personal computer, the portable phone and the television receiver are described in the present embodiment mode, light emitting devices having light emitting elements of the present invention may be mounted on a car navigation, a camera, a lighting apparatus and the like.

[Embodiment 1]

SYNTHETIC EXAMPLE 1

A method for synthesizing an anthracene derivative represented by the structural formula (1) will be described in this synthetic example.

[Step 1]

A method for synthesizing 9,10-bis(4-bromophenyl)-2-tert-butylanthracene will be described.

Under nitrogen gas stream at a temperature of −78° C., 1.58 mol/L (13.4 ml) of a butyllithium hexane solution was dropped in a dry ether solution (200 ml) containing 5.0 g of 1,4-dibromobenzene. After dripping the butyllithium hexane solution, the mixture was stirred for one hour at the same temperature. At a temperature of −78° C., a dry ether solution (40 ml) containing 2-teret-butyl anthraquinone (2.80 g) was dropped in the mixture, and then the reaction solution was slowly heated to a room temperature. After the reaction solution was stirred for overnight, water was added thereto, and an organic layer was extracted with ethyl acetate. The organic layer was washed with saturated saline and dried with magnesium sulfate. The dried matter was filtered and concentrated. Then, the residue was purified by a silica gel chromatography (a developing solvent, hexane-ethyl acetate) to obtain 5.5 g of a compound.

When the thus obtained compound was measured by a nuclear magnetic resonance ($^1$H-NMR) method, it was confirmed that the compound was 9, 10-bis(4-bromophenyl)-2-tert-butyl-9,10-dihydroxy-9,10-dihydroanthracene.

The $^1$H-NMR of this compound is shown below. The $^1$H-NMR (300 MHz, CDCl$_3$): δ=1.31 (s, 9H), 2.81 (s, 1H), 2.86 (s, 1H), 6.82-6.86 (m, 4H), 7.13-7.16 (m, 4H), 7.36-7.43 (m, 3H), and 7.53-7.70 (m, 4H).

Also, a synthetic scheme (b-1) of the 9,10-bis(4-bromophenyl)-2-tert-butyl-9,10-dihydroxy-9,10-dihydroanthracene is shown below.

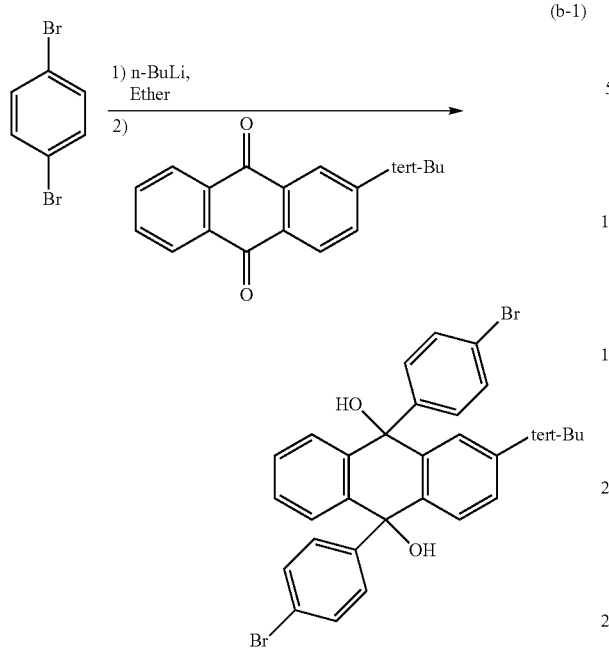

(b-1)

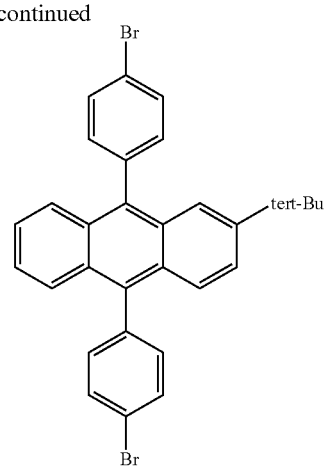

[Step 2]
A method for synthesizing 3-(N-phenylamino)-9-phenylcarbazole will be described.

Firstly, 24.3 g (100 mmol) of N-phenylcarbazole was dissolved in 600 ml of glacial acetic acid, and 17.8 g (100 mmol) of N-bromo succinic acid imide was slowly added thereto. The mixture was stirred for overnight at a room temperature. This glacial acetic acid solution was dropped in 1 L of ice water while stirring them. A precipitated white solid was washed three times with water. This white solid was dissolved in 150 ml of diethyl ether, and washed with a saturated sodium hydrogencarbonate solution and water. This organic layer was dried with magnesium sulfate, and filtered. The obtained filtrate was concentrated. The thus obtained residue was added with about 50 ml of methanol and uniformly dissolved therein by being irradiated with supersonic. This solution was left to precipitate a white solid. This solution was filtrated and the filtrate was dried to obtain 28.4 g (the yield: 88%) of 3-bromo-9-phenylcarbazole, which was a white powder.

Further, a synthetic scheme (c-1) of 3-bromo-9-phenylcarbazole is shown below.

Under atmospheric air, 987 mg (1.55 mmol) of the thus obtained 9,10-bis(4-bromophenyl)-2-tert-butyl-9,10-dihydroxy-9,10-dihydroanthracene, 664 mg (4 mmol) of potassium iodide and 1.48 g (14 mmol) of sodium phosphine acid monohydrate were suspended in 12 ml of glacial acetic acid. The mixture was refluxed and stirred while heating for two hours. The reaction mixture was cooled to the room temperature and the thus generated precipitate was filtered and washed with about 50 ml of methanol to obtain a filtrate. The filtrate was dried to obtain 700 mg of a compound which was a cream-colored powder. The yield was 82%. When this compound was measured by a nuclear magnetic resonance ($^1$H-NMR, $^{13}$C-NMR) method, it was confirmed that the compound was 9,10-bis(4-bromophenyl)-2-tert-butylanthracene.

The $^1$H-NMR and the $^{13}$C-NMR of this compound are shown below.

The $^1$H-NMR (300 MHz, CDCl$_3$): δ=1.28 (s, 9H), 7.25-7.37 (m, 6H), 7.44-7.48 (m, 1H), 7.56-7.65 (m, 4H), and 7.71-7.76 (m, 4H).

The $^{13}$C-NMR (47 MHz, CDCl$_3$): δ=30.8, 35.0, 120.8, 121.7, 121.7, 124.9, 125.0, 125.2, 126.4, 126.6, 126.6, 128.3, 129.4, 129.7, 129.9, 131.6, 131.6, 133.0, 133.0, 135.5, 135.7, 138.0, 138.1, and 147.8.

Further, a synthetic scheme (b-2) of 9,10-bis(4-bromophenyl)-2-tert-butylanthracene is shown below.

(b-2)

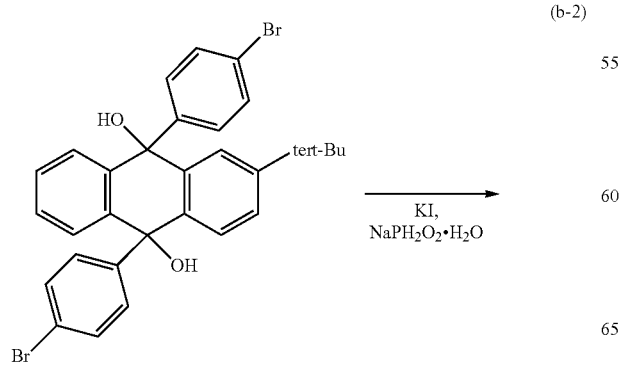

(c-1)

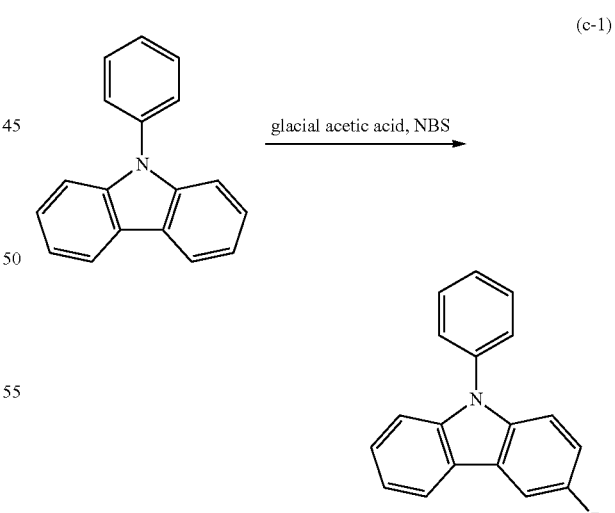

Next, under nitrogen, 110 ml of dehydrated xylene and 7.0 g (75 mmol) of aniline were added to a mixture of 19 g (60 mmol) of 3-bromo-9-phenylcarbazole, 340 mg (0.6 mmol) of bis(dibenzylidene acetone) palladium (0) (abbreviation: Pd(dba)$_2$), 1.6 g (3.0 mmol) of 1,1-bis(diphenylphosphino) ferrocene (abbreviation: DPPF), and 13 g (180 mmol) of sodium-tert-butoxide (abbreviation: tBuONa). This mixture was stirred while heating under nitrogen atmosphere at 90° C. for 7.5 hours. After the termination of the reaction, about 500 ml of toluene, which was heated to 50° C., was added to the suspension and this suspension was filtered through florisil, alumina and celite. The thus obtained filtrate was concentrated and the residue was added with hexane-ethyl acetate and irradiated with supersonic. The thus obtained suspension was filtered and the filtrate was dried to obtain 15 g (the yield: 75%) of a cream-colored powder. By using a nuclear magnetic resonance ($^1$H-NMR) method, it was confirmed that this cream-colored powder was 3-(N-phenylamino)-9-phenylcarbazole (abbreviation: PCA).

Figure 13A:
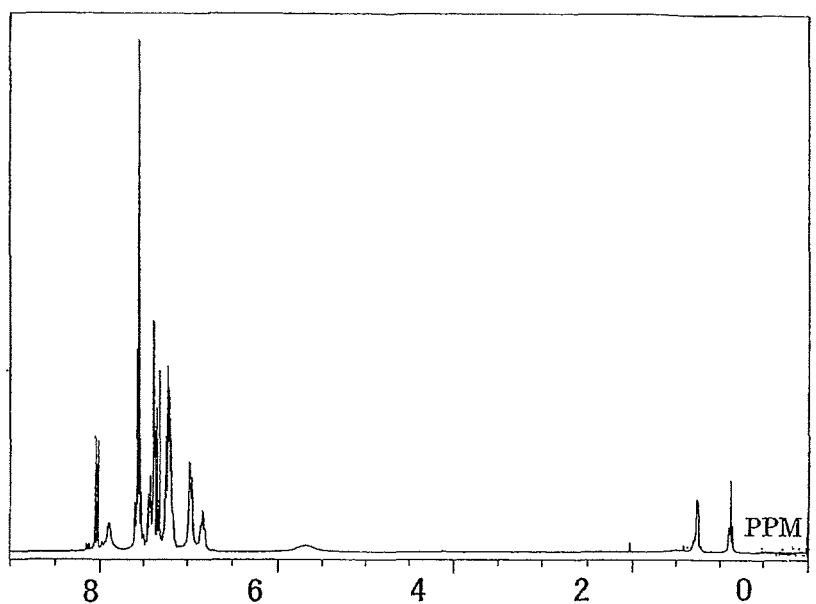
FIGS. 13A and 13B are $^1$H-NMR charts of PCA synthesized in Synthetic Example 1.
Figure 13B:
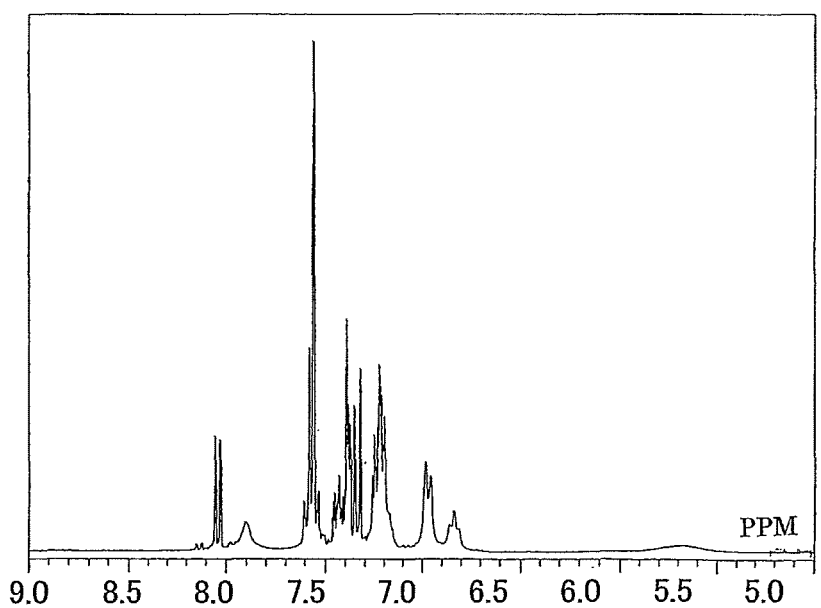

The $^1$H-NMR of the compound is shown below. The $^1$H-NMR charts are also shown in FIGS. 13A and 13B. Further, FIG. 13B is a chart showing an enlarged part in the range of 5 ppm to 9 ppm of FIG. 13A.

The $^1$H-NMR (300 MHz, CDCl$_3$): δ=5.69 (s, 1H), 6.84 (t, J=6.9, 2 H), 6.97 (d, J=7.8, 2H), 7.20-7.61 (m, 13H), 7.90 (s, 1H), and 8.04 (d, j=7.8, 1H).

Further, a synthetic scheme (c-2) of 3-(N-phenylamino)-9-phenylcarbazole is shown below.

500 mg (the yield: 48%) of a yellow green powder. By using a nuclear magnetic resonance ($^1$H-NMR) method, it was confirmed that this yellow green powder was 9,10-bis{4-[N-(9-phenylcarbazole-3-yl)-N-phenylamino]phenyl}-2-tert-butylanthracene (abbreviation: PCABPA).

Figure 14A:
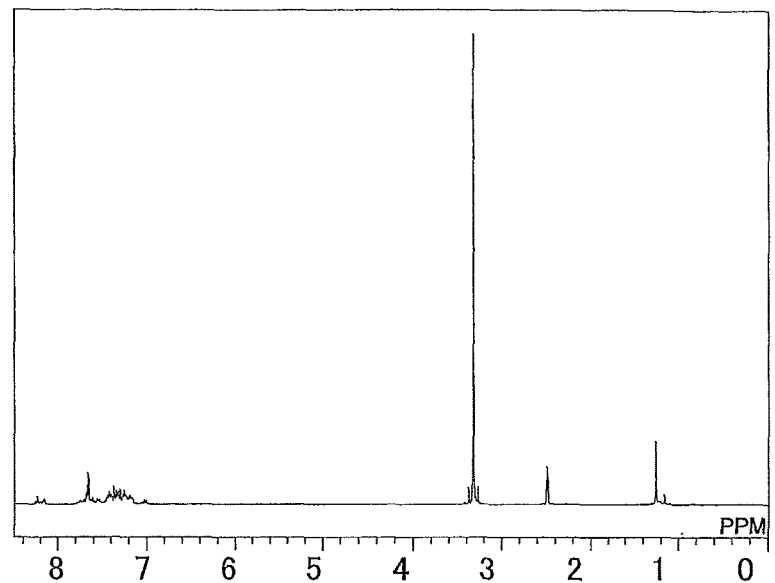
FIGS. 14A and 14B are $^1$H-NMR charts of PCABPA synthesized in Synthetic Example 1.
Figure 14B:
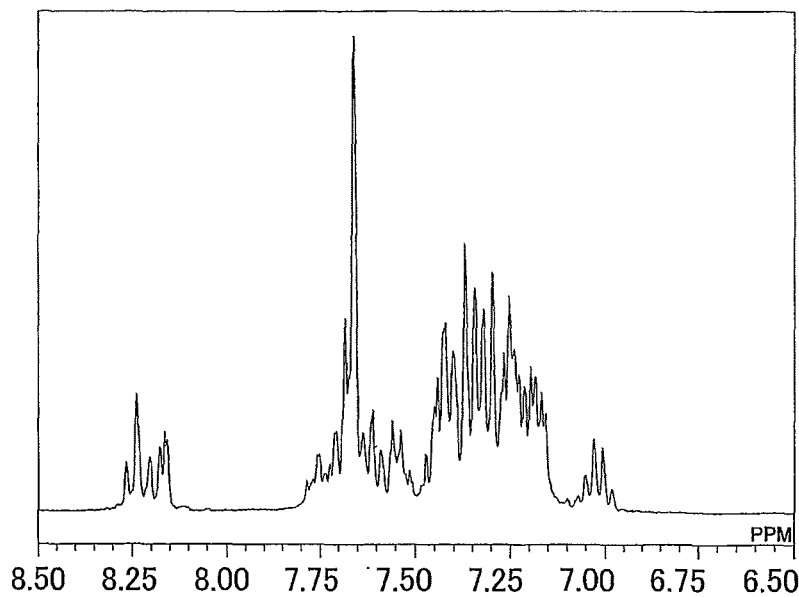

The $^1$H-NMR of the compound is shown below. The $^1$H-NMR charts are also shown in FIGS. 14A and 14B. Further, FIG. 14B is a chart showing an enlarged part in the range of 6.5 ppm to 8.5 ppm of FIG. 14A.

The $^1$H-NMR (300 MHz, DMSO-d): δ=3.33 (s, 9H), 6.98-7.79 (m, 44H), and 8.16-8.27 (m, 4H).

Further, a synthetic scheme (d-1) of PCABPA is shown below.

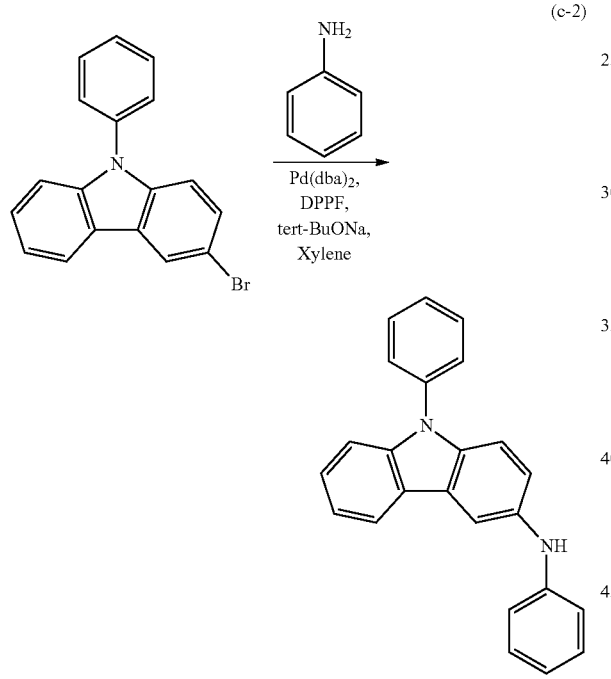

[Step 3]
A method for synthesizing 9,10-bis{4-[N-(9-phenylcarbazole-3-yl)-N-phenylamino]phenyl}-2-tert-butylanthracene (abbreviation: PCABPA) will be described.

Under nitrogen, 10 ml of dehydrated toluene was added to a mixture of 540 mg (1.0 mmol) of 9,10-bis(4-bromophenyl)-2-tert-butylanthracene, 670 mg (2.0 mmol) of 3-(N-phenylamino)-9-phenylcarbazole, 12 mg (0.02 mmol) of bis(dibenzylidene acetone) palladium (0), 110 mg (0.2 mmol) of 1,1-bis(diphenylphosphino) ferrocene, and 600 mg (6.2 mmol) of sodium-tert-butoxide. This mixture was stirred while heating at 90° C. for five hours under nitrogen atmosphere. After termination of the reaction, the suspension was added with about 100 ml of toluene, and then filtered through florisil, alumina and celite. The thus obtained filtrate was concentrated and a target matter was obtained by a silica gel chromatography (toluene:hexane=1: 1). The target matter was concentrated and the thus obtained residue was recrystallized by diclomethane-hexane to obtain

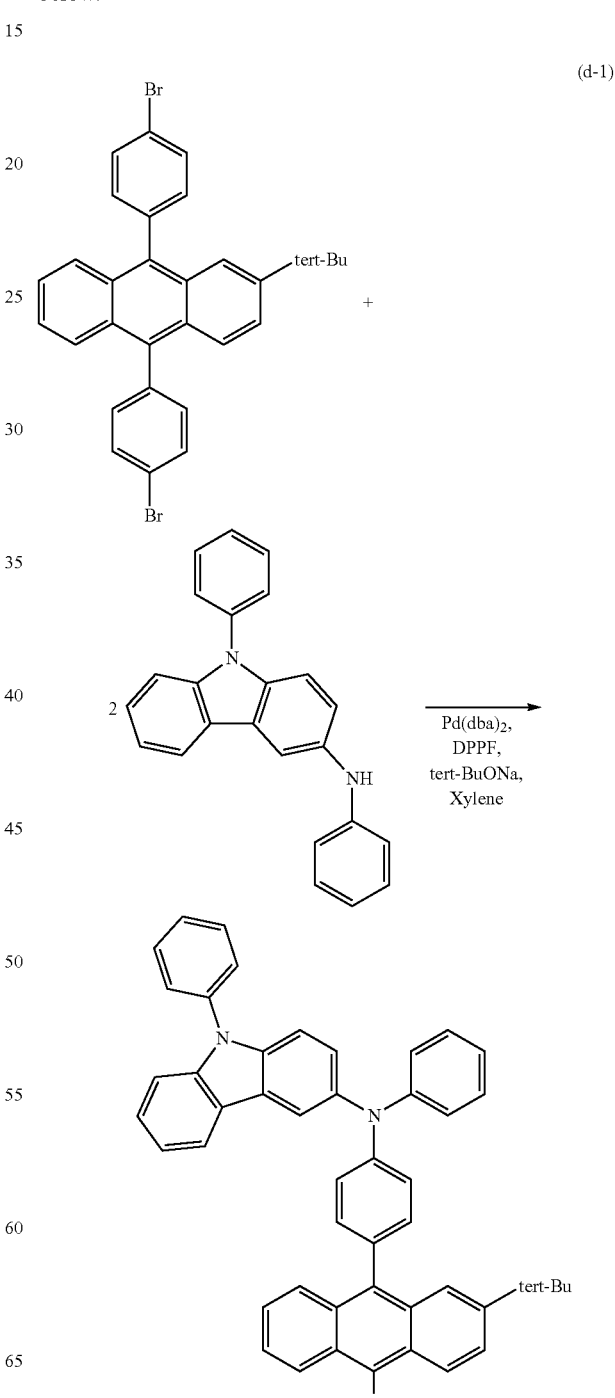

-continued

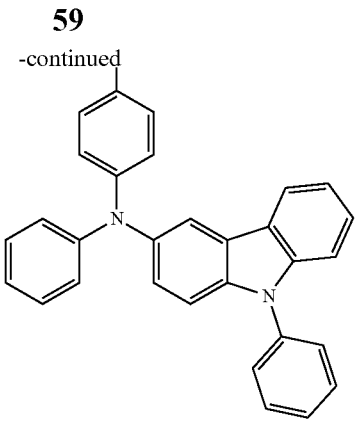

Figure 10:
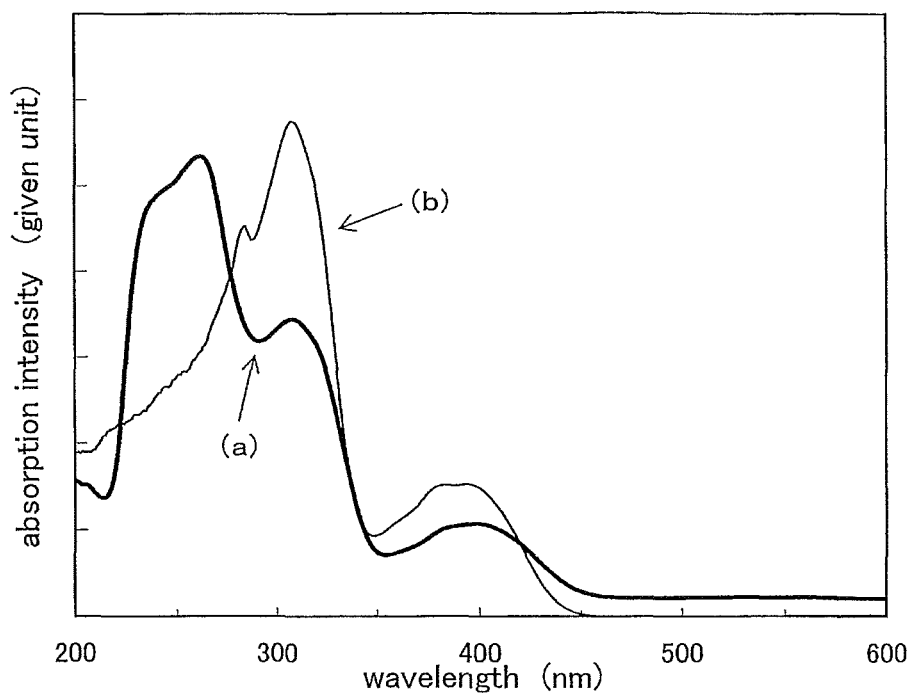
FIG. 10 is a graph showing an absorption spectrum of an anthracene derivative of the present invention.
Figure 11:
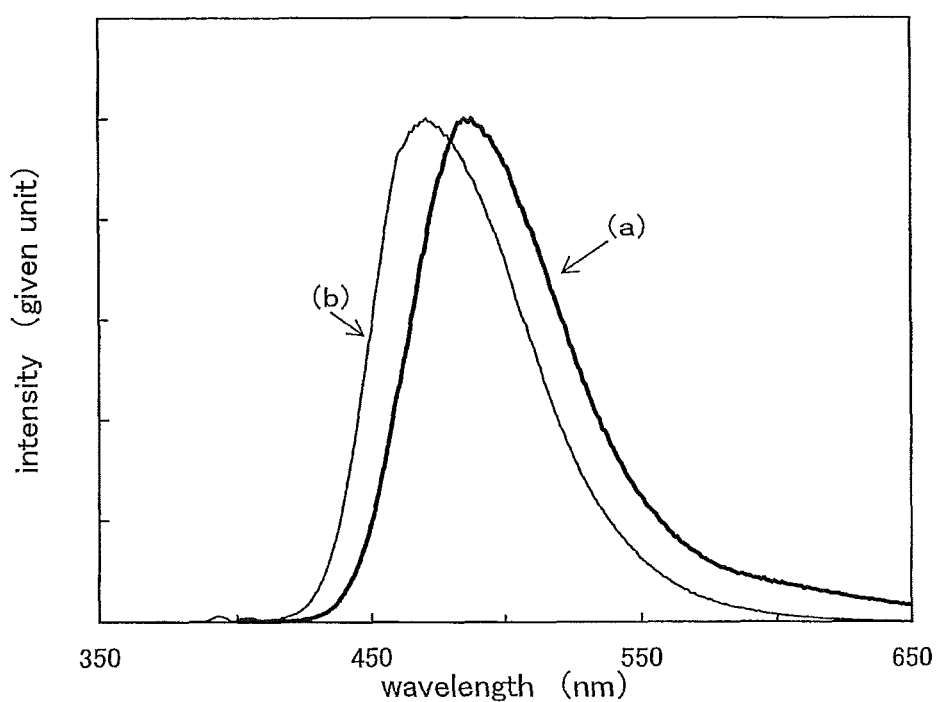
FIG. 11 is a graph showing an absorption spectrum of an anthracene derivative of the present invention.

The absorption spectrums of the PCABPA are shown in FIG. 10. In FIG. 10, a horizontal axis represents a wavelength (nm) and a longitudinal axis represents the absorption intensity (given unit). Further, a line (a) indicates the absorption spectrum in the case where the PCABPA was a film form whereas a line (b) indicates the absorption spectrum in the case where the PCABPA was dissolved in a toluene solution. The light emission spectrum of the PCABPA is shown in FIG. 11. In FIG. 11, a horizontal axis represents a wavelength (nm) and a longitudinal axis represents the light emission intensity (given unit). A line (a) indicates the light emission spectrum (an excited wavelength: 352 nm) in the case where the PCABPA was a film form and a line (b) indicates the light emission spectrum (an excited wavelength: 390 nm) in the case where the PCABPA was dissolved in a toluene solution. According to FIG. 11, it is known that light emission from the PCABPA has a peak at 488 nm in the film form state and has a peak at 472 nm in the dissolved state in the toluene solution. These light emissions were recognized as blue light emissions.

When a film was formed by evaporation of the thus obtained PCABPA and an ionization potential of the compound in the thin film state was measured by using a photoelectron spectrometer (#AC-2, Riken Keiki Co., Ltd.), the ionization potential was 5.31 eV. An absorption spectrum of the compound in the thin film state was measured by using an UV and visible light spectrophotometer (#V-550, Japan Spectroscopy Corporation), and a wavelength of an absorption edge at a longer wavelength side of the absorption spectrum was set to be an energy gap (2.77 eV). Under these conditions, when the LUMO level was measured, it was −2.54 eV.

Further, when a decomposition temperature $T_d$ of the thus obtained PCABPA was measured by a thermo-gravimetric/differential thermal analyzer (#TG/DTA 320, Seiko Instruments Inc.), the $T_d$ was 485° C., and therefore, it was known that the PCABPA showed an excellent heat resistant property.

In addition, an oxidation reaction characteristic and a reduction reaction characteristic of the PCABPA were measured by a cyclic voltammetry (CV) measurement. Further, an electrochemical analyzer (#ALS model 600A, BAS Inc.) was used for the measurement.

In relation to a solution used in the CV measurement, dehydrated dimethylformamide (DMF) was used as a solvent. Tetraperchlorate-n-butylammonium (n-Bu$_4$NClO$_4$), which was a supporting electrolyte, was dissolved in the solvent such that the concentration of the tetraperchlorate-n-butylammonium was 100 mmol/L. Also, the PCABPA, which was an object to be measured, was dissolved such that the concentration thereof was set to be 1 mmol/L. Further, a platinum electrode (a PTE platinum electrode, BAS Inc.) was used as a work electrode. A platinum electrode (a VC-3 Pt counter electrode (5 cm), BAS Inc.) was used as an auxiliary electrode. An Ag/Ag+ electrode (an RE 5 non-aqueous reference electrode, BAS Inc.) was used as a reference electrode.

The oxidation reaction characteristic was measured as follows. After a potential of the work electrode with respect to the reference electrode was changed to 0.6 Thom −0.01 V, a scan for changing the potential to −0.01 V from 0.6 V was set as one cycle, and 100 cycle measurements were carried out. Further, the scanning speed of the CV measurement was set to be 0.1 V/s.

The reduction reaction characteristic was measured as follows. After a potential of the work electrode with respect to the reference electrode was changed to −2.7 V from −0.9 V, a scan for changing the potential to −0.9 V from −2.7 V was set as one cycle, and 100 cycle measurements were carried out. Further, the scanning speed of the CV measurement was set to be 0.1 V/s.

Figure 12A:
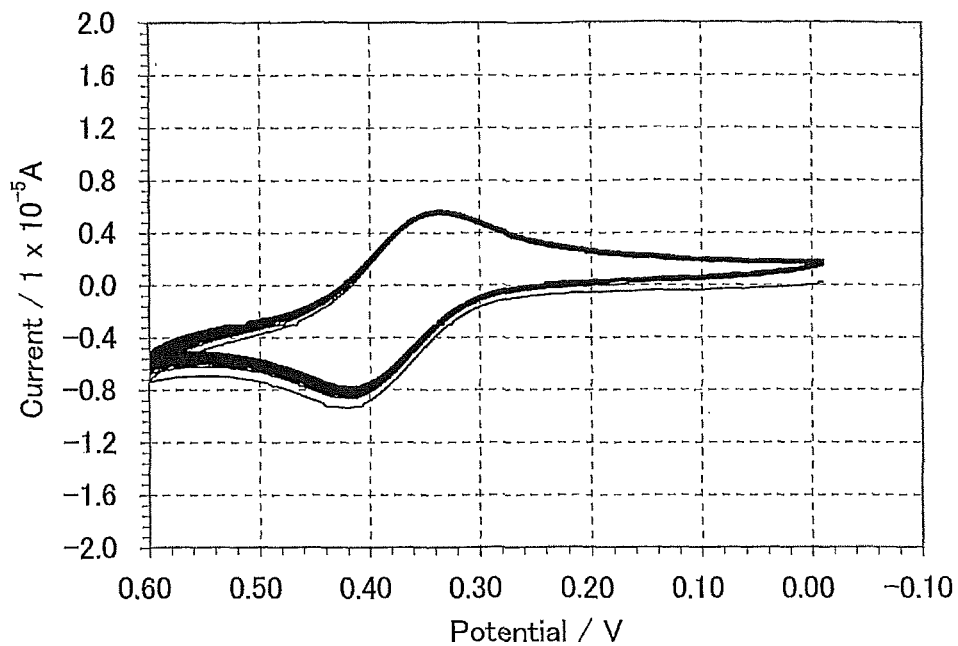
FIGS. 12A and 12B are graphs showing measurement results by cyclic voltammetry (CV) of an anthracene derivative of the present invention.
Figure 12B:
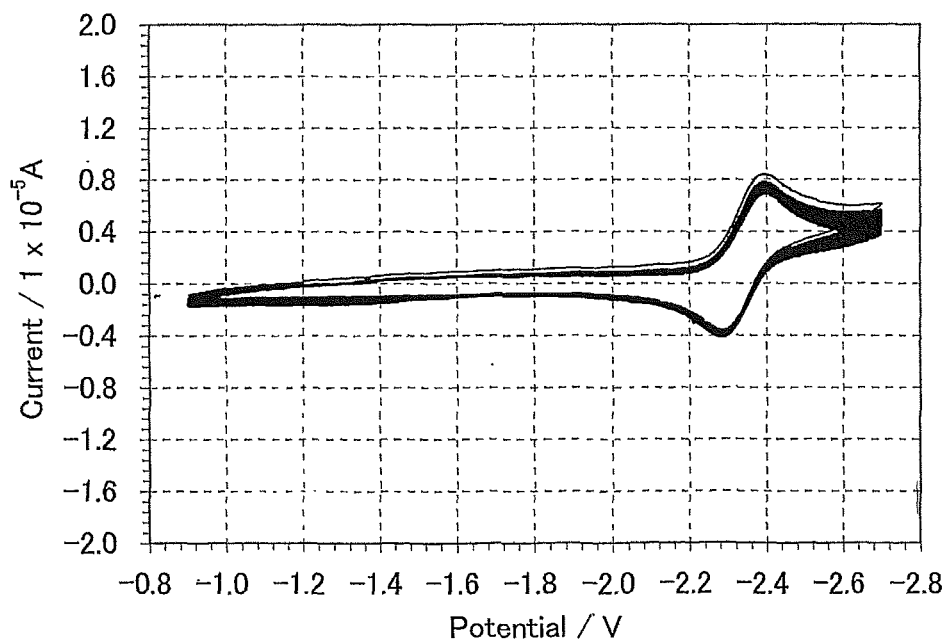

Results of measuring the oxidation reaction characteristic of the PCABPA are shown in FIG. 12A. Also, results of measuring the reduction reaction characteristic of the PCABPA are shown in FIG. 12B. In each of FIGS. 12A and 12B, a horizontal axis represents a potential (V) of the work electrode with respect to the reference electrode, while a longitudinal axis represents an amount of current flowing between the work electrode and the auxiliary electrode ($1 \times 10^{-5}$ A).

According to FIG. 12A, it was known that an oxidation potential was 0.42 V (vs. Ag/Ag$^+$ electrode). According to FIG. 12B, it was known that a reduction potential was −2.39 V (vs. Ag/Ag$^+$ electrode). Although the scan was repeated 100 times, a peak position and a peak intensity of a CV curve were hardly changed in each of the oxidation reaction and the reduction reaction. Thus, it was known that the PCABPA, which was one of compounds of the present invention, was absolutely stable with respect to the repetition of the oxidation reaction. In addition, it was also known that the PCABPA was absolutely stable with respect to the repetition of the reduction reaction.

SYNTHETIC EXAMPLE 2

A method for synthesizing 9,10-bis{4'-[N-(9-phenylcarbazole-3-yl)-N-phenylamino] biphenyl-4-yl}-2-tert-butylanthracene (abbreviation: PCABBA), which is an anthracene derivative represented by the structural formula (13), will be described in Synthetic Example 2.

[Step 1]

Firstly, a method for synthesizing 9,10-bis(4'-bromobiphenyl-4-yl)-2-tert-butylanthracene will be described.

Specifically, 655 g (21.0 mmol) of 4,4'-dibromobiphenyl was poured in a three-neck flask (500 ml), and nitrogen was substituted for air in the three-neck flask. Next, 200 ml of tetrahydrofuran was added thereto. The mixture was cooled to −80° C., and then 14.5 ml (22.3 mmol) of n-butyllithium (1.54 mol/L of a hexane solution) was dropped therein and the mixture was stirred for one hour while keeping the temperature at −80° C. While still keeping the temperature at −80° C., a mixed solution, in which 2.07 g (10.0 mmol) of anthraquinone was suspended in 20 ml of tetrahydrofuran (abbreviation: THF), was dropped in the reaction solution. After the termination of the dropping, the mixture was further stirred for two hours while the temperature was increased to the room temperature from −80° C. After the reaction, 110 ml of ethanol was added to the product and then stirred. Subsequently, the reaction solution was washed with water and saturated saline, and then, dried with magnesium sulfate. The reaction mixture was naturally filtered and the filtrate was concentrated to obtain a light yellow solid (a synthetic scheme (e-1)).

The thus obtained light yellow solid, 6.64 g (40 mmol) of potassium iodide, 12.7 g (120 mmol) of sodium phosphine acid monohydrate, and 120 ml of glacial acetic acid were poured in an eggplant-type flask, which was a container with a volume capacity of 500 ml. The mixture were refluxed for two hours. After the reaction, a temperature of the product was cooled to the room temperature, and then, the precipitated solid was collected by suction filtration. The solid was recrystallized from dichloromethane-ethanol to obtain 3.43 g (the yield: 51%) of a light yellow solid of 9, 10-bis(4'-bromobiphenyl-4-yl)-2-tert-butylanthracene, which was an object matter (a synthetic scheme (e-2)).

Further, the synthetic schemes (e-1) and (e-2) of the Step 1 are shown below.

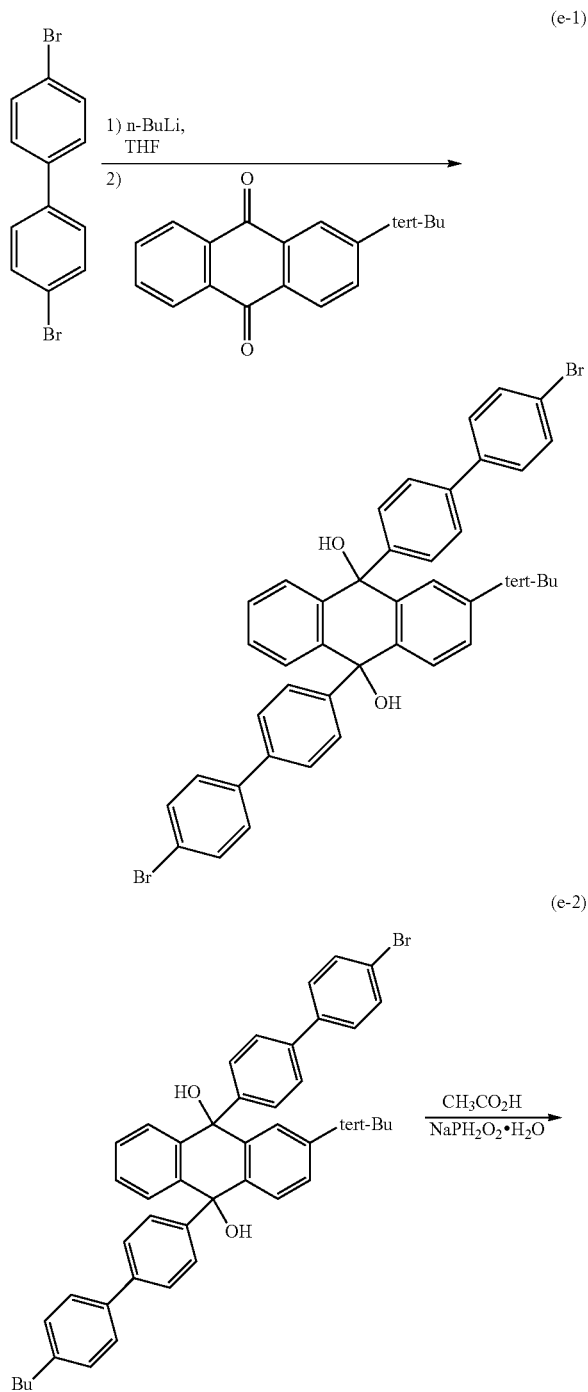

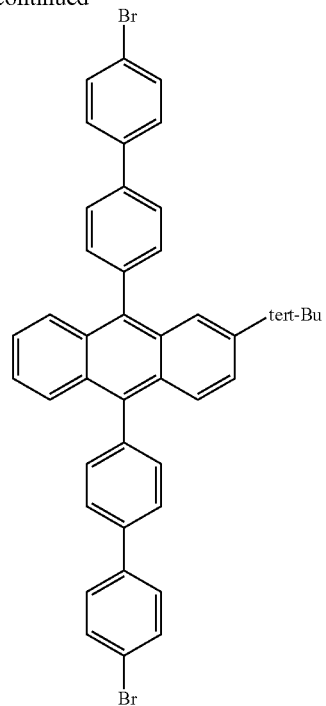

[Step 2]

Next, a method for synthesizing 9,10-bis-{4'-[N-(9-phenylcarbazole-3-yl)-N-phenylamine] biphenyl-4-yl}-2-tert-butylanthracene, which is represented by the structural formula (13), will be described.

Specifically, 700 mg (1.0 mmol) of the 9,10-bis(4'-bromobiphenyl-4-yl)-2-tert-butylanthracene, which was obtained in the Step 1 of Synthetic Example 2, 670 mg (2.0 mmol) of the 3-(N-phenylamino)-9-phenylcarbazole (abbreviation: PCA), which was obtained in the Step 2 of Synthetic Example 1, 60 mg (0.10 mmol) of bis(dibenzylideneacetone) palladium (0), 1.0 ml (0.50 mmol) of tri-tert-butylphosphine (a 10 wt % hexane solution), and 0.4 g (4:0 mmol) of sodium-tert-butoxide were poured in a flask, 10 ml of dehydrated xylene was added thereto, and nitrogen was substituted for air in the flask. The mixture was stirred while heating at 120° C. for six hours under nitrogen atmosphere. After the reaction, about 200 ml of toluene was added to the suspension. The mixture was filtered through florisil and celite. The thus obtained filtrate was concentrated and a target matter was obtained by a silica gel chromatography (toluene:hexane=1:1). The target matter was concentrated and the thus obtained residue was recrystallized by being irradiated with supersonic to obtain 70 mg (the yield: 6%) of a beige powder of 9,10-bis{4'-[N-(9-phenylcarbazole-3-yl)-N-phenylamino] biphenyl-4-yl}-2-tert-butylanthracene (abbreviation: PCABBA), which was a target matter.

Also, a synthetic scheme (f-1) of the Step 2 is shown below.

(f-1)

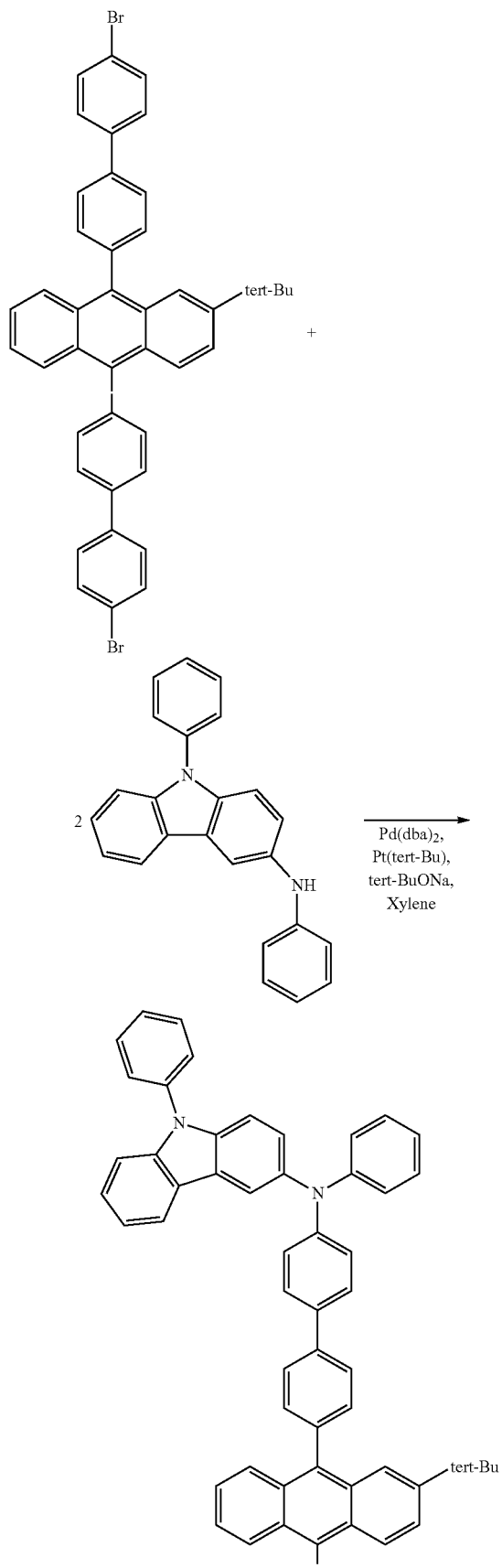

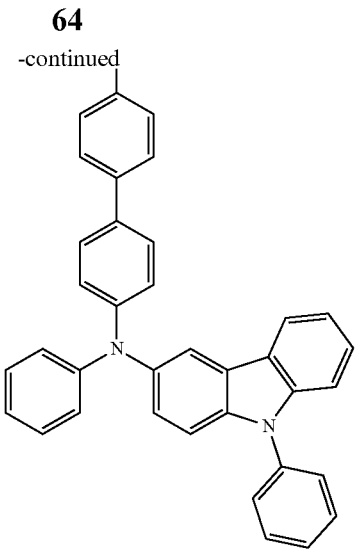

Figure 47A:
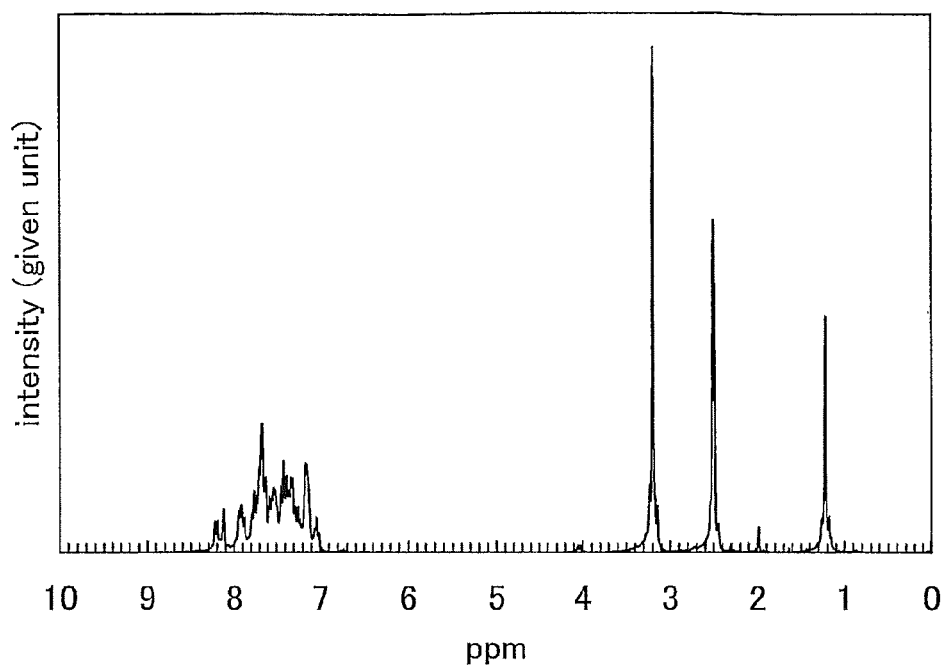
FIGS. 47A and 47B are $^1$H-NMR charts of PCABBA synthesized in Synthetic Example 2.
Figure 47B:
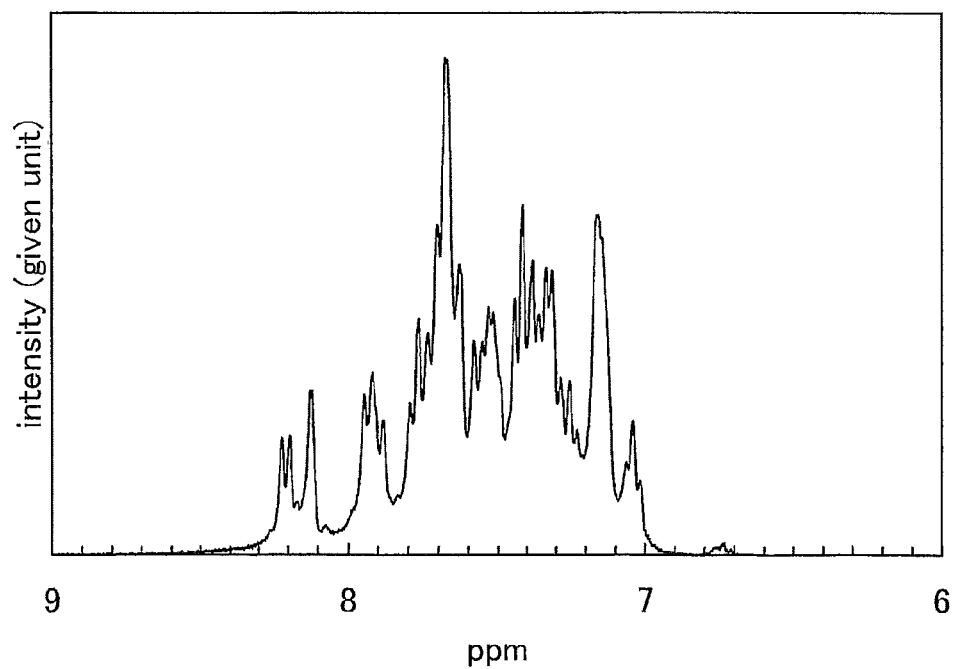

Results of a ¹H-NMR analysis are shown below. Also, ¹H-NMR charts are shown in FIGS. 47A and 47B. Further, FIG. 47B is a chart showing an enlarged portion in the range of 9 ppm to 6 ppm of FIG. 47A.

The ¹H-NMR (300 MHz, DMSO-d): δ=1.22 (s, 9H), 7.04 (t, J=6.9 Hz, 2H), 7.14-7.79 (m, 39H), 7.88-7.94 (m, 4H), 8.12 (d, J=1.5 Hz, 2H), and 8.20 (d, J=8.4 Hz, 2H).

Figure 48:
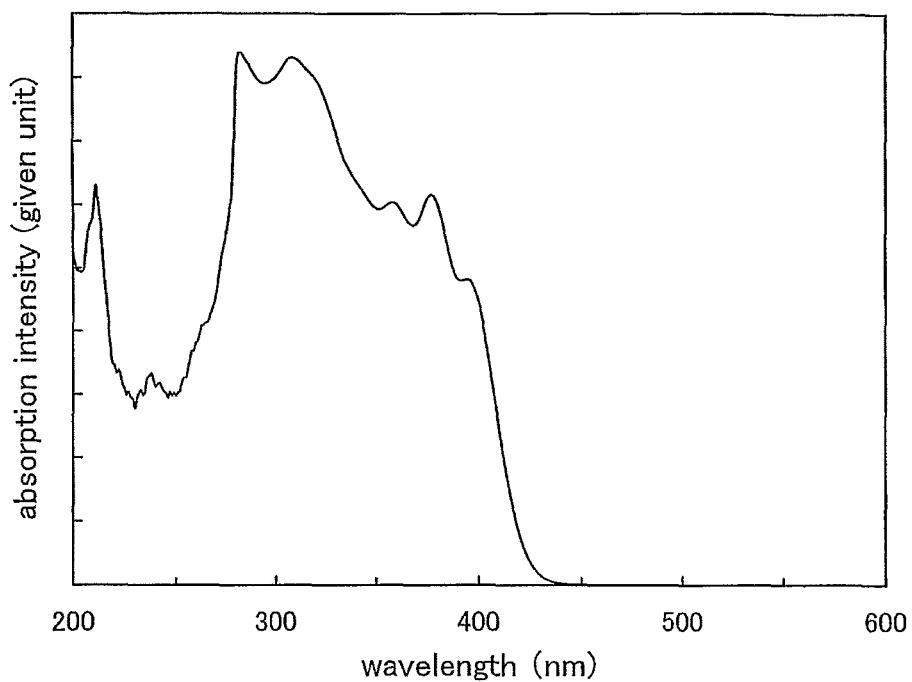
FIG. 48 is a graph showing an absorption spectrum of an anthracene derivative of the present invention.
Figure 49:
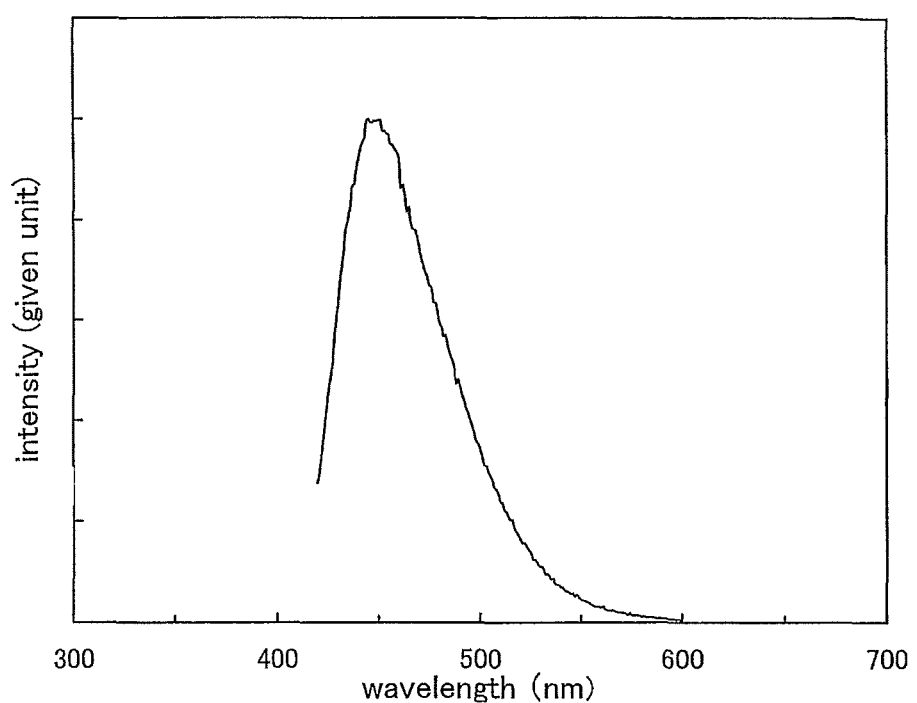
FIG. 49 is a graph showing a light emission spectrum of an anthracene derivative of the present invention.

Further, an absorption spectrum of the PCABBA in a toluene solution is shown in FIG. 48. In FIG. 48, a horizontal axis represents a wavelength (nm) and a longitudinal axis represents absorption intensity (given unit). Also, a light emission spectrum of the PCABBA in a toluene solution is shown in FIG. 49. In FIG. 49, a horizontal axis represents a wavelength (nm) and a longitudinal axis represents light emission intensity (given unit). According to FIG. 49, it Was known that the light emission of the PCABBA had a peak at 445 nm in the toluene solution, and it was recognized that the light emission was blue. Therefore, it was known that the PCABBA was a suitable substance as a light emitting substance emitting blue light.

[Embodiment 2]

A method for manufacturing a light emitting element that uses the PCABPA synthesized in Synthetic Example 1 as a light emitting substance and an operational characteristic of the light emitting element will be described in this embodiment.

Figure 15:
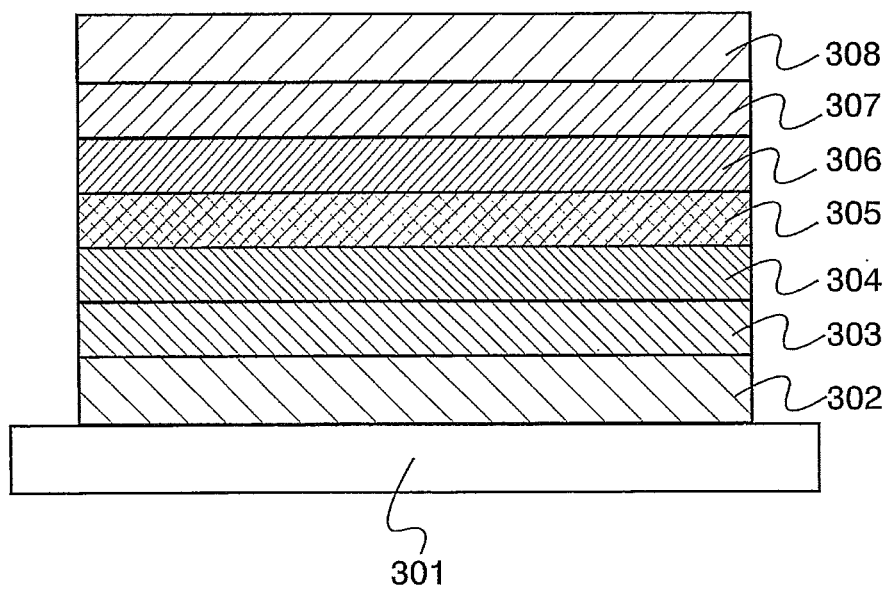
FIG. 15 is a cross sectional view explaining a light emitting element manufactured in an embodiment.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to 1×10⁻⁴ Pa. Then, a first layer 303 including copper phthalocyanine was formed on the first electrode 302 by evaporation. The thickness of the first layer 303 was set to be 20 nm. The first layer 303 serves as a hole injecting layer when the light emitting element is operated.

Subsequently, a second layer 304 including NPB was formed on the first layer 303 by evaporation. The thickness of the second layer 304 was set to be 40 nm. The second layer 304 serves as a hole transporting layer when the light emitting element is operated.

A third layer 305 including t-BuDNA and PCABPA was formed on the second layer 304 by co-evaporation. The thickness of the third layer 305 was set to be 40 nm. The mass ratio between t-BuDNA and PCABPA was adjusted to be 1:0.05. Thus, the PCABPA was dispersed in the t-BuDNA. The third layer 305 serves as a light emitting layer when the light emitting element is operated. Further, the PCABPA serves as a light emitting substance.

Next, a fourth layer 306 including $Alq_3$ was formed on the third layer 305 by evaporation. The thickness of the fourth layer 306 was set to be 20 nm. The fourth layer 306 serves as an electron transporting layer when the light emitting element is operated.

A fifth layer 307 including calcium fluoride was formed on the fourth layer 306 by evaporation. The thickness of the fifth layer 307 was set to be 1 nm. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at room temperature (under an atmosphere where a temperature was maintained at 25° C.).

Figure 16:
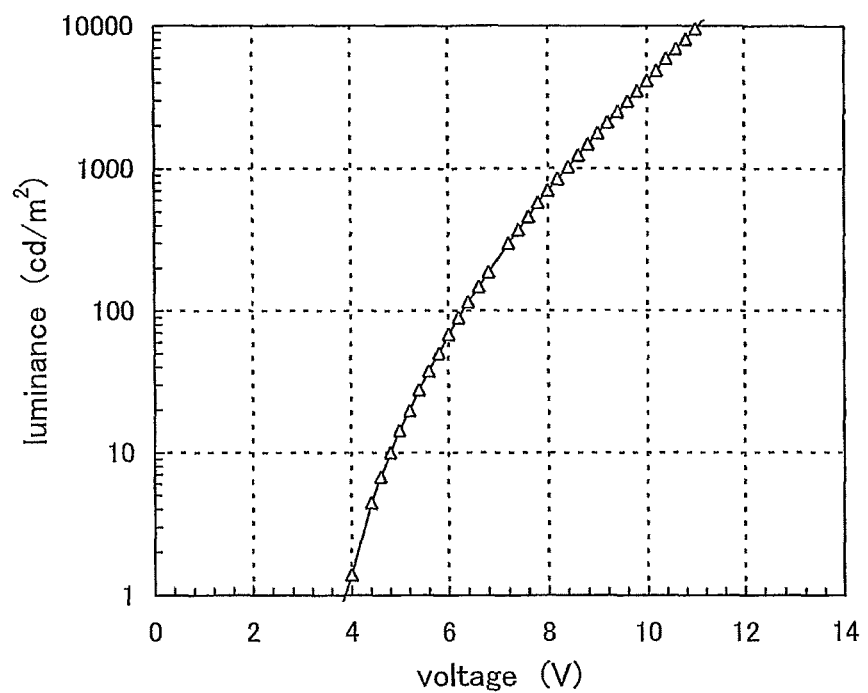
FIG. 16 is a graph showing a luminance-voltage characteristic of a light emitting element manufactured in Embodiment 2.
Figure 17:
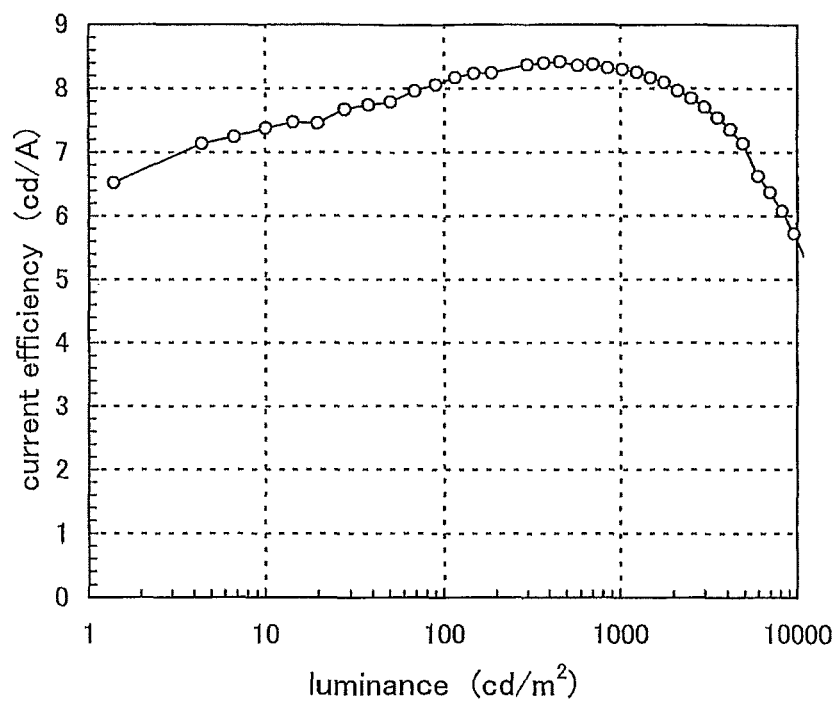
FIG. 17 is a graph showing a luminance-current efficiency characteristic of a light emitting element manufactured in Embodiment 2.

Measurement results are shown in FIG. 16 and FIG. 17. FIG. 16 shows a measurement result of a voltage-luminance characteristic whereas FIG. 17 shows a measurement result of a luminance-current efficiency characteristic. In FIG. 16, a horizontal axis represents the voltage (V) and a longitudinal axis represents the luminance ($cd/m^2$). Also, in FIG. 17, a horizontal axis represents the luminance ($cd/m^2$) and a longitudinal axis represents the current efficiency (cd/A).

Figure 18:
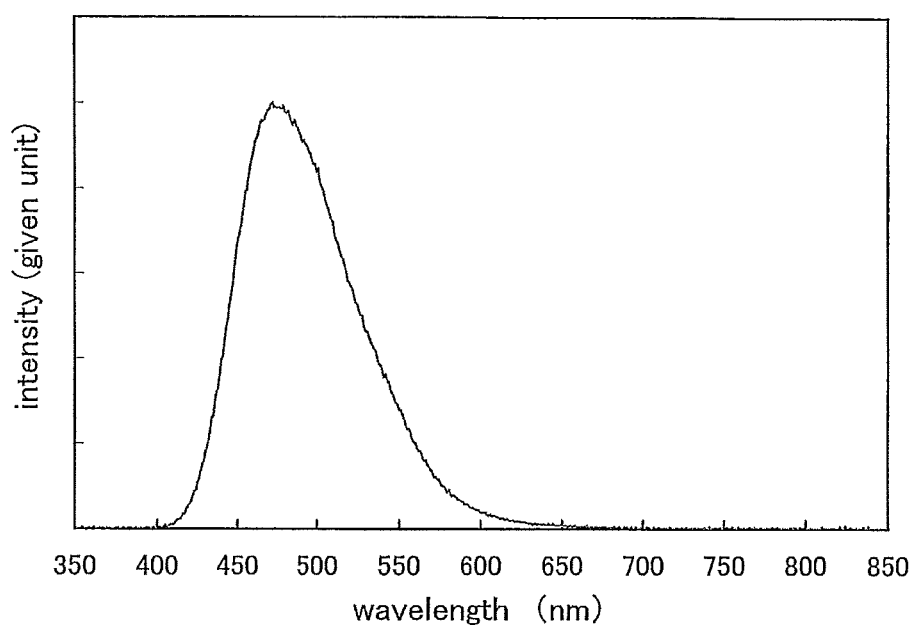
FIG. 18 is a graph showing a light emission spectrum of a light emitting element manufactured in Embodiment 2.

The light emission spectrum of the light emitting element manufactured in this embodiment is shown in FIG. 18. In FIG. 18, a horizontal axis represents a wavelength (nm) and a longitudinal axis represents the intensity (given unit). According to FIG. 18, it was known that the light emitting element of the present embodiment had a peak of light emission spectrum at 477 nm, and emitted blue light. Moreover, the CIE chromaticity coordinates were x=0.16, y=0.28. As a consequence, it was known that the light emitting element of the present embodiment emitted blue light with good color purity.

[Embodiment 3]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1 \times 10^{-4}$ Pa. Then, a first layer 303 including copper phthalocyanine was formed on the first electrode 302 by evaporation. The thickness of the first layer 303 was set to be 20 nm. The first layer 303 serves as a hole injecting layer when the light emitting element is operated.

Subsequently, a second layer 304 including 4,4'-bis[N-(4-biphenylyl)-N-phenylamino] biphenyl (abbreviation: BBPB) was formed on the first layer 303 by evaporation. The thickness of the second layer 304 was set to be 40 nm. The second layer 304 serves as a hole transporting layer when the light emitting element is operated.

A third layer 305 including t-BuDNA and PCABPA was formed on the second layer 304 by co-evaporation. The thickness of the third layer 305 was set to be 40 nm. The mass ratio between t-BuDNA and PCABPA was adjusted to be 1:0.05. Thus, the PCABPA was dispersed in the t-BuDNA. The third layer 305 serves as a light emitting layer when the light emitting element is operated. Further, the PCABPA serves as a light emitting substance.

Next, a fourth layer 306 including $Alq_3$ was formed on the third layer 305 by evaporation. The thickness of the fourth layer 306 was set to be 20 nm. The fourth layer 306 serves as an electron transporting layer when the light emitting element is operated.

A fifth layer 307 including calcium fluoride was formed on the fourth layer 306 by evaporation. The thickness of the fifth layer 307 was set to be 1 nm. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at room temperature (under an atmosphere where a temperature was maintained at 25° C.).

Figure 19:
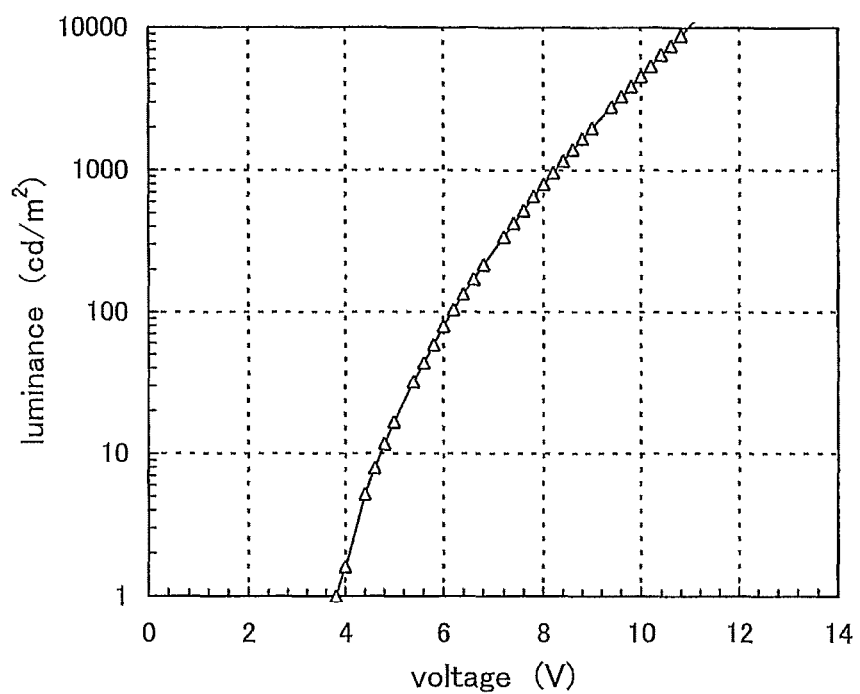
FIG. 19 is a graph showing a luminance-voltage characteristic of a light emitting element manufactured in Embodiment 3.
Figure 20:
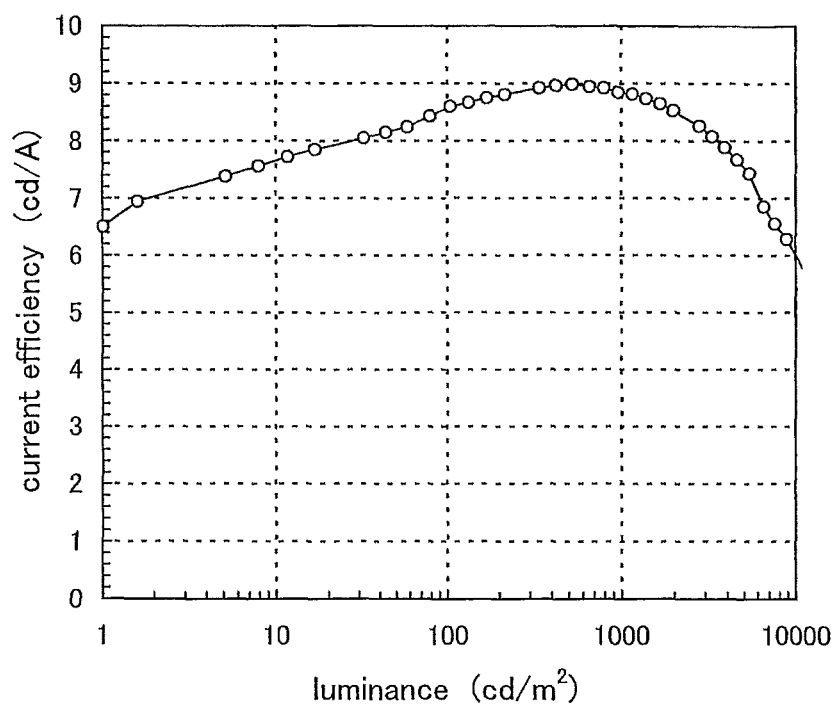
FIG. 20 is a graph showing a luminance-current efficiency characteristic of a light emitting element manufacturing in Embodiment 3.

Measurement results are shown in FIG. 19 and FIG. 20. FIG. 19 shows a measurement result of a voltage-luminance characteristic whereas FIG. 20 shows a measurement result of a luminance-current efficiency characteristic. In FIG. 19, a horizontal axis represents the voltage (V) and a longitudinal axis represents the luminance ($cd/m^2$). Also, in FIG. 20, a horizontal axis represents the luminance ($cd/m^2$) and a longitudinal axis represents the current efficiency (cd/A).

Figure 21:
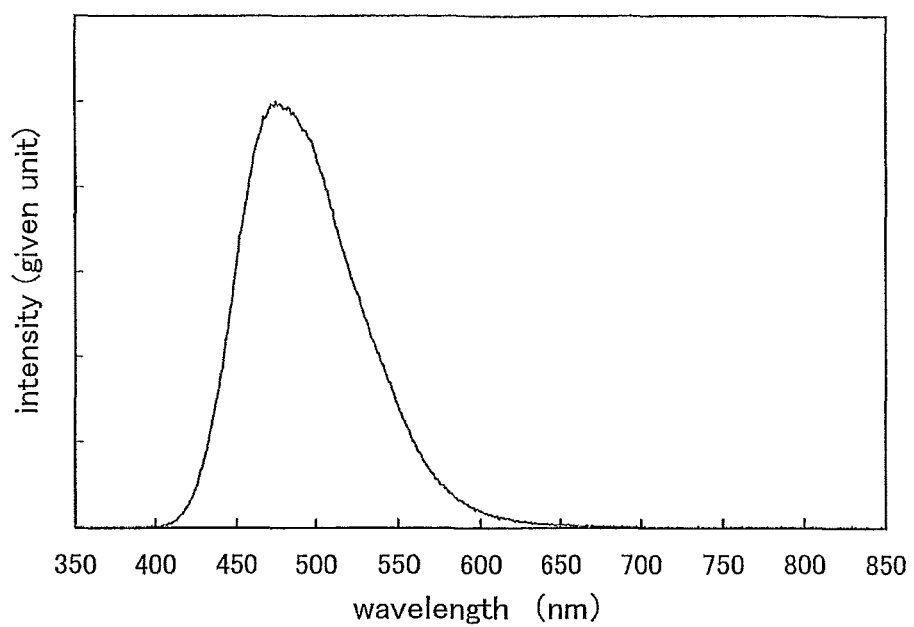
FIG. 21 is a graph showing a light emission spectrum of a light emitting element manufactured in Embodiment 3.

The light emission spectrum of the light emitting element manufactured in this embodiment is shown in FIG. 21. In FIG. 21, a horizontal axis represents a wavelength (nm) and a longitudinal axis represents the intensity (given unit). According to FIG. 21, it was known that the light emitting element of the present embodiment had a peak of light emission spectrum at 479 nm, and emitted blue light. Moreover, the CIE chromaticity coordinates were x=0.16, y=0.29. As a consequence, it was known that the light emitting element of the present embodiment emits blue light with good color purity.

[Embodiment 4]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further; the first electrode was formed to have a square shape having the size of 2 mm×2 mm.

Next, the glass substrate 301 over which the first electrode 302 was formed was flied to a holder provided in a vacuum evaporation apparatus.

The inside of the vacuum evaporation apparatus was evacuated so that the pressure was reduced to $1 \times 10^{-4}$ Pa. Then, a first layer 303 including copper phthalocyanine was formed on the first electrode 302 by evaporation. The thickness of the first layer 303 was set to be 20 nm. The first layer 303 serves as a hole injecting layer when the light emitting element is operated.

Subsequently, a second layer 304 including BSPB was formed on the first layer 303 by evaporation. The thickness of the second layer 304 was set to be 40 nm. The second layer 304 serves as a hole transporting layer when the light emitting element is operated.

A third layer 305 including t-BuDNA and PCABPA was formed on the second layer 304 by co-evaporation. The thickness of the third layer 305 was set to be 40 nm. The mass ratio between t-BuDNA and PCABPA was adjusted to be 1:0.1. Thus, the PCABPA was dispersed in the t-BuDNA. The third layer 305 serves as a light emitting layer when the light emitting element is operated. Further, the PCABPA serves as a light emitting substance.

Next, a fourth layer 306 including $Alq_3$ was formed on the third layer 305 by evaporation. The thickness of the fourth layer 306 was set to be 20 nm. The fourth layer 306 serves as an electron transporting layer when the light emitting element is operated.

A fifth layer 307 including calcium fluoride was formed on the fourth layer 306 by evaporation. The thickness of the fifth layer 307 was set to be 1 nm. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where, a temperature was maintained at 25° C.).

Figure 22:
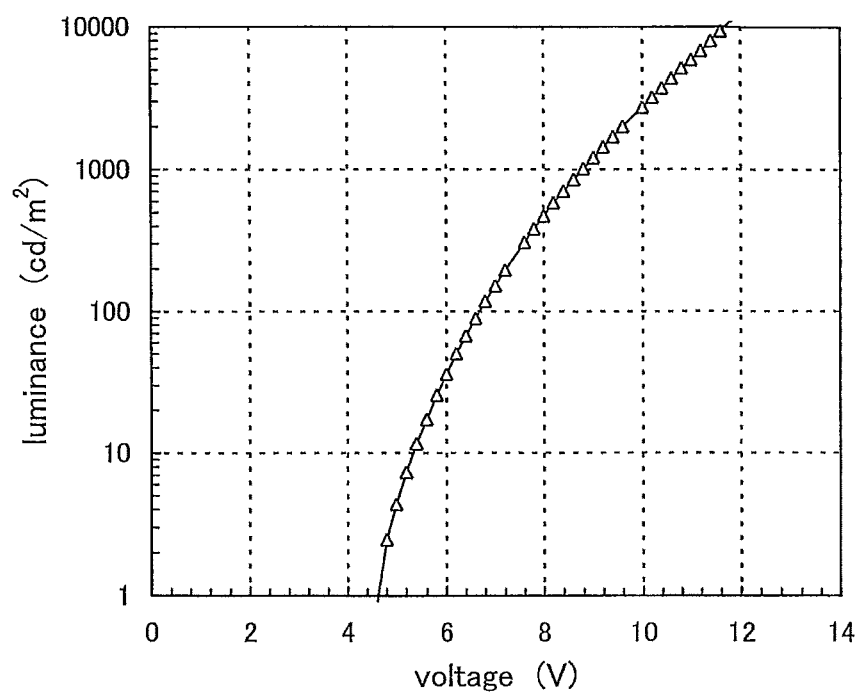
FIG. 22 is a graph showing a luminance-voltage characteristic of a light emitting element manufactured in Embodiment 4.
Figure 23:
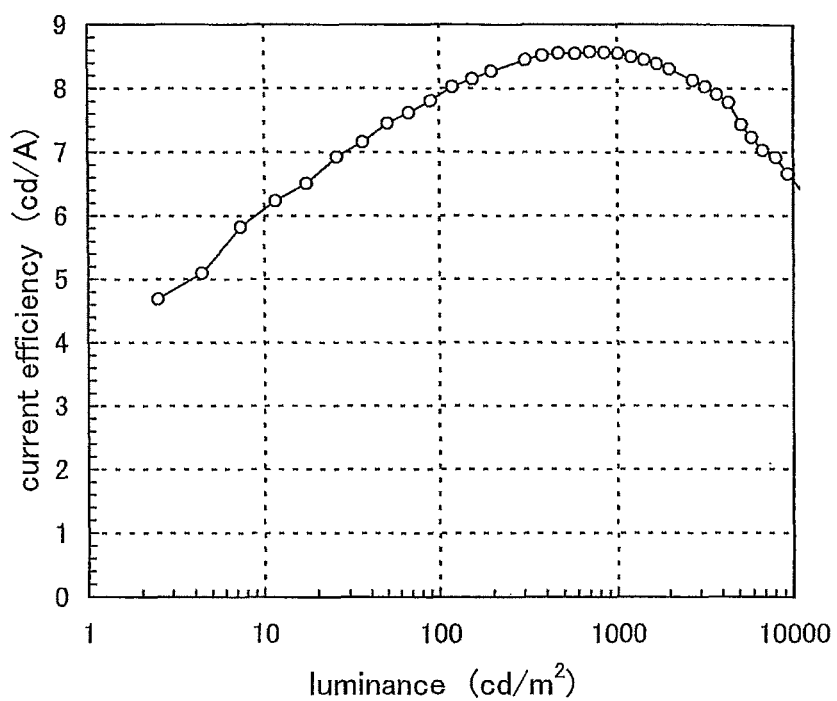
FIG. 23 is a graph showing a luminance-current efficiency characteristic of a light emitting element manufactured in Embodiment 4.

Measurement results are shown in FIG. 22 and FIG. 23. FIG. 22 shows a measurement result of a voltage-luminance characteristic, whereas FIG. 23 shows a measurement result of a luminance-current efficiency characteristic. In FIG. 22, a horizontal axis represents the voltage (V) and a longitudinal axis represents the luminance ($cd/m^2$). Also, in FIG. 23, a horizontal axis represents the luminance ($cd/m^2$) and a longitudinal axis represents the current efficiency (cd/A).

Figure 24:
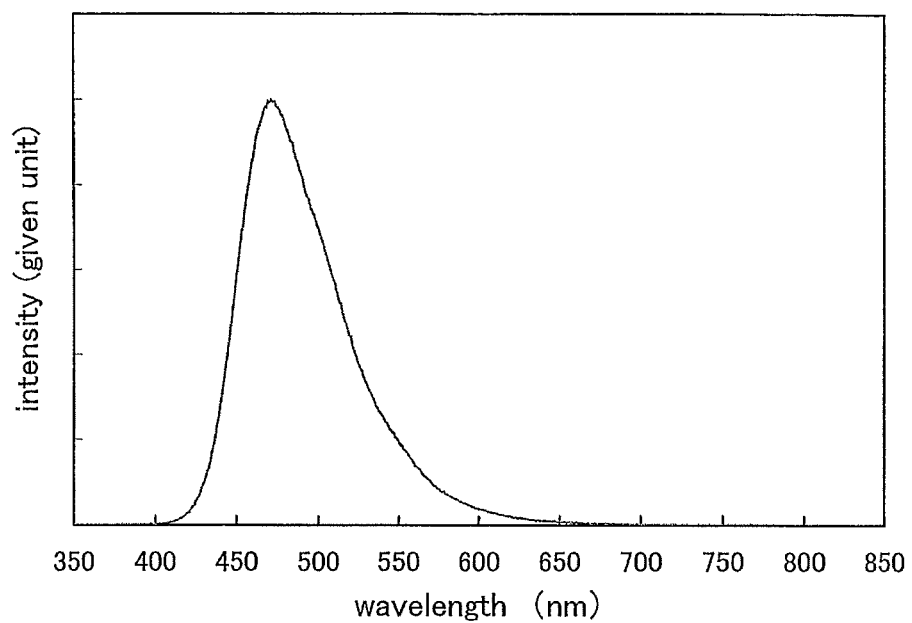
FIG. 24 is a graph showing a light emission spectrum of a light emitting element manufactured in Embodiment 4.

The light emission spectrum of the light emitting element manufactured in this embodiment is shown in FIG. 24. In FIG. 24, a horizontal axis represents a wavelength (nm) and a longitudinal axis represents the intensity (given unit). According to FIG. 24, it was known that the light emitting element of the present embodiment had a peak of light emission spectrum at 474 nm, and emitted blue light. Moreover, the CIE chromaticity coordinates were x=0.16, y=0.25. As a consequence, it was known that the light emitting element of the present embodiment emitted blue light with good color purity.

[Embodiment 5]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1 \times 10^{-4}$ Pa. Then, a first layer 303 including DNTPD was formed on the first electrode 302 by evaporation. The thickness of the first layer 303 was set to be 50 nm. The first layer 303 serves as a hole injecting layer when the light emitting element is operated.

Subsequently, a second layer 304 including NPB was formed on the first layer 303 by evaporation. The thickness of the second layer 304 was set to be 10 nm. The second layer 304 serves as a hole transporting layer when the light emitting element is operated.

A third layer 305 including CzPA and PCABPA was formed on the second layer 304 by co-evaporation. The thickness of the third layer 305 was set to be 40 nm. The mass ratio between CzPA and PCABPA was adjusted to be 1:0.05. Thus, the PCABPA was dispersed in the CzPA. The third layer 305 serves as a light emitting layer when the light emitting element is operated. Further, the PCABPA serves as a light emitting substance.

Next, a fourth layer 306 including Alq$_3$ was formed on the third layer 305 by evaporation. The thickness of the fourth layer 306 was set to be 20 nm. The fourth layer 306 serves as an electron transporting layer when the light emitting element is operated.

A fifth layer 307 including calcium fluoride was formed on the fourth layer 306 by evaporation. The thickness of the fifth layer 307 was set to be 1 nm. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where a temperature was maintained at 25° C.).

Figure 25:
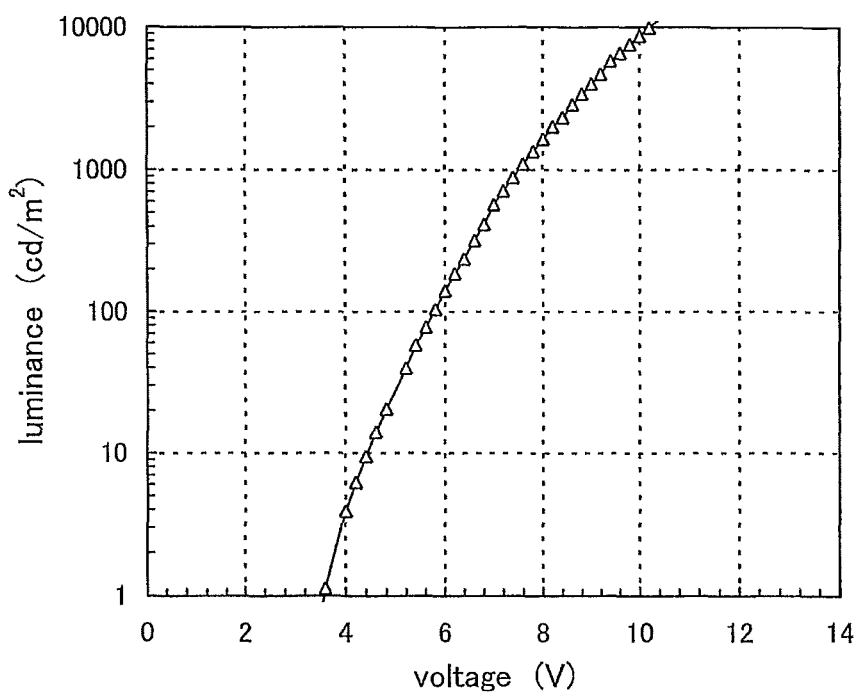
FIG. 25 is a graph showing a luminance-voltage characteristic of a light emitting element manufacturing in Embodiment 5.
Figure 26:
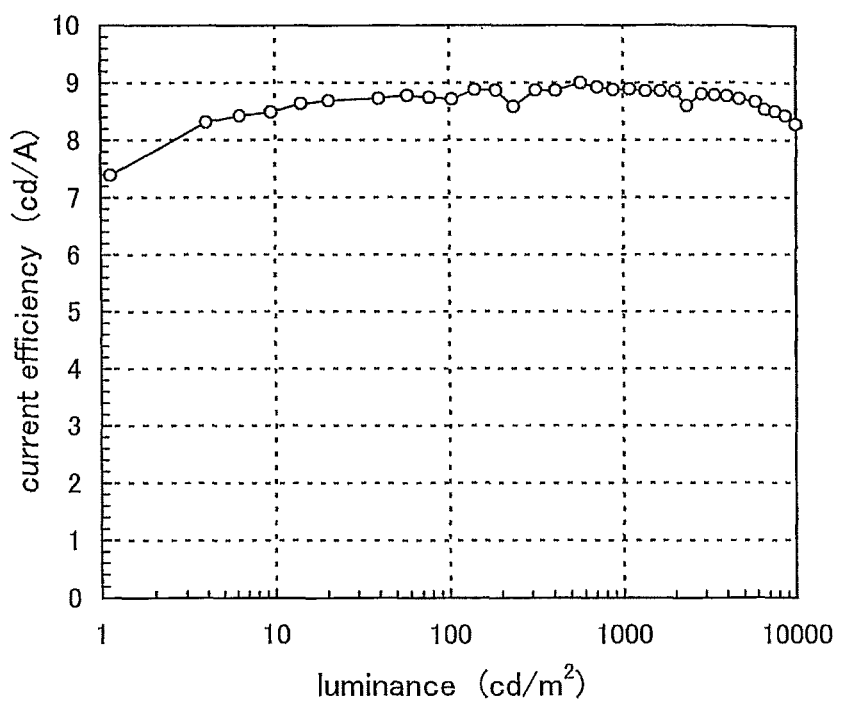
FIG. 26 is a graph showing a luminance-current efficiency characteristic of a light emitting element manufacturing in Embodiment 5.

Measurement results are shown in FIG. 25 and FIG. 26. FIG. 25 shows a measurement result of a voltage-luminance characteristic, whereas FIG. 26 shows a measurement result of a luminance-current efficiency characteristic. In FIG. 25, a horizontal axis represents the voltage (V) and a longitudinal axis represents the luminance (cd/m$^2$). Also, in FIG. 26, a horizontal axis represents the luminance (cd/m$^2$) and a longitudinal axis represents the current efficiency (cd/A).

Figure 27:
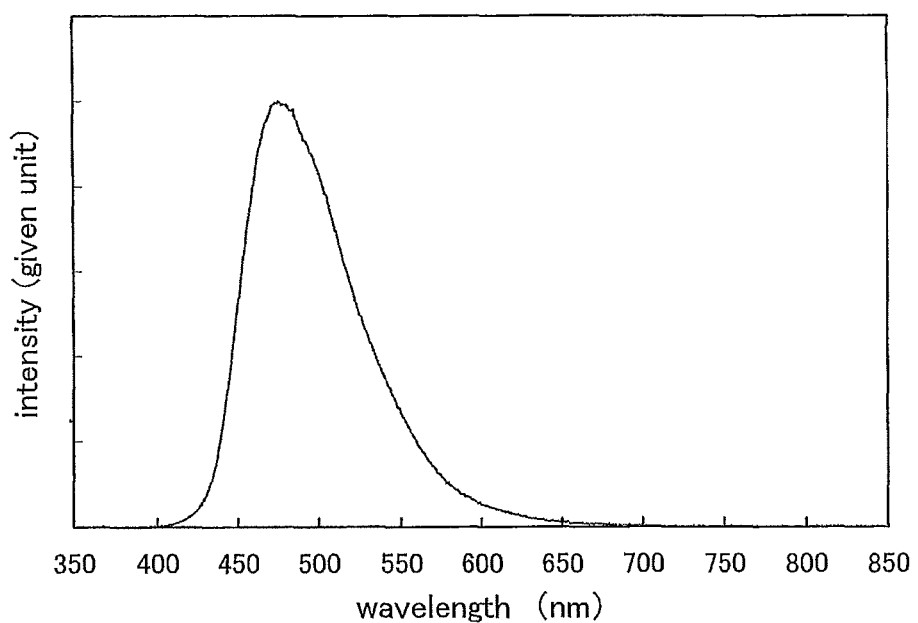
FIG. 27 is a graph showing a light emission spectrum of a light emitting element manufactured in Embodiment 5.

The light emission spectrum of the light emitting element manufactured in this embodiment is shown in FIG. 27. In FIG. 27, a horizontal axis represents a wavelength (nm) and a longitudinal axis represents the intensity (given unit). According to FIG. 27, it was known that the light emitting element of the present embodiment had a peak of light emission spectrum at 478 nm, and emitted blue light. Moreover, the CIE chromaticity coordinates were x=0.16, y=0.28. As a consequence, it was known that the light emitting element of the present embodiment emitted blue light with good color purity.

[Embodiment 6]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to 1×10$^{-4}$ Pa. Then, a first layer 303 including DNTPD was formed on the first electrode 302 by evaporation. The thickness of the first layer 303 was set to be 50 nm. The first layer 303 serves as a hole injecting layer when the light emitting element is operated.

Subsequently, a second layer 304 including NPB was formed on the first layer 303 by evaporation. The thickness of the second layer 304 was set to be 10 nm. The second layer 304 serves as a hole transporting layer when the light emitting element is operated.

A third layer 305 including CzPA and PCABPA was formed on the second layer 304 by co-evaporation. The thickness of the third layer 305 was set to be 40 nm. The mass ratio between CzPA and PCABPA was adjusted to be 1:0.04. Thus, the PCABPA was dispersed in the CzPA. The third layer 305 serves as a light emitting layer when the light emitting element is operated. Further, the PCABPA serves as a light emitting substance.

Next, a fourth layer 306 including Alq$_3$ was formed on the third layer 305 by evaporation. The thickness of the fourth layer 306 was set to be 10 nm. The fourth layer 306 serves as an electron transporting layer when the light emitting element is operated.

A fifth layer 307 including Alq$_3$ and Li was formed on the fourth layer 306 by co-evaporation. The thickness of the fifth layer 307 was set to be 10 nm. The mass ratio between Alq$_3$ and Li was adjusted to be 1:0.01. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where a temperature was maintained at 25° C.).

Figure 28:
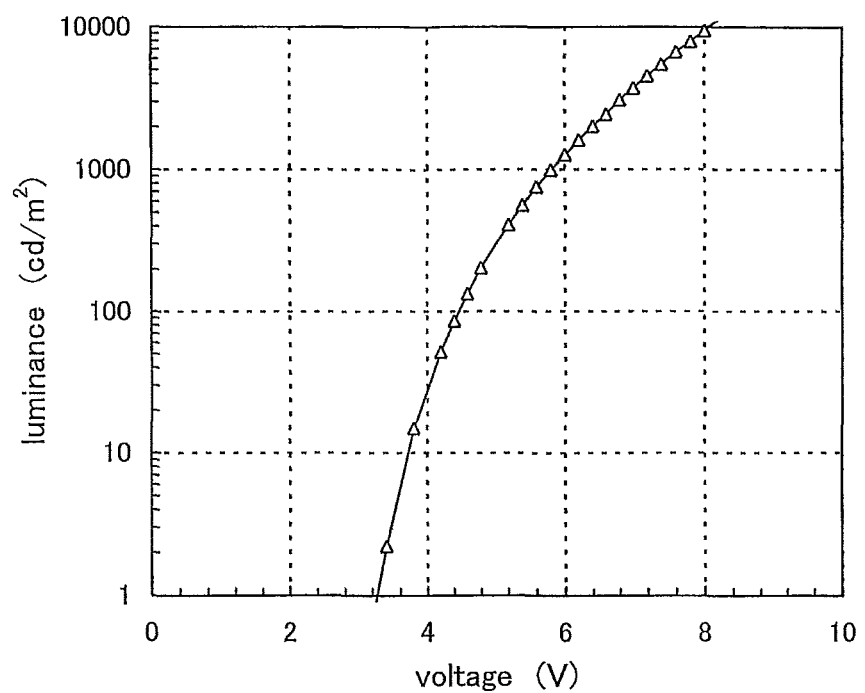
FIG. 28 is a graph showing a luminance-voltage characteristic of a light emitting element manufacturing in Embodiment 6.
Figure 29:
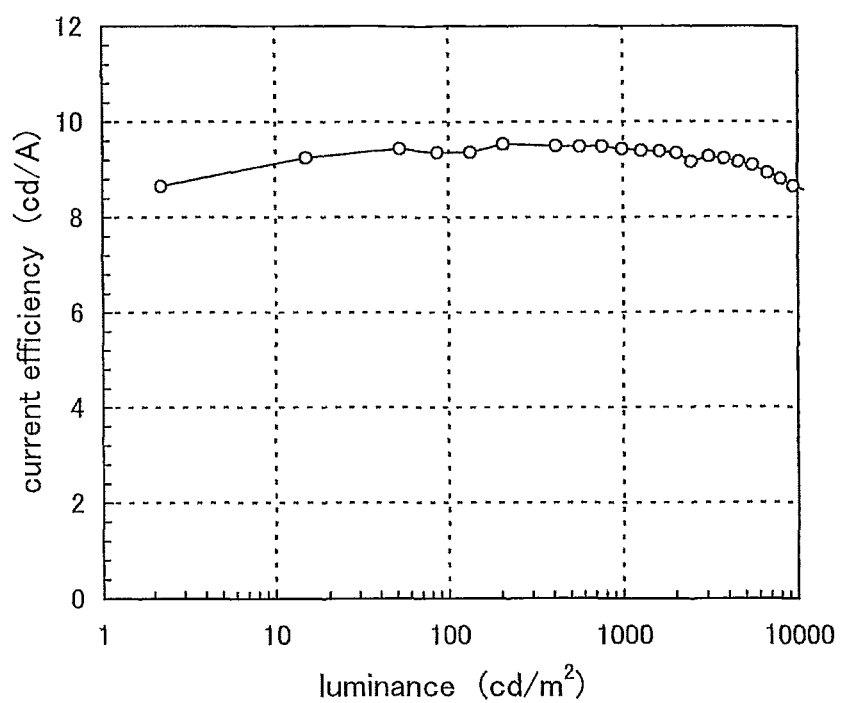
FIG. 29 is a graph showing a luminance-current efficiency characteristic of a light emitting element manufacturing in Embodiment 6.

Measurement results are shown in FIG. 28 and FIG. 29. FIG. 28 shows a measurement result of a voltage-luminance characteristic, whereas FIG. 29 shows a measurement result of a luminance-current efficiency characteristic. In FIG. 28, a horizontal axis represents the voltage (V) and a longitudinal axis represents the luminance (cd/m$^2$). Also, in FIG. 29, a horizontal axis represents the luminance (cd/m$^2$) and a longitudinal axis represents the current efficiency (cd/A).

Figure 30:
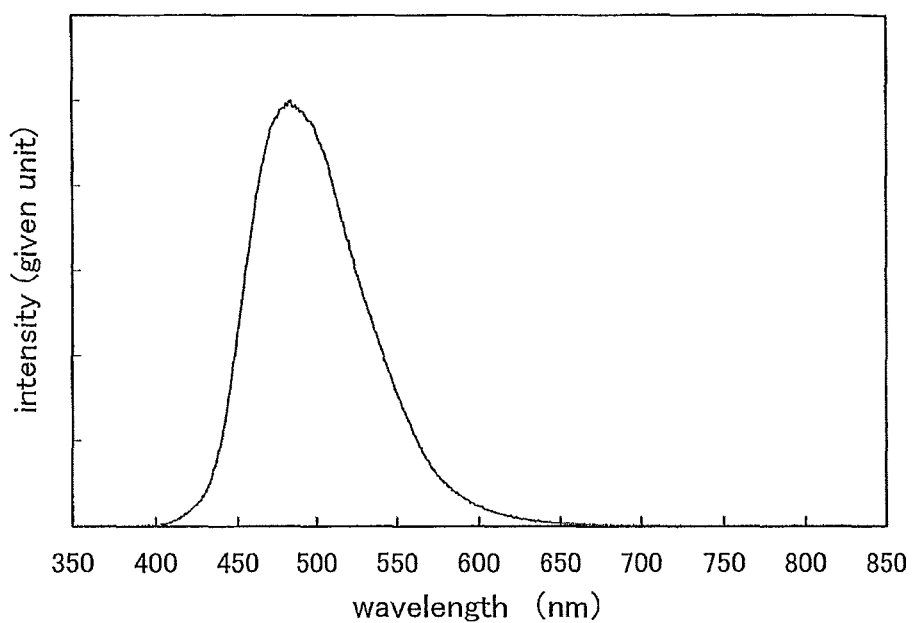
FIG. 30 is a graph showing a light emission spectrum of a light emitting element manufactured in Embodiment 6.

The light emission spectrum of the light emitting element manufactured in this embodiment is shown in FIG. 30. In FIG. 30, a horizontal axis represents a wavelength (nm) and a longitudinal axis represents the intensity (given unit). According to FIG. 30, it was known that the light emitting element of the present embodiment had a peak of light emission spectrum at 487 nm, and emitted blue light. Moreover, the CIE chromaticity coordinates were x=0.17, y=0.32. Consequently, it was known that the light emitting element of the present embodiment emitted blue light with good color purity.

[Embodiment 7]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1 \times 10^{-4}$ Pa. Then, a first layer 303 including DNTPD was formed on the first electrode 302 by evaporation. The thickness of the first layer 303 was set to be 50 nm. The first layer 303 serves as a hole injecting layer when the light emitting element is operated.

Subsequently, a second layer 304 including NPB was formed on the first layer 303 by evaporation. The thickness of the second layer 304 was set to be 10 nm. The second layer 304 serves as a hole transporting layer when the light emitting element is operated.

A third layer 305 including DPCzPA and PCABPA was formed on the second layer 304 by co-evaporation. The thickness of the third layer 305 was set to be 40 nm. The mass ratio between DPCzPA and PCABPA was adjusted to be 1:0.04. Thus, the PCABPA was dispersed in the DPCzPA. The third layer 305 serves as a light emitting layer when the light emitting element is operated. Further, the PCABPA serves as a light emitting substance.

Next, a fourth layer 306 including $Alq_3$ was formed on the third layer 305 by evaporation. The thickness of the fourth layer 306 was set to be 10 nm. The fourth layer 306 serves as an electron transporting layer when the light emitting element is operated.

A fifth layer 307 including $Alq_3$ and Li was formed on the fourth layer 306 by co-evaporation. The thickness of the fifth layer 307 was set to be 10 nm. The mass ratio between $Alq_3$ and Li was adjusted to be 1:0.01. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where a temperature was maintained at 25° C.).

Figure 31:
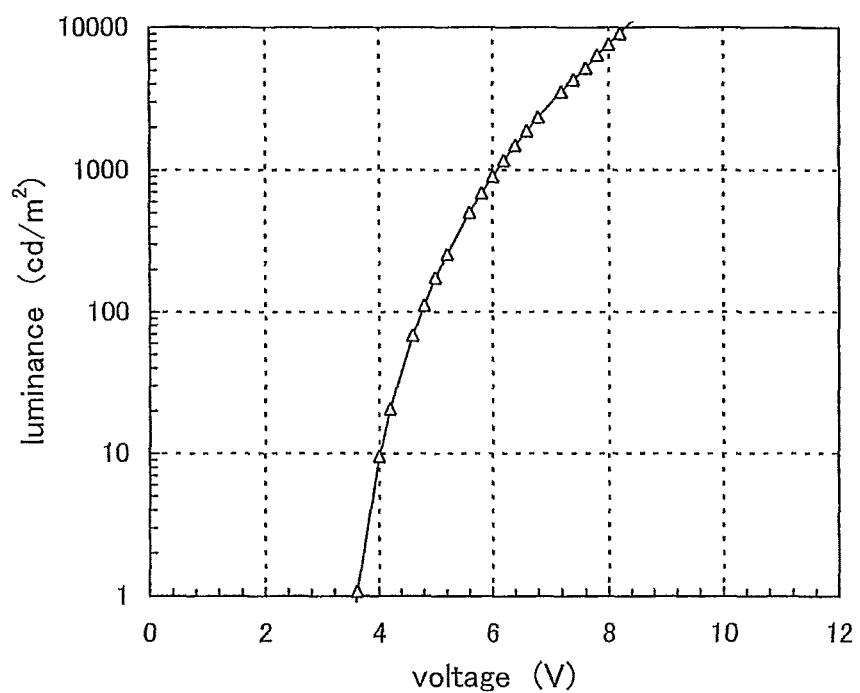
FIG. 31 is a graph showing a luminance-voltage characteristic of a light emitting element manufacturing in Embodiment 7.
Figure 32:
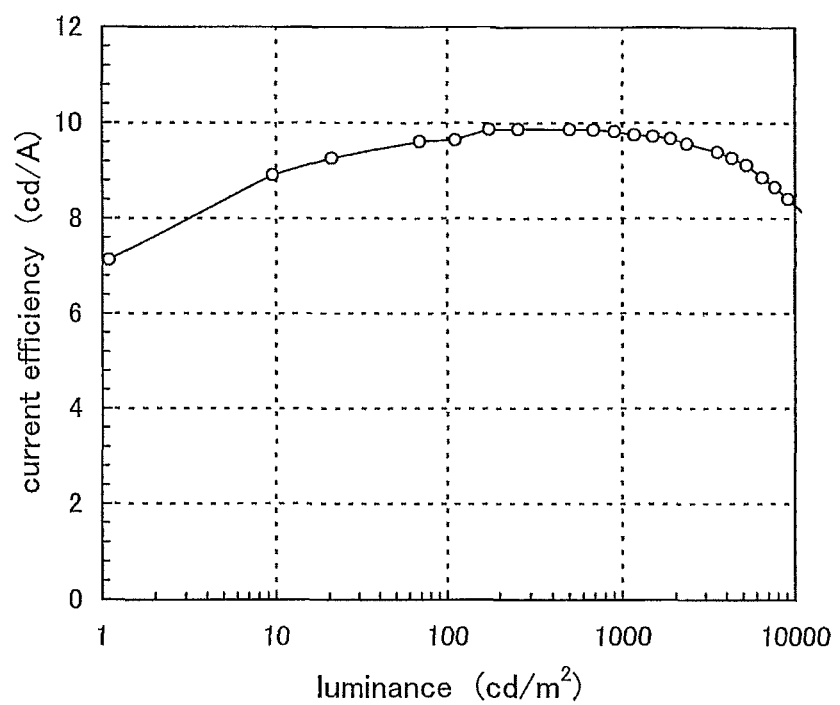
FIG. 32 is a graph showing a luminance-current efficiency characteristic of a light emitting element manufacturing in Embodiment 7.

Measurement results are shown in FIG. 31 and FIG. 32. FIG. 31 shows a measurement result of a voltage-luminance characteristic, whereas FIG. 32 shows a measurement result of a luminance-current efficiency characteristic. In FIG. 31, a horizontal axis represents the voltage (V) and a longitudinal axis represents the luminance ($cd/m^2$). Also, in FIG. 32, a horizontal axis represents the luminance ($cd/m^2$) and a longitudinal axis represents the current efficiency (cd/A).

Figure 33:
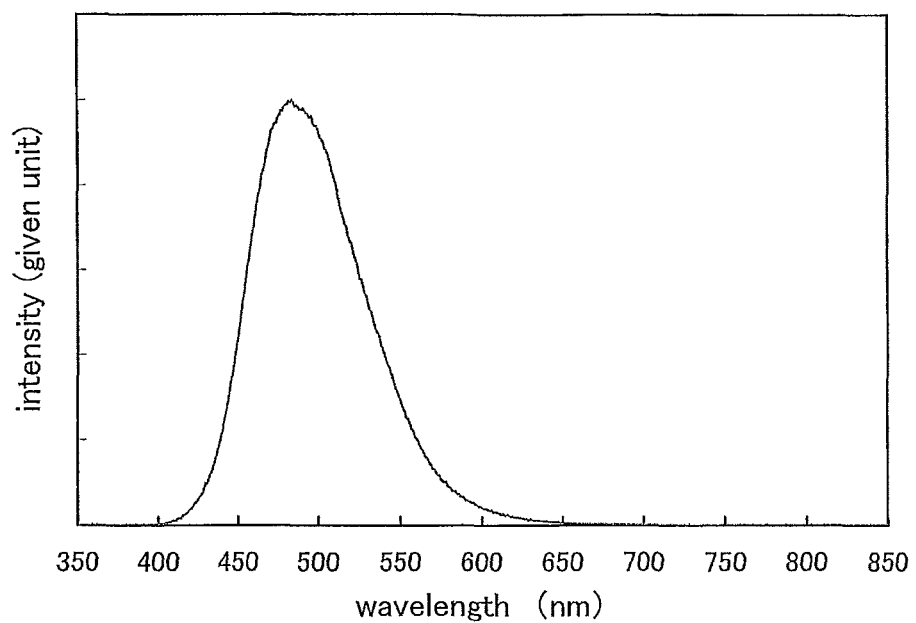
FIG. 33 is a graph showing a light emission spectrum of a light emitting element manufactured in Embodiment 7.

The light emission spectrum of the light emitting element manufactured in this embodiment is shown in FIG. 33. In FIG. 33, a horizontal axis represents a wavelength (nm) and a longitudinal axis represents the intensity (given unit). According to FIG. 33, it was known that the light emitting element of the present embodiment had a peak of light emission spectrum at 487 nm, and emitted blue light. Moreover, the CIE chromaticity coordinates were x=0.17, y=0.32. As a consequence, it was known that the light emitting element of the present embodiment emitted blue light with good color purity.

[Embodiment 8]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1 \times 10^{-4}$ Pa. Then, a first layer 303 including DNTPD was formed on the first electrode 302 by evaporation. The thickness of the first layer 303 was set to be 50 nm. The first layer 303 serves as a hole injecting layer when the light emitting element is operated.

Subsequently, a second layer 304 including NPB was formed on the first layer 303 by evaporation. The thickness of the second layer 304 was set to be 10 nm. The second layer 304 serves as a hole transporting layer when the light emitting element is operated.

A third layer 305 including t-BuDNA and PCABPA was formed on the second layer 304 by co-evaporation. The thickness of the third layer 305 was set to be 40 nm. The mass ratio between t-BuDNA and PCABPA was adjusted to be 1:0.04. Thus, the PCABPA was dispersed in the t-BuDNA. The third layer 305 serves as a light emitting layer when the light emitting element is operated. Further, the PCABPA serves as a light emitting substance.

Next, a fourth layer 306 including $Alq_3$ was formed on the third layer 305 by evaporation. The thickness of the fourth layer 306 was set to be 10 nm. The fourth layer 306 serves as an electron transporting layer when the light emitting element is operated.

A fifth layer 307 including $Alq_3$ and Li was formed on the fourth layer 306 by co-evaporation. The thickness of the fifth layer 307 was set to be 10 nm. The mass ratio between $Alq_3$ and Li was adjusted to be 1:0.01. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and elections are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where a temperature was maintained at 25° C.).

Figure 34:
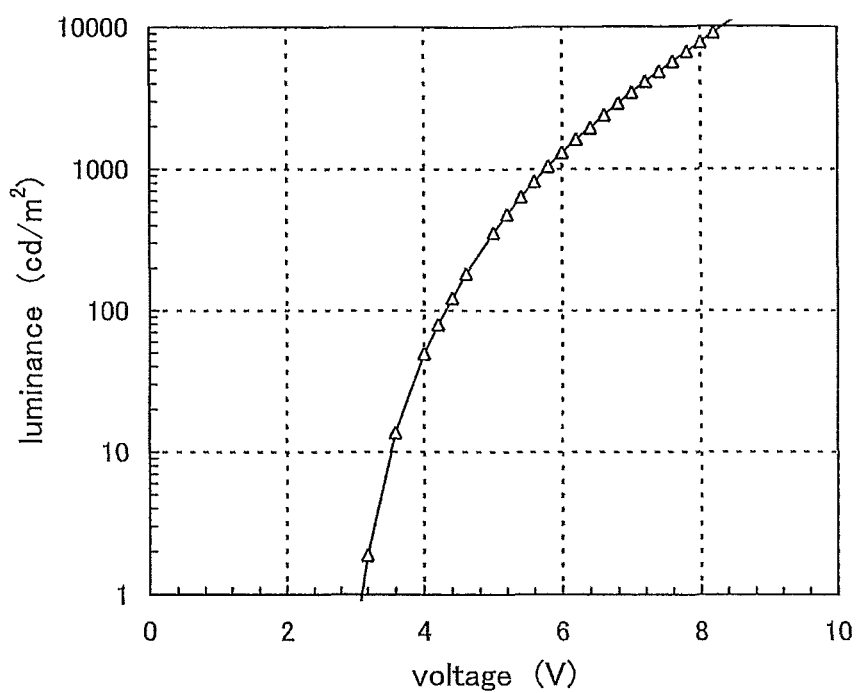
FIG. 34 is a graph showing a luminance-voltage characteristic of a light emitting element manufacturing in Embodiment 8.
Figure 35:
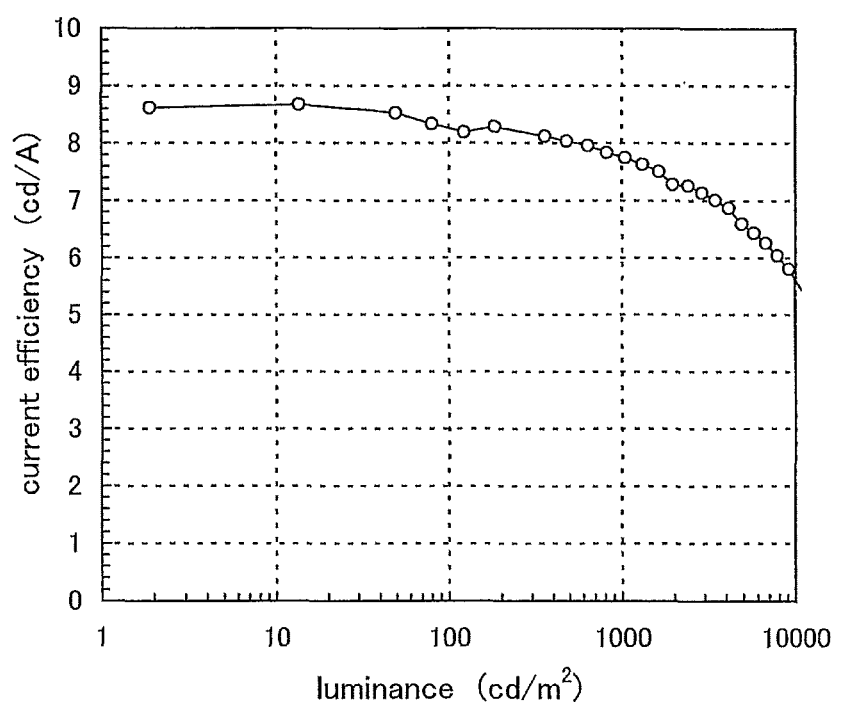
FIG. 35 is a graph showing a luminance-current efficiency characteristic of a light emitting element manufacturing in Embodiment 8.

Measurement results are shown in FIG. 34 and FIG. 35. FIG. 34 shows a measurement result of a voltage-luminance characteristic, whereas FIG. 35 shows a measurement result of a luminance-current efficiency characteristic. In FIG. 34, a horizontal axis represents the voltage (V) and a longitudinal axis represents the luminance ($cd/m^2$). Also, in FIG. 35, a horizontal axis represents the luminance ($cd/m^2$) and a longitudinal axis represents the current efficiency (cd/A).

Figure 36:
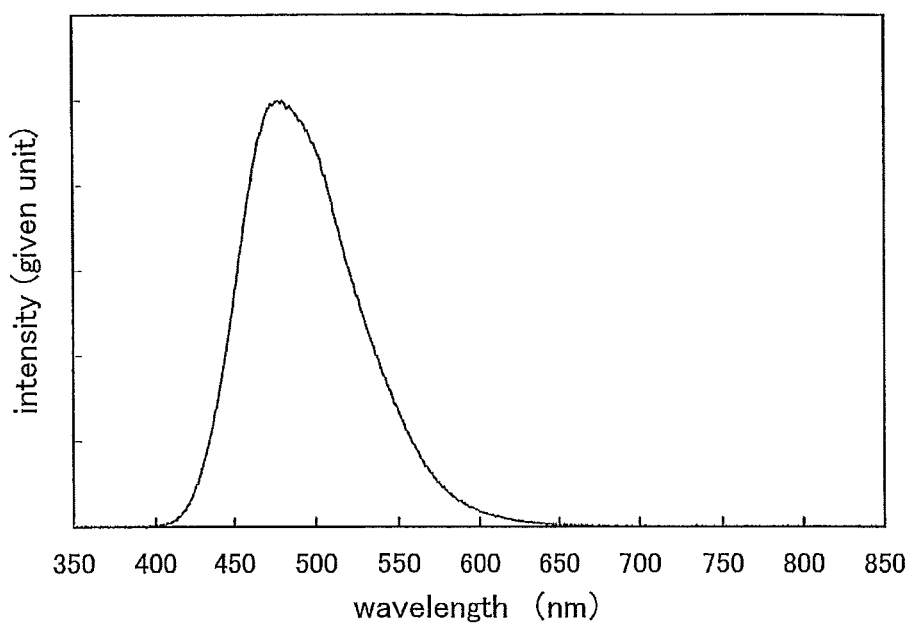
FIG. 36 is a graph showing a light emission spectrum of a light emitting element manufactured in Embodiment 8.

The light emission spectrum of the light emitting element manufactured in this embodiment is shown in FIG. 36. In FIG. 36, a horizontal axis represents a wavelength (nm) and a longitudinal axis represents the intensity (given unit). According to FIG. 36, it was known that the light emitting element of the present embodiment had a peak of light emission spectrum at 482 nm, and emitted blue light. Moreover, the CIE chromaticity coordinates were x=0.16, y=0.29. As a result, it was known that the light emitting element of the present embodiment emitted blue light with good color purity.

[Embodiment 9]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1\times10^{-4}$ Pa. Then, a first layer 303 including CuPc was formed on the first electrode 302 by evaporation. The thickness of the first layer 303 was set to be 20 nm. The first layer 303 serves as a hole injecting layer when the light emitting element is operated.

Subsequently, a second layer 304 including NPB was formed on the first layer 303 by evaporation. The thickness of the second layer 304 was set to be 40 nm. The second layer 304 serves as a hole transporting layer when the light emitting element is operated.

A third layer 305 including CzPA and PCABPA was formed on the second layer 304 by co-evaporation. The thickness of the third layer 305 was set to be 40 inn. The mass ratio between CzPA and PCABPA was adjusted to be 1:0.04. Thus, the PCABPA was dispersed in the CzPA. The third layer 305 serves as a light emitting layer when the light emitting element is operated. Further, the PCABPA serves as a light emitting substance.

Next, a fourth layer 306 including $Alq_3$ was formed on the third layer 305 by evaporation. The thickness of the fourth layer 306 was set to be 10 nm. The fourth layer 306 serves as an electron transporting layer when the light emitting element is operated.

A fifth layer 307 including $Alq_3$ and Li was formed on the fourth layer 306 by co-evaporation. The thickness of the fifth layer 307 was set to be 10 nm. The mass ratio between $Alq_3$ and Li was adjusted to be 1:0.01. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where a temperature was maintained at 25° C.).

Figure 37:
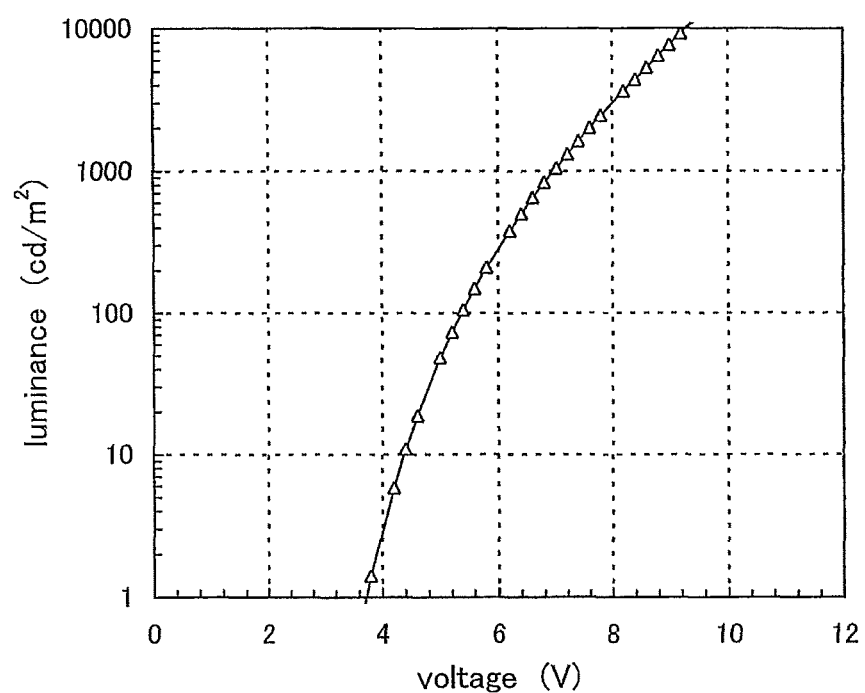
FIG. 37 is a graph showing a luminance-voltage characteristic of a light emitting element manufacturing in Embodiment 9.
Figure 38:
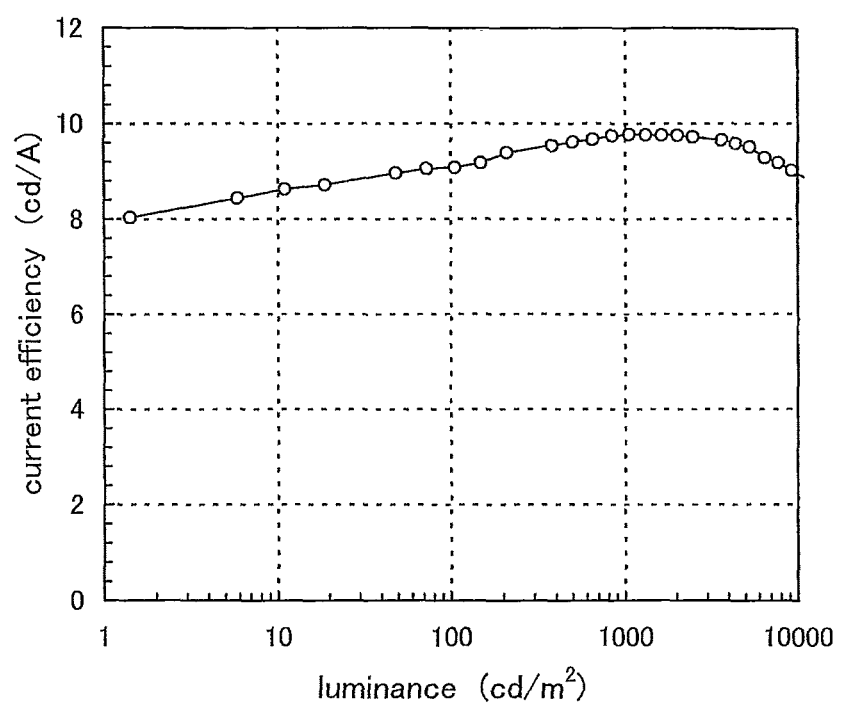
FIG. 38 is a graph showing a luminance-current efficiency characteristic of a light emitting element manufacturing in Embodiment 9.

Measurement results are shown in FIG. 37 and FIG. 38. FIG. 37 shows a measurement result of a voltage-luminance characteristic, whereas FIG. 38 shows a measurement result of a luminance-current efficiency characteristic. In FIG. 37, a horizontal axis represents the voltage (V) and a longitudinal axis represents the luminance ($cd/m^2$). Also, in FIG. 38, a horizontal axis represents the luminance ($cd/m^2$) and a longitudinal axis represents the current efficiency (cd/A).

Figure 39:
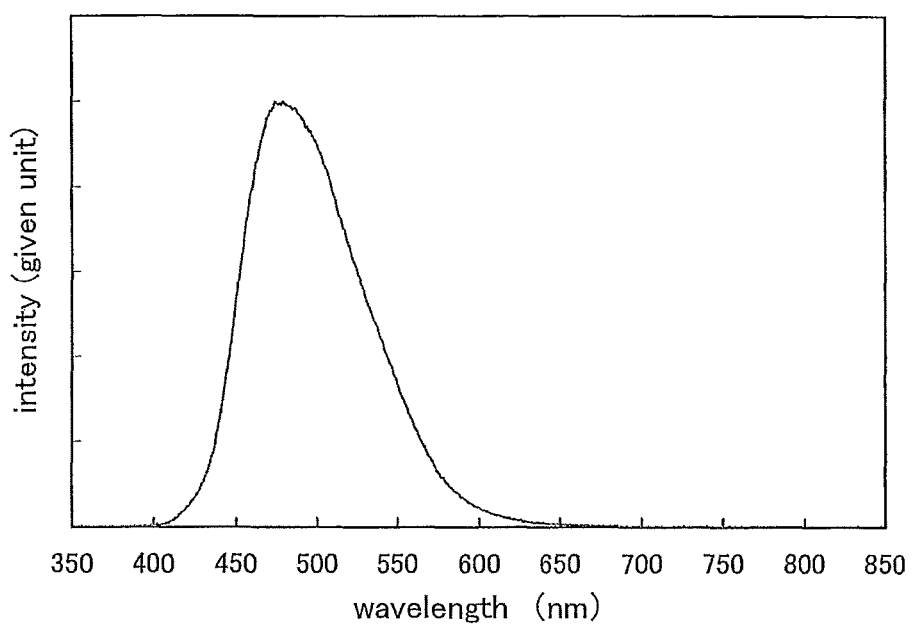
FIG. 39 is a graph showing a light emission spectrum of a light emitting element manufactured in Embodiment 9.

The light emission spectrum of the light emitting element manufactured in this embodiment is shown in FIG. 39. In FIG. 39, a horizontal axis represents a wavelength (nm) and a longitudinal axis represents the intensity (given unit). According to FIG. 39, it was known that the light emitting element of the present embodiment had a peak of light emission spectrum at 481 nm, and emitted blue light. Moreover, the CIE chromaticity coordinates were x=0.17, y=0.31. As a consequence, it was known that the light emitting element of the present embodiment emitted blue light with good color purity.

[Embodiment 10]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1\times10^{-4}$ Pa. Then, a first layer 303 including CuPc was formed on the first electrode 302 by evaporation. The thickness of the first layer 303 was set to be 20 nm. The first layer 303 serves as a hole injecting layer when the light emitting element is operated.

Subsequently, a second layer 304 including NPB was formed on the first layer 303 by evaporation. The thickness of the second layer 304 was set to be 40 nm. The second layer 304 serves as a hole transporting layer when the light emitting element is operated.

A third layer 305 including DPCzPA and PCABPA was formed on the second layer 304 by co-evaporation. The thickness of the third layer 305 was set to be 40 nm. The mass ratio between DPCzPA and PCABPA was adjusted to be 1:0.04. Thus, the PCABPA was dispersed in the DPCzPA. The third layer 305 serves as a light emitting layer when the light emitting element is operated. Further, the PCABPA serves as a light emitting substance.

Next, a fourth layer 306 including $Alq_3$ was formed on the third layer 305 by evaporation. The thickness of the fourth layer 306 was set to be 10 nm. The fourth layer 306 serves as an electron transporting layer when the light emitting element is operated.

A fifth layer 307 including $Alq_3$ and Li was formed on the fourth layer 306 by co-evaporation. The thickness of the fifth layer 307 was set to be 10 nm. The mass ratio between $Alq_3$ and Li was adjusted to be 1:0.01. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 sewing as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where a temperature was maintained at 25° C.).

Figure 40:
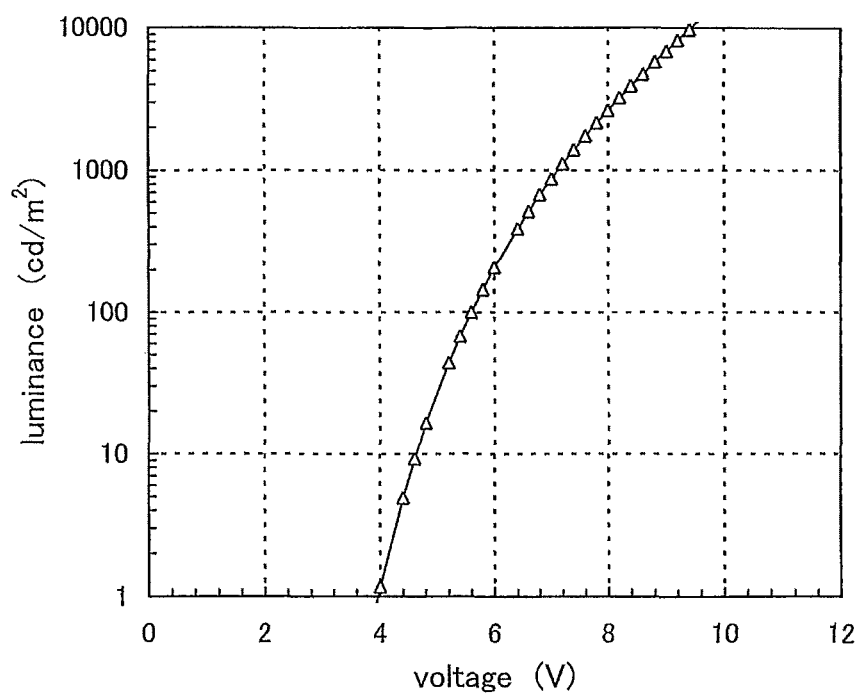
FIG. 40 is a graph showing a luminance-voltage characteristic of a light emitting element manufacturing in Embodiment 10.
Figure 41:
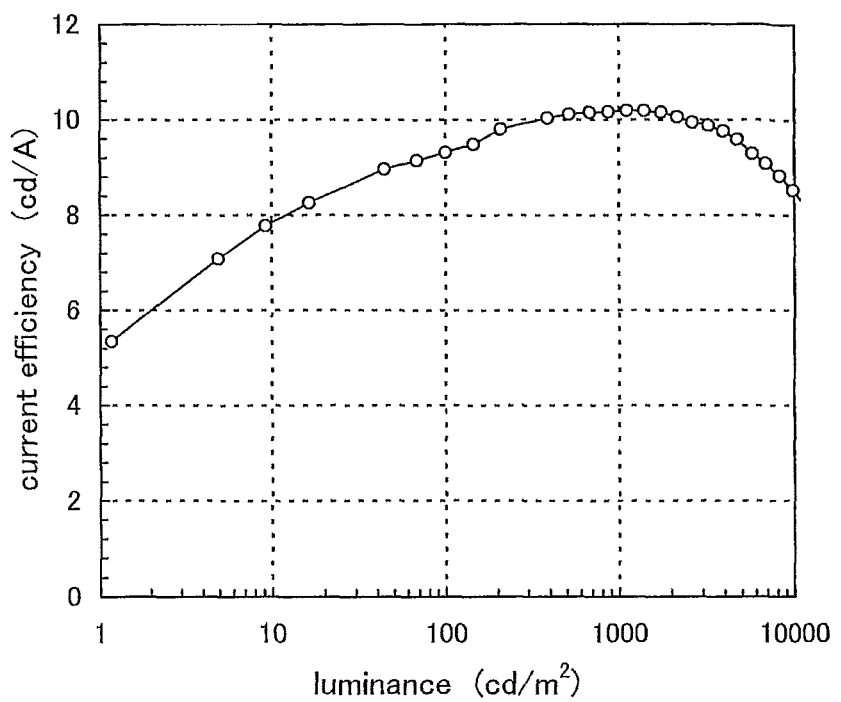
FIG. 41 is a graph showing a luminance-current efficiency characteristic of a light emitting element manufacturing in Embodiment 10.

Measurement results are shown in FIG. 40 and FIG. 41. FIG. 40 shows a measurement result of a voltage-luminance characteristic, whereas FIG. 41 shows a measurement result of a luminance-current efficiency characteristic. In FIG. 40, a horizontal axis represents the voltage (V) and a longitudinal axis represents the luminance ($cd/m^2$). Also, in FIG. 41, a horizontal axis represents the luminance ($cd/m^2$) and a longitudinal axis represents the current efficiency (cd/A).

Figure 42:
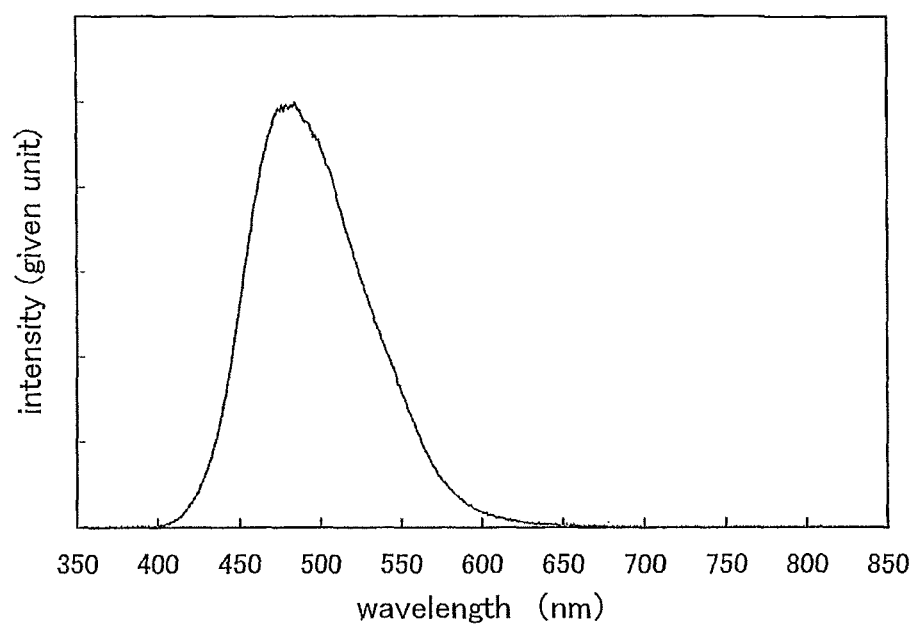
FIG. 42 is a graph showing a light emission spectrum of a light emitting element manufactured in Embodiment 10.

The light emission spectrum of the light emitting element manufactured in this embodiment is shown in FIG. 42. In FIG. 42, a horizontal axis represents a wavelength (nm) and a longitudinal axis represents the intensity (given unit). According to FIG. 42, it was known that the light emitting element of the present embodiment had a peak of light emission spectrum at 485 nm, and emitted blue light. Moreover, the CIE chromaticity coordinates were x=0.17, y=0.31. As a consequence, it was known that the light emitting element of the present embodiment emitted blue light with good color purity.

[Embodiment 11]

A method for manufacturing a light emitting element that uses the PCABPA synthesized in Synthetic Example 1 as a light emitting substance and an operational characteristic of the light emitting element will be described in this embodiment. Further, a light emitting element of the present embodiment is similar to the light emitting element of Embodiment 2 in a point of having a structure in which five layers are laminated between a first electrode and a second electrode, wherein substances and thicknesses of these layers are different from one another. The present embodiment will be described with reference to FIG. 15 also used in the description of Embodiment 2.

As shown in FIG. 15, indium tin oxide containing silicon oxide was formed over a glass substrate 301 by sputtering to form a first electrode 302. The thickness of the first electrode 302 was set to be 110 nm. Further, the first electrode was formed to have a square shape having the size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1\times10^{-4}$ Pa. Then, a first layer 303 including CuPc was formed on the first electrode 302 by evaporation. The thickness of the first layer 303 was set to be 20 nm. The first layer 303 serves as a hole injecting layer when the light emitting element is operated.

Subsequently, a second layer 304 including NPB was formed on the first layer 303 by evaporation. The thickness of the second layer 304 was set to be 40 nm. The second layer 304 serves as a hole transporting layer when the light emitting element is operated.

A third layer 305 including t-BuDNA and PCABPA was formed on the second layer 304 by co-evaporation. The thickness of the third layer 305 was set to be 40 nm. The mass ratio between t-BuDNA and PCABPA was adjusted to be 1:0.04. Thus, the PCABPA was dispersed in the t-BuDNA. The third layer 305 serves as a light emitting layer when the light emitting element is operated. Further, the PCABPA serves as a light emitting substance.

Next, a fourth layer 306 including Alq₃ was formed on the third layer 305 by evaporation. The thickness of the fourth layer 306 was set to be 10 nm. The fourth layer 306 serves as an electron transporting layer when the light emitting element is operated.

A fifth layer 307 including Alq₃ and Li was formed on the fourth layer 306 by co-evaporation. The thickness of the fifth layer 307 was set to be 10 nm. The mass ratio between Alq₃ and Li was adjusted to be 1:0.01. The fifth layer 307 serves as an electron injecting layer when the light emitting element is operated.

Next, a second electrode 308 including aluminum was formed on the fifth layer 307. The thickness of the second electrode 308 was set to be 200 nm.

When the voltage is applied to the light emitting element manufactured above such that a potential of the first electrode 302 is higher than that of the second electrode 308, current flows through the light emitting element. Holes and electrons are recombined at the third layer 305 serving as a light emitting layer to generate excited energy. The excited PCABPA emits light upon returning to a ground state.

This light emitting element was sealed in a glove box under nitrogen atmosphere so as not to expose the light emitting element to the atmospheric air. Thereafter, an operational characteristic of the light emitting element was measured. Further, the measurement was carried out at a room temperature (under an atmosphere where a temperature was maintained at 25° C.).

Figure 43:
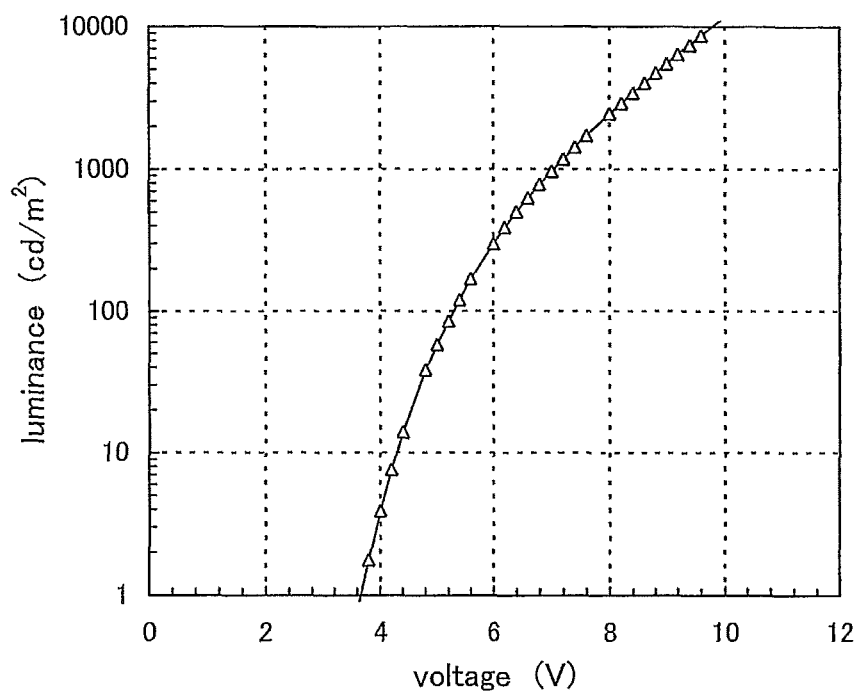
FIG. 43 is a graph showing a luminance-voltage characteristic of a light emitting element manufacturing in Embodiment 11.
Figure 44:
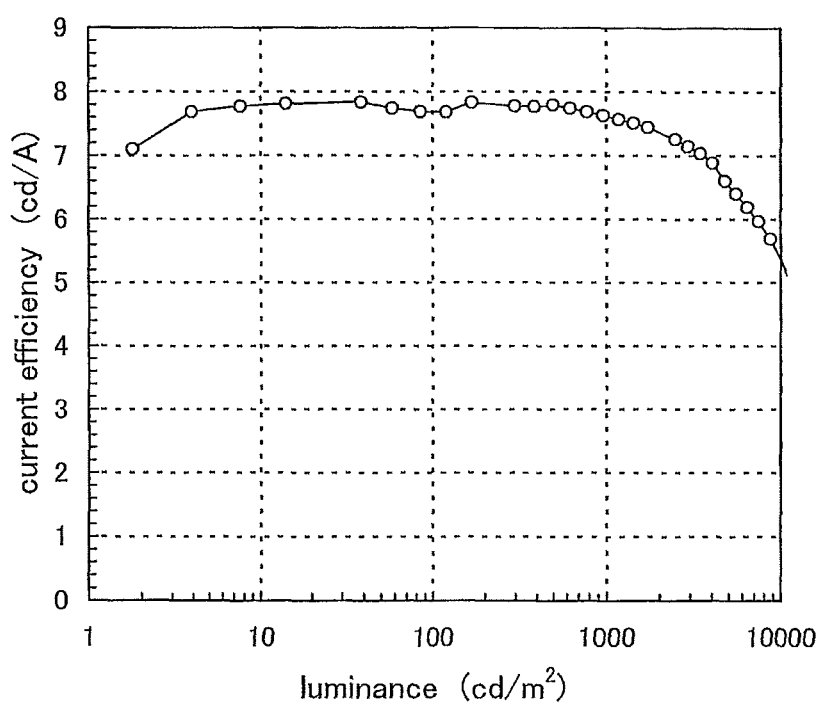
FIG. 44 is a graph showing a luminance-current efficiency characteristic of a light emitting element manufacturing in Embodiment 11.

Measurement results are shown in FIG. 43 and FIG. 44. FIG. 43 shows a measurement result of a voltage-luminance characteristic, whereas FIG. 44 shows a measurement result of a luminance-current efficiency characteristic. In FIG. 43, a horizontal axis represents the voltage (V) and a longitudinal axis represents the luminance (cd/m²). Also, in FIG. 44, a horizontal axis represents the luminance (cd/m²) and a longitudinal axis represents the current efficiency (cd/A).

Figure 45:
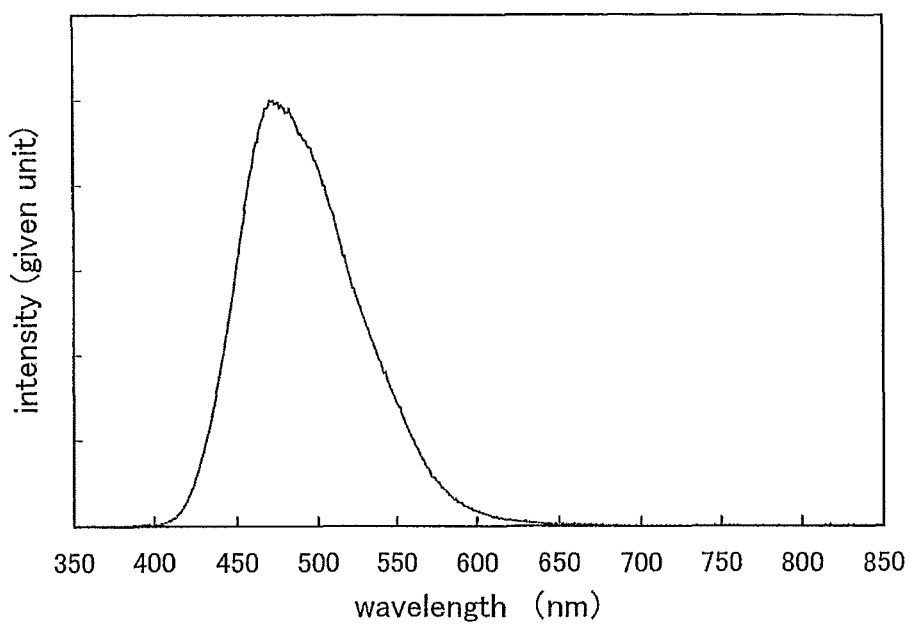
FIG. 45 is a graph showing a light emission spectrum of a light emitting element manufactured in Embodiment 11.

The light emission spectrum of the light emitting element manufactured in this embodiment is shown in FIG. 45. In FIG. 45, a horizontal axis represents a wavelength (nm) and a longitudinal axis represents the intensity (given unit). According to FIG. 45, it was known that the light emitting element of the present embodiment had a peak of light emission spectrum at 476 nm, and emitted blue light. Moreover, the CIE chromaticity coordinates were x=0.16; y=0.28. As a consequence, it was known that the light emitting element of the present embodiment emitted blue light with good color purity.

What is claimed is:

1. A compound represented by the following formula:

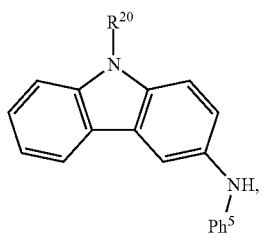

wherein:
R²⁰ is a substituted or unsubstituted aryl group; and
Ph⁵ is a substituted or unsubstituted phenyl group.

2. The compound according to claim 1,
wherein R²⁰ is an unsubstituted aryl group.

3. The compound according to claim 1,
wherein R²⁰ is selected from a phenyl group, a biphenyl group, and a naphthyl group.

4. The compound according to claim 1,
wherein R²⁰ is an unsubstituted aryl group selected from a phenyl group, a biphenyl group, and a naphthyl group.

5. The compound according to claim 1,
wherein Ph⁵ is an unsubstituted phenyl group.

6. The compound according to claim 1,
wherein the compound is represented by the following formula:

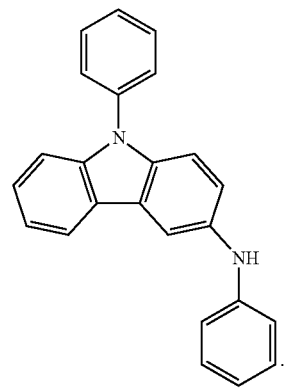 [SMILES: c1ccc(Nc2ccc3c(c2)c2ccccc2n3-c2ccccc2)cc1]

7. A method for synthesizing a carbazole-containing compound, the method includes:
reacting an organic halide with a compound represented by the following formula:

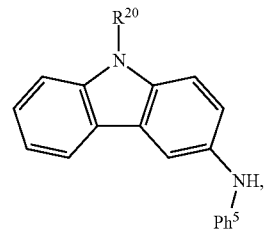

wherein:
R²⁰ is a substituted or unsubstituted aryl group; and
Ph⁵ is a substituted or unsubstituted phenyl group.

8. The method according to claim 7,
wherein R²⁰ is an unsubstituted aryl group.

9. The method according to claim 7,
wherein R²⁰ is selected from a phenyl group, a biphenyl group, and a naphthyl group.

10. The method according to claim 7,
wherein R²⁰ is an unsubstituted aryl group selected from a phenyl group, a biphenyl group, and a naphthyl group.

11. The method according to claim 7,
wherein Ph⁵ is an unsubstituted phenyl group.

12. The method according to claim 7,
wherein the compound is represented by the following formula:

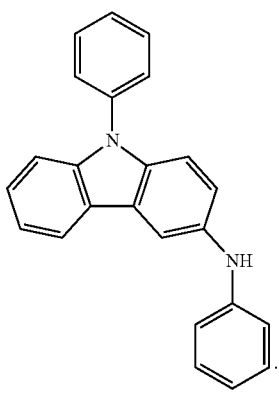 [SMILES: c1ccc(Nc2ccc3c(c2)c2ccccc2n3-c2ccccc2)cc1]

13. The method according to claim 7, wherein the organic halide includes an anthracene unit.

14. A method for synthesizing a compound represented by the following formula:

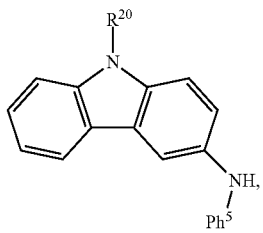

the method includes a reaction comprising the steps of:
substituting hydrogen with bromo at a three position of a compound that contains carbazole in a skeleton; and
substituting the bromo with an amino group, wherein:
$R^{20}$ is a substituted or unsubstituted aryl group; and
$Ph^5$ is a substituted or unsubstituted phenyl group.

15. The method according to claim 14, wherein the reaction is represented by a scheme (a-3):

(a-3)

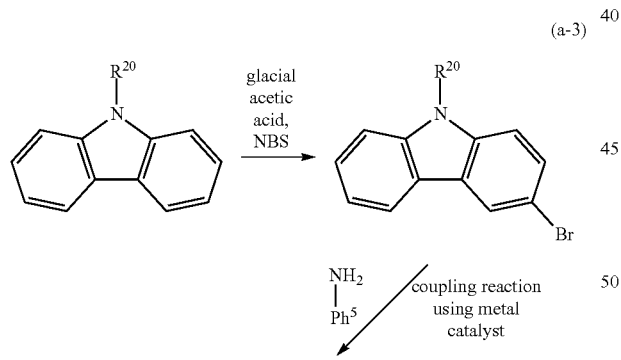

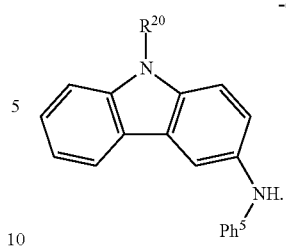

16. The method according to claim 14,
wherein $R^{20}$ is an unsubstituted aryl group.

17. The method according to claim 14,
wherein $R^{20}$ is selected from a phenyl group, a biphenyl group, and a naphthyl group.

18. The method according to claim 14,
wherein $R^{20}$ is an unsubstituted aryl group selected from a phenyl group, a biphenyl group, and a naphthyl group.

19. The method according to claim 14,
wherein $Ph^5$ is an unsubstituted phenyl group.

20. The method according to claim 14,
wherein the compound is represented by the following formula:

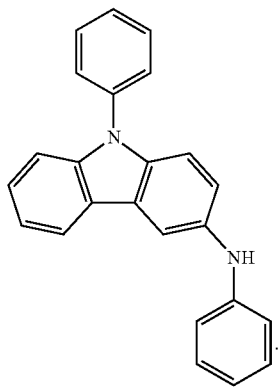 [SMILES: c1ccc(Nc2ccc3c(c2)c2ccccc2n3-c2ccccc2)cc1]

* * * * *

UNITED STATES PATENT AND TRADEMARK OFFICE
CERTIFICATE OF CORRECTION

PATENT NO. : 9,478,751 B2  
APPLICATION NO. : 14/466422  
DATED : October 25, 2016  
INVENTOR(S) : Harue Nakashima et al.

Page 1 of 2

It is certified that error appears in the above-identified patent and that said Letters Patent is hereby corrected as shown below:

In the Specification

Column 41, Line 56; Change "phenylamine]" to --phenylamino]--.

Column 42, Line 23; Change "election" to --electron--.

Column 42, Line 37; Change "thiazole" to --triazole--.

Column 44, Line 64; Change "Moreover; since" to --Moreover, since--.

Column 51, Line 48; Change "$SiH_4$;" to --$SiH_4$,--.

Column 52, Line 15; Change "FIGS. 5A" to --FIGS. 8A--.

Column 60, Line 6; Change "0.6 Thom -0.01" to --0.6 V from -0.01--.

Column 60, Line 47; Change "655 g" to --6.55 g--.

Column 62, Line 32; Change "phenylamine]" to --phenylamino]--.

Column 62, Line 46; Change "(4:0" to --(4.0--.

Column 64, Line 35; Change "it Was" to --it was--.

Column 65, Line 62; Change "five," to --five--.

Column 67, Line 26; Change "Further; the" to --Further, the--.

Column 67, Line 30; Change "flied" to --fixed--.

Signed and Sealed this  
Twenty-third Day of May, 2017

Michelle K. Lee  
*Director of the United States Patent and Trademark Office*

CERTIFICATE OF CORRECTION (continued)
U.S. Pat. No. 9,478,751 B2

Column 68, Line 10; Change "where, a" to --where a--.

Column 73, Line 23; Change "elections" to --electrons--.

Column 74, Line 21; Change "40 inn." to --40 nm.--.

Column 75, Line 67; Change "sewing" to --serving--.

Column 77, Line 47; Change "x=0.16;" to --x=0.16,--.